(12) United States Patent
Novick et al.

(10) Patent No.: US 7,799,541 B2
(45) Date of Patent: *Sep. 21, 2010

(54) INTERLEUKIN-18 BINDING PROTEINS, THEIR PREPARATION AND USE

(75) Inventors: Daniela Novick, Rehovot (IL); Charles Dinarello, Boulder, CO (US); Menachem Rubinstein, Rehovot (IL); Soo Hyun Kim, Aurora, CO (US)

(73) Assignee: Yeda Research and Development Company Ltd., Rehovot (IL)

( * ) Notice: Subject to any disclaimer, the term of this patent is extended or adjusted under 35 U.S.C. 154(b) by 525 days.

This patent is subject to a terminal disclaimer.

(21) Appl. No.: 11/376,794

(22) Filed: Mar. 15, 2006

(65) Prior Publication Data

US 2006/0154294 A1    Jul. 13, 2006

Related U.S. Application Data

(60) Continuation of application No. 10/434,583, filed on May 8, 2003, now Pat. No. 7,101,689, which is a division of application No. 09/485,632, filed as application No. PCT/IL98/00379 on Aug. 13, 1998, now Pat. No. 6,605,280.

(30) Foreign Application Priority Data

| Aug. 14, 1997 | (IL) | 121554 |
| Aug. 27, 1997 | (IL) | 121639 |
| Sep. 29, 1997 | (IL) | 121860 |
| Nov. 6, 1997 | (IL) | 122134 |
| Jul. 22, 1998 | (IL) | 125463 |

(51) Int. Cl.
*C12P 21/06* (2006.01)
*C12N 5/00* (2006.01)
*C12N 15/00* (2006.01)
*C07H 21/02* (2006.01)
*C07H 21/04* (2006.01)

(52) U.S. Cl. ............ 435/69.1; 435/320.1; 435/325; 435/455; 435/252.1; 435/471; 536/23.1; 536/23.5

(58) Field of Classification Search .......... None
See application file for complete search history.

(56) References Cited

U.S. PATENT DOCUMENTS

| 5,776,731 A | 7/1998 | Parnet et al. ............... 435/69.1 |
| 5,932,549 A | 8/1999 | Allen et al. .................... 514/18 |
| 5,985,863 A | 11/1999 | Su et al. ....................... 514/183 |
| 6,087,116 A | 7/2000 | Torigoe et al. ............. 435/7.21 |

FOREIGN PATENT DOCUMENTS

| EP | 0850952 | 7/1990 |
| EP | 0864585 | 9/1998 |
| EP | 0974600 | 8/2000 |
| WO | WO 98/22137 | 5/1998 |
| WO | WO 98/24804 | 6/1998 |
| WO | WO 98/41232 | 9/1998 |
| WO | WO 99/06549 | 2/1999 |
| WO | WO 99/06553 | 2/1999 |
| WO | WO 99/55377 | 11/1999 |
| WO | WO 00/12555 | 3/2000 |
| WO | WO 00/56771 | 9/2000 |
| WO | WO 01/03719 | 1/2001 |
| WO | WO 01/19373 | 3/2001 |

OTHER PUBLICATIONS

Kim et al. J Biol. Chem. 277(13):10998-11003, 2002.*
Ngo, in The Protein Folding Problem and Tertiary Structure Prediction, Merz et al. (eds.), Birkhauser Boston: Boston, MA, pp. 433 and 492-495, 1994). Rudinger (in Peptide Hormones, Parsons (ed.), University Park Press: Baltimore, MD, pp. 1-7, 1976.*
Rudinger (in Peptide Hormones, Parsons (ed.), University Park Press: Baltimore, MD, pp. 1-7, 1976.*
New England Biolabs Catalog Product # 1230, 1988-1089.*
Juengst BMJ, 326:1410-11, 2003.*
Rosenberg et al, Science 287:1751, 2000.*
Verma et al Nature 389:239-242, 1997.*
Touchette, Nat. Med. 2(1) 7-8, 1996.*
Adams, et al. EMBL Database Entry HSZZ16951, GenBank accession No. AA311795 (Apr. 18, 1997).
Adams, et al. EMBL Database Entry HZZ03012, GenBank accession No. gl950205 (Apr. 18, 1997).
Afford, et al. (1998). *J. Pathol.* 186:82-89.
Aizawa, et al. (1999). *FEBS Lett.* 445:338-342.
Akira, (2000). *Curr.Opin. Immunol.* 12:59-63.
Akita, et al. (1997). *J. Biol. Chem.* 272:26595-26603.
Anderson, et al. (1997). *Nature* 390:175-179.
Attwood, (2000). *Science* 290:471-473.
Baroni, et al. (1999). *Liver* 19: 212-219.
Bird, et al. (1990). *Ann. Internal Med.* 112:917-920.
Bollon, et al. (1980). *J. Clin. Hematol. Oncol.* 10:39-48.
Botstein, et al. (1982). *Miami Wint. Symp.* 19:265-274.
Broach, (1982). *Cell* 28:203-204.
Broach, (1981). *Cold Spring Harbor Laboratory*, Cold Sprong Harbor, NY, pp. 445-470.
Bym, et al. (1990). *Nature* (London) 344:667-670.
Camoglio, et al. (2000). *Eur. J. Immunol.* 30:1486-1495.
Car, et al. (1994). *J. Exp. Med.* 179:1437-1444.
Conti, et al. (1997). *J. Biol. Chem.* 272:2035-2037.
Dao, et al. (1996). *Cell. Immunol.* 173:230-235.
Dayer, et al. (1999). *J. Clin. Invest.* 104:1337-1339.
Debets, et al. (2000). *J. Immunol.* 165:4950-4956.
Desreumaux, et al. (1997). *Gastroenterol.* 113:118-126.
DiDonato, et al. (1997). *Nature* 388:548-554.

(Continued)

*Primary Examiner*—Sumesh Kaushal
(74) *Attorney, Agent, or Firm*—Mintz Levin Cohn Ferris Glovsky and Popeo P.C.; Ivor R. Elrifi; Cynthia Lozakiewicz

(57) ABSTRACT

Interleukin-18 binding proteins which are capable of binding IL-18 and/or modulating and/or blocking IL-18 activity are provided. Methods for their isolation and recombinant production, DNAs encoding them, DNA vectors expressing them, vecotors useful for their expression in humans and other mammals, antibodies against them are also provided.

36 Claims, 25 Drawing Sheets

OTHER PUBLICATIONS

Dinarello, et al. (1998). *J. Leukoc. Biol.* 63:658-664.
Dinarello, (2000). *Ann. Rheum. Dis.* 59(Suppl 1):117-120.
Dinarello, (1999). *J. Allergy Clin. Immunol.* 103:11-24.
Elliott, et al. (1994). *Lancet* 344:1125-1127.
EMBL Database Entry 0 00919, GenBank accession No. 0 00919 (Jan. 15, 1991).
EMBL Database Entry 0 00923, GenBank accession No. 0 00923 (Jul. 26, 1993).
Engelemann, et al. (1990). *J. Biol. Chem.* 265:1531-1536.
Engelmann, et al. (1989). *J. Biol. Chem.* 264:11974-11980.
Fantuzzi, et al. (1998). *Blood* 91:2118-2125.
Fiore, et al. (1999). *Microbios.* 97:29-38.
Galle, et al. (1995). *J. Exp. Med.* 182:1123-1230.
Ghayur, et al. (1997). *Nature* 386:619-623.
Gillespie, (1998). *Cytokine.Growth Factor. Rev.* 9:109-116.
Gracie, et al. (1999). *J.Clin. Invest.* 104:1393-1401.
Grantham, et al. (1974). *Science* 185:862-864.
Grove, et al. (1997). *Hepatol.* 26:143-146.
Gryczan, (1982). "*The Molecular Biology of the Bacilli*", Academic Press, NY pp. 307-329.
Gu, et al. (1997). *Science* 275:206-209.
Gutkind, et al. (1991). *Molec. Cell. Biol.* 11:1500-1507.
Harada, et al. (1997). *Hepatol.* 25:791-796.
Heremans, et al. (1990). *J. Exp. Med.* 171:1853-1869.
Hill, et al. (1992). *J. Lab. Clin. Med.* 119:547-552.
Hill, et al. (1993). *Hepatol.* 18:576-580.
Hillier, et al. EMBL Database Entry HSA10059, GenBank accession No. AA010059 (Nov. 29, 1996).
Hiramatsu, et al. (1994). *Hepatol.* 19:1354-1359.
Hochholzer, et al. (2000). *Infect. Immun.* 68:3502-3508.
Holmes, et al. (2000). *Hybridoma* 19:363-367.
Horwood, et al. (1998). *J. Clin. Invest.* 101:595-603.
Hoshino, et al. (1999). *J. Immunol.* 162:5041-5044.
Huang, et al. (1996). *J. Hepatol.* 24:337-384.
Hyun, et al. *PNAS* 97(3):1190-1195.
Hyun, et al. (2001) *J. Immunol.* 166:148-154.
Iio, et al. (1998). *J. Hepatol.* 29:517-523.
Izaki (1978). *Jpn. J. Bacteriol* .33:729-742.
John, et al. (1986). *Rev. Infect. Dis.* 8:693-704.
Kashiwamura, et al. (1998). *Nippon Rinsho.* 7:1798-1806.
Kendall, et al. (1987). *J. Bacteriol.* 169:4177-4183.
Kim, et al. (2000). *Proc. Natl. Acad. Sci.* 97(3):1190-1195.
Knight, et al. (1993). *Mol. Immunol.* 30:1443-1453.
Kobayashi, et al. (1997). *Clin. Immunopathol.* 85:112-116.
Kohno, et al. (1997). *J. Immunol.* 158:1541-1550.
Kunikata, et al. (1998). *Cell Immunol.* 189:135-143.
Lebel-Binay, et al. 2000). *Eur. Cytokine Network* 11:15-25.
Lee, et al. (1999). *J. Korean Med. Sci.* 14:175-181.
Leung, et al. (2000). *J. Immunol.* 164:6495-6502.
Lukkari, et al. (1999). *Alcohol & Alcoholism* 34:311-319.
Luo, et al. (1997). *J. Viral Hepatitis* 4:303-307.
Maliszewskl, et al. (1990). *J. Immunol.* 144:3028-3033.
Maniatis, "*Cell Biology: A Comprehensive Treatise. Vol. 3: Gene Expression*". Academic Press. NY, pp. 563-608, 1989.
Martinez, et al. (1992). *Alcohol* 9:455-458.
McClain, et al. (1989). *Hepatol.* 9:349-351.
McClain, et al. (1998). *Alcoholism: Clin. Exper. Res.* 22(5 Suppl.):248S-252S.
McInnes, et al. (2000). *Immunol. Today* 21:312-315.

Micallef, et al. (1996). *Eur. J. Immunol.* 26:1647-1651.
Mizushima, et al. (1990). *Nucl. Acids Res.* 18:5322-5328.
Monteleone, et al. (1999). *J. Immunol.* 163:143-147.
Muhl, et al. (2000). *Biochem. Biophys. Res. Commun.* 267:960-963.
Muneta, et al. (1999). *J. Interferon. Cytokine. Res.* 19:1289-1296.
Nakamura, et al. (1993). *Infect. Immun.* 61:64-70.
Nakamura, et al. (1989). *Infect. Immun.* 57:590-595.
Nanji, et al. (1999). *Hepatol.* 30:934-943.
Nishida, et al. (1998). *Hybridoma* 17:577-580.
Nishimura, et al. (1999). *J. Immunol.* 162: 6503-6509.
Novick, et al. (1999). *Immunity* 10:127-136.
Novick, et al. (1992). *FEBS Lett.* 314:445-448.
Novick, et al. (1994). *Cell* 77:391-400.
Novick, et al. (1989). *J. Exp. Med.* 170:1409-1414.
Ohlinger, et al. (1993). *Virchows Archiv. A Pathol. Anat.* 423:169-176.
Okamoto, et al. (1998). *Jpn. J. Pharmacol.* 78:233-235.
Okamoto, et al. (1999). *Int. J. Mol. Med.* 3:517-520.
Okamura, et al. (1995). *Nature* 378:88-91.
Okayama, et al. (1983). *Mol. Cell. Biol.* 3:280-289.
Okazaki, et al. (1996). *Digestive Diseases and Sciences* 41:2453-2458.
Olee, et al. (1999). *J. Immunol.* 162:1096-1100.
Otsuka, et al. EMBL Database Entry U39847, GenBank accession No. AAB41827 (Feb. 3, 1997).
Pamet, et al. (1996). *J. Biol. Chem.* 271:3967-3970.
Pizarro, et al. (1999). *J. Immunol.* 162:6829-6835.
Plater-Zyberk, et al. (1995). *Nat. Med.* 1:781-785.
Puren, et al. (1998). *J. Clin. Invest.* 101:711-721.
Reimund, et al. (1996). *J. Clin. Immunol.* 16:144-150.
Reznikov, et al. (2000). *Proc. Natl. Acad. Sci. U.S.A.* 97:2174-2179.
Rothe, et al. (1997). *J. Clin. Invest.* 99:469-474.
Saha, et al. (1999). *Arthritis & Rheumatism* 42:1577-1587.
Sakao, et al. (1999). *Int. Immunol.* 11:471-480.
Sarvetnick, (1997). *J. Clin. Invest.* 99:371-372.
Senkevich, et al. EMBL Database Entry U60315, GenBank accession No. AAC55182 (Aug. 16, 1996).
Senkevich, et al. EMBL Database Entry U60315, GenBank accession No. AAC55181 (Aug. 16, 1996).
Sheron, et al. (1991). *Clin Exp. Immunol.* 84:449-453.
Simonet et al. (1997). *Cell* 89(2):309-319.
Skolnick et al. (2000). *Trends Biotech.* 18(1):34-39.
Sompayrac, et al. (1981). *Proc. Natl. Acad. Sci. USA*, 78:7575-7578.
Sparks, et al. (1993). *Genomics* 17:222-224.
Su, et al. (1998). *Am. J. Pathol.* 152:841-849.
Taieb, et al. (1998). *Lancet* 351:1930-1931.
Tang, et al. EMBL Database Entry HSNUMAT3G, GenBank accession No. Z14229 (Apr. 15, 1993).
Torigoe, et al. 1997). *J. Biol. Chem.* 272:25737-25742.
Triantaphyllopoulos, et al. (1999). *Arthritis & Rheumatism* 42:90-99.
Tsutsui, et al. (1996). *J. Immunol.* 157:3967-3973.
Tucci, et al. (1992). *J. Immunol.* 148:2778-2784.
Ushio, et al. (1996). *J. Immunol.* 156:4274-4279.
Williams, et al. (1994). *Proc. Natl. Acad. Sci. USA* 91:2762-2766.
Xiang et al. (1999). *Proc. Natl. Acad. Sci. USA* 96:11537-11542.
Yang, et al. EMBL Database Entry HSNUMAMR, GenBank accession No. Z115583 (Feb. 17, 1997).
Yasuda, et al. (1998). *Endocrinol.* 139:1329-1337.
Yoshimoto, et al. (1998). *J. Immunol.* 161:3400-3407.

\* cited by examiner

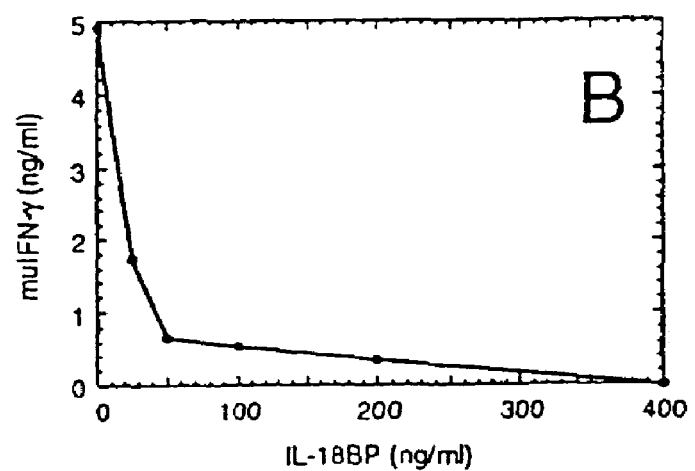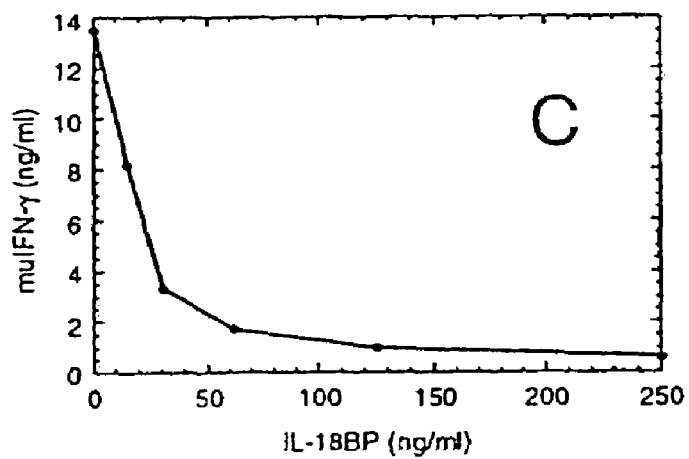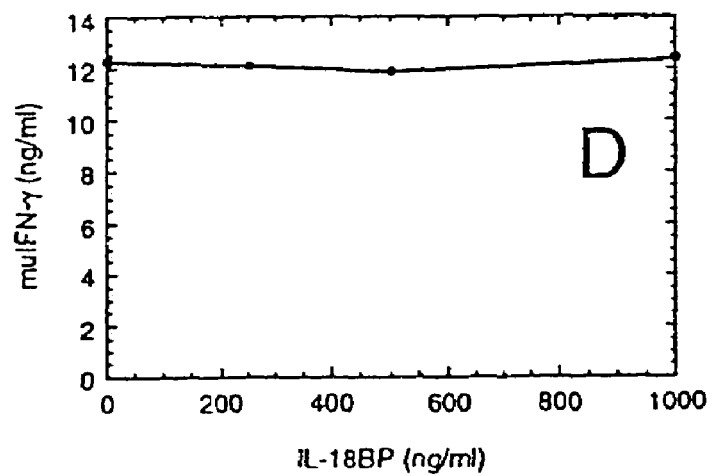
Fig. 3 B-D

IL-18Bpa; DNA sequence:

Length: 1348 December 14, 1997 15:41 Type: N Check: 2207

```
   1 GAGAAGAGGA CGTTGTCACA GATAAAGAGC CAGGCTCACC AGCTCCTGAC
  51 GCATGCATCA TGACCATGAG ACACAACTGG ACACCAGACC TCAGCCCTTT
 101 GTGGGTCCTG CTCCTGTGTG CCCACGTCGT CACTCTCCTG GTCAGAGCCA
 151 CACCTGTCTC GCAGACCACC ACAGCTGCCA CTGCCTCAGT TAGAAGCACA
 201 AAGGACCCCT GCCCCTCCCA GCCCCAGTG TTCCCAGCAG CTAAGCAGTG
 251 TCCAGCATTG GAAGTGACCT GGCCAGAGGT GGAAGTGCCA CTGAATGGAA
 301 CGCTGAGCTT ATCCTGTGTG GCCTGCAGCC GCTTCCCCAA CTTCAGCATC
 351 CTCTACTGGC TGGGCAATGG TTCCTTCATT GAGCACCTCC CAGGCCGACT
 401 GTGGGAGGGG AGCACCAGCC GGGAACGTGG GAGCACAGGT ACGCAGCTGT
 451 GCAAGGCCTT GGTGCTGGAG CAGCTGACCC CTGCCCTGCA CAGCACCAAC
 501 TTCTCCTGTG TGCTCGTGGA CCCTGAACAG GTTGTCCAGC GTCACGTCGT
 551 CCTGGCCCAG CTCTGGGCTG GGCTGAGGGC AACCTTGCCC CCCACCCAAG
 601 AAGCCCTGCC CTCCAGCCAC AGCAGTCCAC AGCAGCAGGG TTAAGACTCA
 651 GCACAGGGCC AGCAGCAGCA CAACCTTGAC CAGAGCTTGG GTCCTACCTG
 701 TCTACCTGGA GTGAACAGTC CCTGACTGCC TGTAGGCTGC GTGGATGCGC
 751 AACACACCCC CTCCTTCTCT GCTTTGGGTC CCTTCTCTCA CCAAATTCAA
 801 ACTCCATTCC CACCTACCTA GAAAATCACA GCCTCCTTAT AATGCCTCCT
 851 CCTCCTGCCA TTCTCTCTCC ACCTATCCAT TAGCCTTCCT AACGTCCTAC
 901 TCCTCACACT GCTCTACTGC TCAGAAACCA CCAAGACTGT TGATGCCTTA
 951 GCCTTGCACT CCAGGGCCCT ACCTGCATTT CCCACATGAC TTTCTGGAAG
1001 CCTCCCAACT ATTCTTGCTT TTCCCAGACA GCTCCCACTC CCATGTCTCT
1051 GCTCATTTAG TCCCGTCTTC CTCACCGCCC CAGCAGGGGA ACGCTCAAGC
1101 CTGGTTGAAA TGCTGCCTCT TCAGTGAAGT CATCCTCTTT CAGCTCTGGC
1151 CGCATTCTGC AGACTTCCTA TCTTCGTGCT GTATGTTTTT TTTTTCCCCC
1201 TTCACTCTAA TGGACTGTTC CAGGGAAGGG ATGGGGGCAC CAGCTGCTTC
```

Fig. 4

1251 GGATCCACAC TGTATCTGTG TCATCCCCAC ATGGGTCCTC ATAAAGGATT

1301 ATTCAATGGA AAAAAAAAAA AAAAAAAAAA AAAAAAAAAA AAAAAAAA (SEQ ID NO:1)

IL-18Bpa; Protein sequence:

Length: 192 June 5, 1998 13:39 Type: P Check: 3073 ..

1 MRHNWTPDLS PLWVLLLCAH VVTLLVRATP VSQTTTAATA SVRSTKDPCP

51 SQPPVFPAAK QCPALEVTWP EVEVPLNGTL SLSCVACSRF PNFSILYWLG

101 NGSFIEHLPG RLWEGSTSRE RGSTGTQLCK ALVLEQLTPA LHSTNFSCVL

151 VDPEQVVQRH VVLAQLWAGL RATLPPTQEA LPSSHSSPQQ QG (SEQ ID NO:2)

Fig. 4A

IL-18BPb; DNA sequence

Length: 1038 June 19, 1998 14:10 Type: N Check: 8005 ..

```
   1 GAGAAGAGGA CGTTGTCACA GATAAAGAGC CAGGCTCACC AGCTCCTGAC
  51 GCATGCATCA TGACCATGAG ACACAACTGG ACACCAGACC TCAGCCCTTT
 101 GTGGGTCCTG CTCCTGTGTG CCCACGTCGT CACTCTCCTG GTCAGAGCCA
 151 CACCTGTCTC GCAGACCACC ACAGCTGCCA CTGCCTCAGT TAGAAGCACA
 201 AAGGACCCCT GCCCCTCCCA GCCCCAGTG TTCCCAGCAG CTAAGCAGTG
 251 TCCAGCATTG GAAGTGACCT GGCCAGAGGT GGAAGTGCCA CTGAGCTGGG
 301 CTGAGGGCAA CCTTGCCCCC CACCCAAGAA GCCCTGCCCT CCAGCCACAG
 351 CAGTCCACAG CAGCAGGGTT AAGACTCAGC ACAGGGCCAG CAGCAGCACA
 401 ACCTTGACCA GAGCTTGGGT CCTACCTGTC TACCTGGAGT GAACAGTCCC
 451 TGACTGCCTG TAGGCTGCGT GGATGCGCAA CACACCCCCT CCTTCTCTGC
 501 TTTGGGTCCC TTCTCTCACC AAATTCAAAC TCCATTCCCA CCTACCTAGA
 551 AAATCACAGC CTCCTTATAA TGCCTCCTCC TCCTGCCATT CTCTCTCCAC
 601 CTATCCATTA GCCTTCCTAA CGTCCTACTC CTCACACTGC TCTACTGCTC
 651 AGAAACCACC AAGACTGTTG ATGCCTTAGC CTTGCACTCC AGGGCCCTAC
 701 CTGCATTTCC CACATGACTT TCTGGAAGCC TCCCAACTAT TCTTGCTTTT
 751 CCCAGACAGC TCCCACTCCC ATGTCTCTGC TCATTTAGTC CCGTCTTCCT
 801 CACCGCCCCA GCAGGGGAAC GCTCAAGCCT GGTTGAAATG CTGCCTCTTC
 851 AGTGAAGTCA TCCTCTTTCA GCTCTGGCCG CATTCTGCAG ACTTCCTATC
 901 TTCGTGCTGT ATGTTTTTTT TTTCCCCCTT CACTCTAATG GACTGTTCCA
 951 GGGAAGGGAT GGGGGCACCA GCTGCTTCGG ATCCACACTG TATCTGTGTC
1001 ATCCCCACAT GGGTCCTCAT AAAGGATTAT TCAATGGA
```

(SEQ ID NO:3)

Fig. 5 huIL-18BPb
Clone-m7
peptide

1 MRHNWTPD LSPLWVLLLC AHVVTLLVRA TPVSQTTTAA TASVRSTKDP

49 CPSQPPVFPA AKQCPALEVT WPEVEVPLSW AEGNLAPHPR SPALQPQQST

99 AAGLRLSTGP AAAQP*

(SEQ ID NO:4)

Fig. 5A huIL18BPc.seq Length: 7063 July 16, 1998 19:47 Type: N Check: 9314 ..

```
   1 GAATTCGCGG CCGCGTCGAC GCCAGAGGGG CTAGGATGAG AGACAGAGGG
  51 TGTGATGGTG GGTGCTGGGA AATGTACCCG ACCTTGGGGC TGGTGGCTGG
 101 GGGAGTGGGT AGCCTGGGAA AGGCCAGGAT GTGGACGGAC TGGTATGGCA
 151 TTGAGCCTGA AGTGGTCCAA CTTGGGGTTC CCAGTGCCT AGGAAAGTTG
 201 TCCCCTTGAA TGTCAGTGTG AAGGTGAAGG AGGAAGCAGA TGCCTGTTCA
 251 TATGGAAACA AAGACCTGGC TGTGAAGAGG GGAGGCGGAC ACCAAAGTCC
 301 TGACACTTGG GCGGGACAGA ATTGATCTGT GAGAGACTCA TCTAGTTCAT
 351 ACCCTAGGTG ACCCTGGGGG TGGCATGGGG GTAGATTAGA GATCCCAGTC
 401 TGGTATCCTC TGGAGAGTAG GAGTCCCAGG AGCTGAAGGT TTCTGGCCAC
 451 TGAACTTTGG CTAAAGCAGA GGTGTCACAG CTGCTCAAGA TTCCCTGGTT
 501 AAAAAGTGAA AGTGAAATAG AGGGTCGGGG CAGTGCTTTC CAGAAGGAT
 551 TGCTCGGCAT CCTGCCCTTC CCAGAAGCAG CTCTGGTGCT GAAGAGAGCA
 601 CTGCCTCCCT GTGTGACTGG GTGAGTCCAT ATTCTCTCTT TGGGTCTCAA
 651 TTTTGCCTTC CCTAATGAAG GGGTAAGATT GGACTAGGTA AGCATCTTAC
 701 AACCATTTGT GGTCATGAGA GCTGGGGTGG GGAAGGATTG TCACTTGACC
 751 CCCCCAGCTC TGTTTCTAAG TGCTGAAAGA GCTCCAGGCT ATGCTACGGG
 801 AGGAGAAGCC AGCTACTGAG GAAAAGCCAG CTACTGAGAA AAAGCGGGAG
 851 TGGTTTACCA TTCTCCTCCC CCACCTTTCA CCAGAGAAGA GGACGTTGTC
 901 ACACATAAAG AGCCAGGCTC ACCAGCTCCT GACGCATGCA TCATGACCAT
 951 GAGACACAAC TGGACACCAG ACCTCAGCCC TTTGTGGGTC CTGCTCCTGT
1001 GTGCCCACGT CGTCACTCTC CTGGTCAGAG CCACACCTGT CTCGCAGACC
1051 ACCACAGCTG CCACTGCCTC AGTTAGAAGC ACAAAGGACC CCTGCCCCTC
1101 CCAGCCCCCA GTGTTCCCAG CAGCTAAGCA GTGTCCAGCA TTGGAAGTGA
1151 CCTGGCCAGA GGTGGAAGTG CCACTGAATG GAACGCTGAG CTTATCCTGT
1201 GTGGCCTGCA GCCGCTTCCC CAACTTCAGC ATCCTCTACT GGCTGGGCAA
```

Fig. 6

1251 TGGTTCCTTC ATTGAGCACC TCCCAGGCCG ACTGTGGGAG GGGAGCACCA

1301 GCCGGGAACG TGGGAGCACA GGTACGCAGC TGTGCAAGGC CTTGGTGCTG

1351 GAGCAGCTGA CCCCTGCCCT GCACAGCACC AACTTCTCCT GTGTGCTCGT

1401 GGACCCTGAA CAGGTTGTCC AGCGTCACGT CGTCCTGGCC CAGCTCTGGG

1451 TGAGGAGCCC AAGGAGAGGC CTCCAGGAAC AGGAGGAGCT CTGCTTCCAT

1501 ATGTGGGGAG GAAAGGGTGG GCTCTGCCAG AGCAGCCTGT GAACTAATGC

1551 CCAGCATTCC TCAAGGTCAG CCAGACAAAA AGGAACTTAG GTCTTGGGCA

1601 GAGGAGGTGT AGCCTGGGGC AAAGTGATGA GATGTCCCTC CTTTCCTTGG

1651 CCTGATCCTT GTCTGCCTTC ACTTCCCTAG GCTGGGCTGA GGGCAACCTT

1701 GCCCCCCACC CAAGAAGCCC TGCCCTCCAG CCACAGCAGT CCACAGCAGC

1751 AGGGTTAAGA CTCAGCACAG GGCCAGCAGC AGCACAACCT TGACCAGAGC

1801 TTGGGTCCTA CCTGTCTACC TGGAGTGAAC AGTCCCTGAC TGCCTGTAGG

1851 CTGCGTGGAT GCGCAACACA CCCCCTCCTT CTCTGCTTTG GGTCCCTTCT

1901 CTCACCAAAT TCAAACTCCA TTCCCACCTA CCTAGAAAAT CACAGCCTCC

1951 TTATAATGCC TCCTCCTCCT GCCATTCTCT CTCCACCTAT CCATTAGCCT

2001 TCCTAACGTC CTACTCCTCA CACTGCTCTA CTGCTCAGAA ACCACCAAGA

2051 CTGTTGATGC CTTAGCCTTG CACTCCAGGG CCCTACCTGC ATTTCCCACA

2101 TGACTTTCTG GAAGCCTCCC AACTATTCTT GCTTTTCCCA GACAGCTCCC

2151 ACTCCCATGT CTCTGCTCAT TTAGTCCCGT CTTCCTCACC GCCCCAGCAG

2201 GGGAACGCTC AAGCCTGGTT GAAATGCTGC CTCTTCAGTG AAGTCATCCT

2251 CTTTCAGCTC TGGCCGCATT CTGCAGACTT CCTATCTTCG TGCTGTATGT

2301 TTTTTTTTC CCCCTTCACT CTAATGGACT GTTCCAGGGA AGGGATGGGG

2351 GCAGCAGCTG CTTCGGATCC ACACTGTATC TGTGTCATCC CCACATGGGT

2401 CCTCATAAAG GATTATTCAA TGGAGGCATC CTGACATCTG TTCATTTAGG

2451 CTTCAGTTCC ACTCCCAGGA ACTTTGCCTG TCCACGAGG GAGTATGGGA

2501 GAGATGGACT GCCACACAGA AGCTGAAGAC AACACCTGCT TCAGGGGAAC

Fig. 6A

```
2551  ACAGGCGCTT GAAAAAGAAA AGAGAGAACA GCCCATAATG CTCCCCGGGA
2601  GCAGAGGCCA CTAATGGAGA GTGGGAAGAG CCTGGAAAGA TGTGGCCTCA
2651  GGAAAAGGGA TGAGAGAAAG GAGGTGGTAT GGAAGACTCA GCAGGAACAA
2701  GGTAGGCTTC AAAGAGCCTA TATTCCTCTT TTTCCCACAC CGATCAAGTC
2751  AACTCAGTAC TCACGGGAGA AAAATAGACT TTATTTACAA GTAATAACAT
2801  TTAGAAAAGA TCCATCCCCG GCCCTTAAAA ACCTTCCCAT CACTCCAAAT
2851  CCCACCCCAG TGCAAGTCTG GGGAAGGTAG GGTGTGAGCT GCTGCTGAAG
2901  GCTGTCCCCC AACCCCACTC CTGAGACACA GGGCCCATCC GTCCTGGGAA
2951  AGAGCATCCT CTGGCAGGTG CTCCCACCAG GTCAGACCCA GTCCTGGACT
3001  TCAAGAGTGA GGGCCCCTGC TGGGCCCAGC CACCAGGACA GCAGGAACCA
3051  GGGCCTACTC CTCTTATGGT CCCTTCTAGA TCCAGAGGCT AAGAGGAAGA
3101  CTGGCCAGGC CCAAGGACCC AGCCATCAAA ACCAGCCTCA AATCTGGTTG
3151  TGATGGAGAA GTGACTTTGC TTTAAGAAAA AAGGAGGCAA GGTAGGGAGA
3201  GCGCCCACAC TGTCCATGCT CCAGGCCCCC TGGGCCAGCT CCGAGAAGGC
3251  GCCAGTGAAG GACCAGGGAC CAGGCCAGGG TGCGGGCAGG CATCACTGTC
3301  TCTAGGGGTT TGGCTACTGT TGGCCTGGGA GCTGAGAGAA GGCACTGAGA
3351  GGGACAGTAG GCGGAGGACC AGGTGACGGC AGCATCGGGG ACACAGGTGG
3401  GGCCACTCAC TGGTACTGGC CCTTTAGTGC TTTGCCTGAA AGAGACACAG
3451  TCACATGGCC AGATGAGAAC TTGCGATACT AGCCTGCACC CACTGGCTGG
3501  GAAGATCTCT TCCTGCTCCC ACGCCCTGT CTGGATCCCC TCCCTTGTGA
3551  GCCCCAGGGT TATCAGTTGC TGGCTGTGCC TGAGCAGCTC TGGGTGCTCT
3601  CCATGAGAAT GGGGCCATCT GTCTTCTCTC CTTGGAGAGG AGCTACCAGG
3651  ACAGGGACAC CTCTTACCCC ACACCCTCCA GCAGCCTGGC GTGGCCCCAT
3701  CTTGGATGCT ACTTGGTGGG GCGGTCTGGG GGGTGCCCAT GCTCTCATCG
3751  GGTTTCCCTC CCCCATCCTG CCAGTGCCTC TACCTTGCCC TTGGCTCGAG
3801  GGGTGGCACC AATGGCGGCA GCAGTGGCGG CGCTGGCTGT GGTGGTGGCA
```

Fig. 6B

3851 ATGCGCGGAG AACGGCGGGT TCCACTGCGA GTGTTGGGGG AAGCCTTGGA

3901 CAGGGCCTTC TTTGAGGCTC CCCGCCGCAG AAGGCTGTTC CCTAGCTTCT

3951 TGGGTGTGTT GAGGATGCTG AAGGCCATCG ACTGGCGCCG GTCAGCCTGC

4001 AAGGAAGGGC TGTCAGACCG GGAGACCCAA TGCTGCCTTC CCAGGCCAGC

4051 GTGCTGTGCC ACGCTGTACC AGCAAGGTCC CGCCAGGGCG TCGCTTCATC

4101 CCCCTTCAGC CCCAGCCTCA CCTGTTTAGT AGAAGCTGGA GCTGCTTTCT

4151 TCTGGGCCTC AGTAGTGCTC TGTTTGCGCC CTTCATGTCG GTCTCGGGGA

4201 GTCATGGGGC GTGGGAAACA GCTGGTGGCC TTCTTAGACT ATGGAGAAGA

4251 GGACAGTTAG GCAGACAGTA GCAAGAGGAG TCACATCTGA AGCCAGGTGT

4301 CTTGTCCTCT CAGAGCTGAG TGGACCTTGT AAGTCAACGT GCAACCTGCT

4351 CCCCTTCCCA ACTCTGGGCC AGATCCTTCC CTTCCCAACA GTTCCCATCC

4401 ATGGGTCAGG CCCTTGGAGA GAGGGAAAGA GAGGGGGAAG TGAGGGAAGG

4451 AGAGAGAAGG CTCCCTTTAG TCCTTGGTGA GCTGGGCCTG ACCTGAGCAC

4501 AGTGCTGGAG TAACACCCAG GAGCCACCGC GCCTACCTCA GGAGTTCCAG

4551 GGCCCTGGTG GGGCTCTAGG GAGACCCGTT TGCGCTGCTG CCGGGTGGTG

4601 ATGCCAGTGC CCTCGGCTAT CTGGATTGGC TGCATGCTGG CTCGGCGCAG

4651 GGTCTCTTGG GGGTCTCCAG TTTTCATCTC CTCATCTGTG ATGGTGCCCA

4701 GGCTCAGGGA AGGCTGCATG GGTGGAAGAG GTGGTCAGTG GACCATAGCT

4751 GTATGGAGAT GGAGGAGGAC CTGGGGCTGT TCCAGAACTC TACACTCGCC

4801 CGACACTTAT GGTCGGGACC CTTCCTGCCT ACGAGGTAGA AAGACACAAG

4851 CCTCCTTTCC TGTTCTGCTT TCTACCTAAG CCCTGGGCAA ATGGCACAAG

4901 CAGTGCAGTC CTGACCAGAT TCCTCTCTGA GCTCCTGCCT ACCCCAGGG

4951 ACTTCACCCC TGAGTGCCCT CCAGCTGTCT GTTCCACCTG AACATGAGA

5001 AGGTCACCCC TTCCCCTCTT CGGCCAGTCA GTGATCCAGG GCCCTAGTGC

5051 TCAGGCTAGA TCAGCAGGTG GGATTCCAAG GAAGGGCAGG GATGGGAGGC

5101 CCTGCACAGT GACCCCAGGC CTCACCCTGG ACTCCAGGGA TAGCAGGTCT

Fig. 6C

5151 TCAGATGTGG GGGGCACACT CGATTGCGCT GCTGCAGCTC TGCAATGCGG

5201 TTCCAGTCAT CCAGCTGCTC AGGCTCATCC TGGCAAGTGC CCATGTAGAA

5251 GCTGTTCCTT CCTGTGGAAG GCAGGGAAGT GGGAACAAAT GAGCCTGGAG

5301 TCGGCAGGTC ACCTCCTGGC CCTGGCATCT TGCCAGCCTT TGCTGCCACC

5351 TACCCCATAA ACTTGAAGCC CGGCACACCA GTCTGATTCA GTGCCGCAGG

5401 TGCAGGAGTA CGGCACACAG ACTATTTCTA TCCTAGGGGC TTGCTCACCA

5451 CCTTCTCCCT GGAGAGGGCA GAAGAGGTCA CACGCAGAGA CTGCTACTAC

5501 ATCTTATTCA CCTGCCAAGG CTTGGTGGCC AACACCCAGA GGAACAAATT

5551 AAGGACCGGG AATTAATTCC CAGGGGCTCC CTGGTGCCCA AGGACAAGA

5601 GCTTCCAAGA AGAGTCTGGC CAGCCTGGCC TTTCCAGCAG CCCATCACCG

5651 CCTGAGAACG GCATGGAGGA CTCCCCACAG CTAAGTGTCA CAATTGTGCT

5701 GGGAATCCCG GGCCCTTAAC TCTGGCTAAG AGTGCCCCCA ACACAGCCAG

5751 CCCCTAGATG GGCAGGTAAG GAAGGCCCTG AGGCTGCAGG AAGGAGGGGC

5801 AGGTGGAGCT GGATGGTAGC AAGGAGGCCA GCCTTGGATT TTTAAAAAGC

5851 TTTCCTCTTT TCCCTGTGCC ACGATCCACC TTCCAGTCTA ATTTTGGGGT

5901 ATAGTAAGTC CCTGTAGTCC CCTCACCTGG AGGGGCCCCA CTGGACACCC

5951 CGGCCTGGGA ACGACGAGCA GAACTGCGAG TGGTGGGGCG GTAGCCAGGC

6001 AAGCTGAGCA GGGCTGAGTT GCCATAATCG GGAGAACCCA GGCGAGCTAG

6051 AGACTGAGTA GAGGAGGTGG CTCGCAGGCT AGCCTGGGAA GCAGGAGCAG

6101 ACCGCGTGCT GTAGAACGAT GAGTTGGCGC TGTCTGGCTC TTCCACATCT

6151 AGCTTCTGGA AGACAGAGTG AATCTGTTGC AGTGTACAGT CCCTGGCACT

6201 GTACAGAAGC TTCCCATTCC CTTCCGAAGC CCTCAGATCC CACGGCACAT

6251 CCATGTATTC CCAACTGCTT TGCAAAGGTC CTTAAAGTGT GTGTCTGCAA

6301 GAAATGGGCC TTGTCGACAG AAGCCCTCAC AAGGTGGTGC TGATGTTGTC

6351 AAGACTCTTC TACGCATTTT TTTCATGGAG TCTATTCATA ATGCTTTGAG

6401 GTAGGGAATG CAGAGTGTTT ATCGGCCCAT TTGGAGATG AAGTGCAAAG

Fig. 6D

6451 AAATAAAGTG ACTAGCCCCA AATCACACTG CTAGGAAGTA TCAGAGCTGG

6501 GGCTAGGCCC CATGTCTCCT GACTAGTCAG GCTCATCCCA CAGCCTCTGC

6551 TGTCCCTCAG TCCAAACTTC CAGGGCCCTT ACCATGTTCC AGAACTTCCC

6601 CCAACTTCTT GGTAGCAGGG GGCACCCTAA ACACACAGGT CCCCCCTGCT

6651 GTACCAGGGG CCCCCTCTCC CCTCCTCCCA AACCTCCCCT TCAAGATGTG

6701 GAAACAAAGG CAAGGGCCTG CAGCCTGTCA GGCAGTCCAC TGGGCAGCAA

6751 CAATGCCTCT CAGCTGCATG GGGCATGCTG GGAGGCACAG GATGGGCTGC

6801 AGCTTCGCCA CGTTCTCTCC CTTCACCCTG CACAGGCTCA GTGCTACGCA

6851 TGGAGAGAAT GCTAGCCTTA GTCAGGAGGC AGGGATCTAA TCCTAGCCCT

6901 GCCTTTTTCT TCAGAAGTGC CCTTAACCAA GTCACTGCCC TTTTTAAGAC

6951 CTCTCAGCTT TCCCACTGTA ACATGGACTG GCTGCTCATC CCTCCCTGCT

7001 CCTGACTGAG TGCCCAGTGC AAAGATGCCC TTGAGAGGAA GTGGGAATTG

7051 CTGACCTGTC GAC (SEQ ID NO:5)

IL-18BPc; Protein

Length: 197 June 5, 1998 13:41 Type: P Check: 3353 ..

1 MRHNWTPDLS PLWVLLLCAH VVTLLVRATP VSQTTTAATA SVRSTKDPCP

51 SQPPVFPAAK QCPALEVTWP EVEVPLNGTL SLSCVACSRF PNFSILYWLG

101 NGSFIEHLPG RLWEGSTSRE RGSTGTQLCK ALVLEQLTPA LHSTNFSCVL

151 VDPEQVVQRH VVLAQLWVRS PRRGLQEQEE LCFHMWGGKG GLCQSSL (SEQ ID NO:6)

Fig. 6E

IL-18BPd; DNA

Length: 1360 June 19, 1998 14:55 Type: N Check: 8757 ..

```
   1 GCGGCCGCGT CGACCACGCA GCTAAACACA GCTAACTTGA GTCTTGGAGC
  51 TCCTAAAGGG AAGCTTCTGG AAAGGAAGGC TCTTCAGGAC CTCTTAGGAG
 101 CCAAAGAAGA GGACGTTGTC ACAGATAAAG AGCCAGGCTC ACCAGCTCCT
 151 GACGCATGCA TCATGACCAT GAGACACAAC TGGACACCAG ACCTCAGCCC
 201 TTTGTGGGTC CTGCTCCTGT GTGCCCACGT CGTCACTCTC CTGGTCAGAG
 251 CCACACCTGT CTCGCAGACC ACCACAGCTG CCACTGCCTC AGTTAGAAGC
 301 ACAAAGGACC CCTGCCCCTC CCAGCCCCCA GTGTTCCCAG CAGCTAAGCA
 351 GTGTCCAGCA TTGGAAGTGA CCTGGCCAGA GGTGGAAGTG CCACTGAATG
 401 GAACGCTGAG CTTATCCTGT GTGGCCTGCA GCCGCTTCCC CAACTTCAGC
 451 ATCCTCTACT GGCTGGGCAA TGGTTCCTTC ATTGAGCACC TCCCAGGCCG
 501 ACTGTGGGAG GGGAGCACCA GCCGGGAACG TGGGAGCACA GGCTGGGCTG
 551 AGGGCAACCT TGCCCCCCAC CCAAGAAGCC cTGCCCTCCA GCCACAGCAG
 601 TCCACAGCAG CAGGGTTAAG ACTCAGCACA GGGCCAGCAG CAGCACAACC
 651 TTGACCAGAG CTTGGGTCCT ACCTGTCTAC CTGGAGTGAA CAGTCCCTGA
 701 CTGCCTGTAG GCTGCGTGGA TGCGCAACAC ACCCCCTCCT TCTCTGCTTT
 751 GGGTCCCTTC TCTCACCAAA TTCAAaCTCC ATTCCCACCT ACCTAGAAAA
 801 TCACAGCCTC CTTATaATGC CTCCTCCTCC TGCCATTCTC TCTCCACCTA
 851 TCCATTAGCC TTCCTAACGT CCTACTCCTC ACACTGCTCT ACTGCTCAGA
 901 AACCACCAAG ACTGTTGATG CCTTAGCCTT GCACTCCAGG GCCCTACCTG
 951 CATTTCCCAC ATGACTTTCT GGAAGCCTCC CAACTATTCT TGCTTTTCCC
1001 AGACAGCTCC CACTCCCATG TCTCTGCTCA TTTAGTCCCG TCTTCCTCAC
1051 CGCCCCAGCA GGGGAACGCT CAAGCCTGGT TGAAATGCTG CCTCTTCAGT
1101 GAAGTCATCC TCTTTCAGCT CTGGCCGCAT TCTGCAGACT TCCTATCTTC
1151 GTGCTGTATG TTTTTTTTTT CCCCCTTCAC TCTAATGGAC TGTTCCAGGG
```

Fig. 7

1201 AAGGGATGGG GGCAGCAGCT GCTTCGGATC CACACTGTAT CTGTGTCATC

1251 CCCACATGGG TCCTCATAAA GGATTATTCA ATGGAGGCAT CCTGACATCT

1301 GTCCATTTAG CTTCAGTTC CACTCCCAGG AACTTTGCCT GTCCCACGAG

1351 GGAGTATGGG (SEQ ID NO:7)

IL-18BPd; protein

Length: 161  June 5, 1998 13:40  Type: P  Check: 2239 ..

1   MRHNWTPDLS PLWVLLLCAH VVTLLVRATP VSQTTTAATA SVRSTKDPCP

51  SQPPVFPAAK QCPALEVTWP EVEVPLNGTL SLSCVACSRF PNFSILYWLG

101 NGSFIEHLPG RLWEGSTSRE RGSTGWAEGN LAPHPRSPAL QPQQSTAAGL

151 RLSTGPAAAQ P (SEQ ID NO:8)

Fig. 7A

HuIL-18BP gene

Length: 7812  July 15, 1998 11:55  Type: N  Check: 7058 ..

```
  1 GTCGACGGTA CCCCCGGGAA AGATTTAATA CGACTCACTA TAGGGCGGGA
 51 CAGAATTGAT CTGTGAGAGA CTCATCTAGT TCATACCCTA GGTGACCCTG
101 GGGGTGGCAT GGGGGTAGAT TAGAGATCCC AGTCTGGTAT CCTCTGGAGA
151 GTAGGAGTCC CAGGAGCTGA AGGTTTCTGG CCACTGAACT TTGGCTAAAG
201 CAGAGGTGTC ACAGCTGCTC AAGATTCCCT GGTTAAAAAG TGAAAGTGAA
251 ATAGAGGGTC GGGGCAGTGC TTTCCCAGAA GGATTGCTCG GCATCCTGCC
301 CTTCCCAGAA GCAGCTCTGG TGCTGAAGAG AGCACTGCCT CCCTGTGTGA
351 CTGGGTGAGT CCATATTCTC TCTTTGGGTC TCAATTTTGC CTTCCCTAAT
401 GAAGGGGTAA GATTGGACTA GGTAAGCATC TTACAACCAT TTGTGGTCAT
451 GAGAGCTGGG GTGGGGAAGG ATTGTCACTT GACCCCCCCA GCTCTGTTTC
501 TAAGTGCTGA AAGAGCTCCA GGCTATGCTA CGGGAGGAGA AGCCAGCTAC
551 TGAGGAAAAG CCAGCTACTG AGAAAAAGCG GGAGTGGTTT ACCATTCTCC
601 TCCCCCACCT TTCACCAGAG AACAGGACGT TGTCACACAT AAAGAGCCAG
651 GCTCACCAGC TCCTGACGCA TGCATCATGA CCATGAGACA CAACTGGACA
701 CCAGGTAGGC CTTGGGGCTA CGCATGGGCA GGCGGGGTAG GGTGAGGTCT
751 ATGAACAGAA TGGAGCAATG GGCTAACCCG GAGCCTTCAC TCCAAGGCAA
801 ACCACCCAGC GCACCTGGTG CTGTTGCTTT AAGAACCTGG GCAGATATTG
851 TAGCTCTGGC TCCAGTCTAA AGCTTCTCTG TACTCTGTTC AATAAAGGGC
901 TAAGGGGTGG GTGCTGAGGG GTCCCTCTTC CCGCTCTGAT TCCCTGGCTA
951 GAACCCAGAC ATCTCTGGGC TGGAGTTACA TCCTTACCCG GGCAGCCCAC
1001 TCTGTCTCCA GAGCCGCTGA CCTGTAACTG TCCTTTCCTC AGACCTCAGC
1051 CCTTTGTGGG TCCTGCTCCT GTGTGCCCAC GTCGTCACTC TCCTGGTCAG
1101 AGCCACACCT GTCTCGCAGA CCACCACAGC TGCCACTGCC TCAGTTAGAA
1151 GCACAAAGGA CCCCTGCCCC TCCCAGCCCC CAGTGTTCCC AGCAGCTAAG
```

Fig. 8

1201 CAGTGTCCAG CATTGGAAGT GACCTGGCCA GAGGTGGAAG TGCCACTGAG

1251 TAAGAAGCAC AGTGGTGGAG GGTGGGCTAT GGGCACAGAG GTTCCCAGGG

1301 TCGGGTTGAC TCCTGAGCGC CAGTCCCCTT CTGCCCATGT ACCACCAGCT

1351 GAGCCAGCTG GGCTGAGCAC GCACCATTCT CCCTCCCCAA CCCAGTGTCA

1401 TGGGTGCAGG CTTGGCGCAG CTCCCAAGAT GCTCCCTATC AAATAGGACA

1451 GAGAACTCAA GACATAAGTA ATGGTCACAG GACCTCCCAG AGCCTTGGTT

1501 GCAGTGGACC CCAAGGCCAG CCCCTCCACC CAGAGCCTGC TGGCCTCTGG

1551 CCATCTCAGA GGAGCAGCAG CCATCCAGCA CTGCCTCTGT CACCTGGGCT

1601 CCCAAGTCAC CGAGGCTGGG CACTAGAAAA GGTCATCCTG AGGAGACAGG

1651 TTCAGAAGAG GATTCATCAC GTGAACCAAG GACCATTCCT CACATTCCCC

1701 GTGTTTAGGG CTAGGGCCTC TCGGAGACAA CTGCACTTCT GTAACGGACG

1751 TTCCCACCTA GGTGGTGTGC AGAGCAGTTC TCTAGGTTCC AGATGCATGG

1801 GGACTGGGGG GAGCTGGCAG AGAGGGCACA GCAGAGCAGG GTAGGGGAAG

1851 GGCCTGCTCT TCTGAAGAGC TAACTGCTGC CTGTGTCCCT AGATGGAACG

1901 CTGAGCTTAT CCTGTGTGGC CTGCAGCCGC TTCCCCAACT TCAGCATCCT

1951 CTACTGGCTG GGCAATGGTT CCTTCATTGA GCACCTCCCA GGCCGACTGT

2001 GGGAGGGGAG CACCAGGTGA GGGTCGCAGC AGCCAGGTGG GTGGGAAGGA

2051 AGCCTTCTGC GGCCTTCTCA TGACCTTTCC TTCCCTTCCG CTCCAGCCGG

2101 GAACGTGGGA GCACAGGTAC GCAGCTGTGC AAGGCCTTGG TGCTGGAGCA

2151 GCTGACCCCT GCCCTGCACA GCACCAACTT CTCCTGTGTG CTCGTGGACC

2201 CTGAACAGGT TGTCCAGCGT CACGTCGTCC TGGCCCAGCT CTGGGTGAGG

2251 AGCCCAAGGA GAGGCCTCCA GGAACAGGAG GAGCTCTGCT TCCATATGTG

2301 GGGAGGAAAG GGTGGGCTCT GCCAGAGCAG CCTGTGAACT AATGCCCAGC

2351 ATTCCTCAAG GTCAGCCAGA CAAAAAGGAA CTTAGGTCTT GGGCAGAGGA

2401 GGTGTAGCCT GGGGCAAAGT GATGAGATGT CCCTCCTTTC CTTGGCCTGA

2451 TCCTTGTCTG CCTTCACTTC CCTAGGCTGG GCTGAGGGCA ACCTTGCCCC

Fig. 8A

```
2501 CCACCCAAGA AGCCCTGCCC TCCAGCCACA GCAGTCCACA GCAGCAGGGT
2551 TAAGACTCAG CACAGGGCCA GCAGCAGCAC AACCTTGACC AGAGCTTGGG
2601 TCCTACCTGT CTACCTGGAG TGAACAGTCC CTGACTGCCT GTAGGCTGCG
2651 TGGATGCGCA ACACACCCCC TCCTTCTCTG CTTTGGGTCC CTTCTCTCAC
2701 CAAATTCAAA CTCCATTCCC ACCTACCTAG AAAATCACAG CCTCCTTATA
2751 ATGCCTCCTC CTCCTGCCAT TCTCTCTCCA CCTATCCATT AGCCTTCCTA
2801 ACGTCCTACT CCTCACACTG CTCTACTGCT CAGAAACCAC CAAGACTGTT
2851 GATGCCTTAG CCTTGCACTC CAGGGCCCTA CCTGCATTTC CCACATGACT
2901 TTCTGGAAGC CTCCCAACTA TTCTTGCTTT TCCAGACAG CTCCCACTCC
2951 CATGTCTCTG CTCATTTAGT CCCGTCTTCC TCACCGCCCC AGCAGGGGAA
3001 CGCTCAAGCC TGGTTGAAAT GCTGCCTCTT CAGTGAAGTC ATCCTCTTTC
3051 AGCTCTGGCC GCATTCTGCA GACTTCCTAT CTTCGTGCTG TATGTTTTTT
3101 TTTTCCCCCT TCACTCTAAT GGACTGTTCC AGGGAAGGGA TGGGGGCAGC
3151 AGCTGCTTCG GATCCACACT GTATCTGTGT CATCCCCACA TGGGTCCTCA
3201 TAAAGGATTA TTCAATGGAG GCATCCTGAC ATCTGTTCAT TTAGGCTTCA
3251 GTTCCACTCC CAGGAACTTT GCCTGTCCCA CGAGGGAGTA TGGGAGAGAT
3301 GGACTGCCAC ACAGAAGCTG AAGACAACAC CTGCTTCAGG GGAACACAGG
3351 CGCTTGAAAA AGAAAAGAGA GAACAGCCCA TAATGCTCCC CGGGAGCAGA
3401 GGCCACTAAT GGAGAGTGGG AAGAGCCTGG AAAGATGTGG CCTCAGGAAA
3451 AGGGATGAGA GAAAGGAGGT GGTATGGAAG ACTCAGCAGG AACAAGGTAG
3501 GCTTCAAAGA GCCTATATTC CTCTTTTTCC CACACCGATC AAGTCAACTC
3551 AGTACTCACG GGAGAAAAAT AGACTTTATT TACAAGTAAT AACATTTAGA
3601 AAAGATCCAT CCCCGGCCCT TAAAAACCTT CCCATCACTC CAAATCCCAC
3651 CCCAGTGCAA GTCTGGGGAA GGTAGGGTGT GAGCTGCTGC TGAAGGCTGT
3701 CCCCCAACCC CACTCCTGAG ACACAGGGCC CATCCGTCCT GGGAAAGAGC
3751 ATCCTCTGGC AGGTGCTCCC ACCAGGTCAG ACCCAGTCCT GGACTTCAAG
```

FIg. 8B

3801 AGTGAGGGCC CCTGCTGGGC CCAGCCACCA GGACAGCAGG AACCAGGGCC

3851 TACTCCTCTT ATGGTCCCTT CTAGATCCAG AGGCTAAGAG GAAGACTGGC

3901 CAGGCCCAAG GACCCAGCCA TCAAAACCAG CCTCAAATCT GGTTGTGATG

3951 GAGAAGTGAC TTTGCTTTAA GAAAAAAGGA GGCAAGGTAG GGAGAGCGCC

4001 CACACTGTCC ATGCTCCAGG CCCCCTGGGC CAGCTCCGAG AAGGCGCCAG

4051 TGAAGGACCA GGGACCAGGC CAGGGTGCGG GCAGGCATCA CTGTCTCTAG

4101 GGGTTTGGCT ACTGTTGGCC TGGGAGCTGA GAGAAGGCAC TGAGAGGGAC

4151 AGTAGGCGGA GGACCAGGTG ACGGCAGCAT CGGGGACACA GGTGGGGCCA

4201 CTCACTGGTA CTGGCCCTTT AGTGCTTTGC CTGAAAGAGA CACAGTCACA

4251 TGGCCAGATG AGAACTTGCG ATACTAGCCT GCACCCACTG GCTGGGAAGA

4301 TCTCTTCCTG CTCCCACGCC CCTGTCTGGA TCCCTCCCT TGTGAGCCCC

4351 AGGGTTATCA GTTGCTGGCT GTGCCTGAGC AGCTCTGGGT GCTCTCCATG

4401 AGAATGGGGC CATCTGTCTT CTCTCCTTGG AGAGGAGCTA CCAGGACAGG

4451 GACACCTCTT ACCCCACACC CTCCAGCAGC CTGGCGTGGC CCCATCTTGG

4501 ATGCTACTTG GTGGGGCGGT CTGGGGGGTG CCCATGCTCT CATCGGGTTT

4551 CCCTCCCCCA TCCTGCCAGT GCCTCTACCT GCCCTTGGC TCGAGGGGTG

4601 GCACCAATGG CGGCAGCAGT GGCGGCGCTG GCTGTGGTGG TGGCAATGCG

4651 CGGAGAACGG CGGGTTCCAC TGCGAGTGTT GGGGGAAGCC TTGGACAGGG

4701 CCTTCTTTGA GGCTCCCCGC CGCAGAAGGC TGTTCCCTAG CTTCTTGGGT

4751 GTGTTGAGGA TGCTGAAGGC CATCGACTGG CGCCGGTCAG CCTGCAAGGA

4801 AGGGCTGTCA GACCGGGAGA CCCAATGCTG CCTTCCCAGG CCAGCGTGCT

4851 GTGCCACGCT GTACCAGCAA GGTCCCGCCA GGGCGTCGCT TCATCCCCCT

4901 TCAGCCCCAG CCTCACCTGT TTAGTAGAAG CTGGAGCTGC TTTCTTCTGG

4951 GCCTCAGTAG TGCTCTGTTT GCGCCCTTCA TGTCGGTCTC GGGGAGTCAT

5001 GGGGCGTGGG AAACAGCTGG TGGCCTTCTT AGACTATGGA GAAGAGGACA

5051 GTTAGGCAGA CAGTAGCAAG AGGAGTCACA TCTGAAGCCA GGTGTCTTGT

Fig. 8C

```
5101 CCTCTCAGAG CTGAGTGGAC CTTGTAAGTC AACGTGCAAC CTGCTCCCCT
5151 TCCCAACTCT GGGCCAGATC CTTCCCTTCC CAACAGTTCC CATCCATGGG
5201 TCAGGCCCTT GGAGAGAGGG AAAGAGAGGG GGAAGTGAGG GAAGGAGAGA
5251 GAAGGCTCCC TTTAGTCCTT GGTGAGCTGG GCCTGACCTG AGCACAGTGC
5301 TGGAGTAACA CCCAGGAGCC ACCGCGCCTA CCTCAGGAGT TCCAGGGCCC
5351 TGGTGGGGCT CTAGGGAGAC CCGTTTGCGC TGCTGCCGGG TGGTGATGCC
5401 AGTGCCCTCG GCTATCTGGA TTGGCTGCAT GCTGGCTCGG CGCAGGGTCT
5451 CTTGGGGGTC TCCAGTTTTC ATCTCCTCAT CTGTGATGGT GCCCAGGCTC
5501 AGGGAAGGCT GCATGGGTGG AAGAGGTGGT CAGTGGACCA TAGCTGTATG
5551 GAGATGGAGG AGGACCTGGG GCTGTTCCAG AACTCTACAC TCGCCCGACA
5601 CTTATGGTCG GGACCCTTCC TGCCTACGAG GTAGAAAGAC ACAAGCCTCC
5651 TTTCCTGTTC TGCTTTCTAC CTAAGCCCTG GGCAAATGGC ACAAGCAGTG
5701 CAGTCCTGAC CAGATTCCTC TCTGAGCTCC TGCCTACCCC CAGGGACTTC
5751 ACCCCTGAGT GCCCTCCAGC TGTCTGTTCC ACCTGGAACA TGAGAAGGTC
5801 ACCCCTTCCC CTCTTCGGCC AGTCAGTGAT CCAGGGCCCT AGTGCTCAGG
5851 CTAGATCAGC AGGTGGGATT CCAAGGAAGG GCAGGGATGG GAGGCCCTGC
5901 ACAGTGACCC CAGGCCTCAC CCTGGACTCC AGGGATAGCA GGTCTTCAGA
5951 TGTGGGGGGC ACACTCGATT GCGCTGCTGC AGCTCTGCAA TGCGGTTCCA
6001 GTCATCCAGC TGCTCAGGCT CATCCTGGCA AGTGCCCATG TAGAAGCTGT
6051 TCCTTCCTGT GGAAGGCAGG GAAGTGGGAA CAAATGAGCC TGGAGTCGGC
6101 AGGTCACCTC CTGGCCCTGG CATCTTGCCA GCCTTTGCTG CCACCTACCC
6151 CATAAACTTG AAGCCCGGCA CACCAGTCTG ATTCAGTGCC GCAGGTGCAG
6201 GAGTACGGCA CACAGACTAT TTCTATCCTA GGGGCTTGCT CACCACCTTC
6251 TCCCTGGAGA GGGCAGAAGA GGTCACACGC AGAGACTGCT ACTACATCTT
6301 ATTCACCTGC CAAGGCTTGG TGGCCAACAC CCAGAGGAAC AAATTAAGGA
6351 CCGGGAATTA ATTCCCAGGG GCTCCCTGGT GCCCAAAGGA CAAGAGCTTC
```

Fig. 8D

6401 CAAGAAGAGT CTGGCCAGCC TGGCCTTTCC AGCAGCCCAT CACCGCCTGA

6451 GAAGGGCATG GAGGACTCCC CACAGCTAAG TGTCACAATT GTGCTGGGAA

6501 TCCCGGGCCC TTAACTCTGG CTAAGAGTGC CCCCAACACA GCCAGCCCCT

6551 AGATGGGCAG GTAAGGAAGG CCCTGAGGCT GCAGGAAGGA GGGGCAGGTG

6601 GAGCTGGATG GTAGCAAGGA GGCCAGCCTT GGATTTTTAA AAAGCTTTCC

6651 TCTTTTCCCT GTGCCACGAT CCACCTTCCA GTCTAATTTT GGGGTATAGT

6701 AAGTCCCTGT AGTCCCCTCA CCTGGAGGGG CCCCACTGGA CACCCCGGCC

6751 TGGGAACGAC GAGCAGAACT GCGAGTGGTG GGGCGGTAGC CAGGCAAGCT

6801 GAGCAGGGCT GAGTTGCCAT AATCGGGAGA ACCCAGGCGA GCTAGAGACT

6851 GAGTAGAGGA GGTGGCTCGC AGGCTAGCCT GGGAAGCAGG AGCAGACCGC

6901 GTGCTGTAGA ACGATGAGTT GGCGCTGTCT GGCTCTTCCA CATCTAGCTT

6951 CTGGAAGACA GAGTGAATCT GTTGCAGTGT ACAGTCCCTG GCACTGTACA

7001 GAAGCTTCCC ATTCCCTTCC GAAGCCCTCA GATCCCACGG CACATCCATG

7051 TATTCCCAAC TGCTTTGCAA AGGTCCTTAA AGTGTGTGTC TGCAAGAAAT

7101 GGGCCTTGTC GACAGAAGCC CTCACAAGGT GGTGCTGATG TTGTCAAGAC

7151 TCTTCTACGC ATTTTTTTCA TGGAGTCTAT TCATAATGCT TTGAGGTAGG

7201 GAATGCAGAG TGTTTATCGG CCCATTTTGG AGATGAAGTG CAAAGAAATA

7251 AAGTGACTAG CCCCAAATCA CACTGCTAGG AAGTATCAGA GCTGGGGCTA

7301 GGCCCCATGT CTCCTGACTA GTCAGGCTCA TCCCACAGCC TCTGCTGTCC

7351 CTCAGTCCAA ACTTCCAGGG CCCTTACCAT GTTCCAGAAC TTCCCCCAAC

7401 TTCTTGGTAG CAGGGGGCAC CCTAAACACA CAGGTCCCCC CTGCTGTACC

7451 AGGGGCCCCC TCTCCCCTCC TCCCAAACCT CCCCTTCAAG ATGTGGAAAC

7501 AAAGGCAAGG GCCTGCAGCC TGTCAGGCAG TCCACTGGGC AGCAACAATG

7551 CCTCTCAGCT GCATGGGGCA TGCTGGGAGG CACAGGATGG GCTGCAGCTT

7601 CGCCACGTTC TCTCCCTTCA CCCTGCACAG GCTCAGTGCT ACGCATGGAG

7651 AGAATGCTAG CCTTAGTCAG GAGGCAGGGA TCTAATCCTA GCCCTGCCTT

Fig. 8E

```
7701 TTTCTTCAGA AGTGCCCTTA ACCAAGTCAC TGCCCTTTTT AAGACCTCTC

7751 AGCTTTCCCA CTGTAACATG GACTGGCTGC TCATCCCTCC CTGCTCCTGA

7801 CTGAGTGCCC AG
```

(SEQ ID NO:9)

Fig. 8F

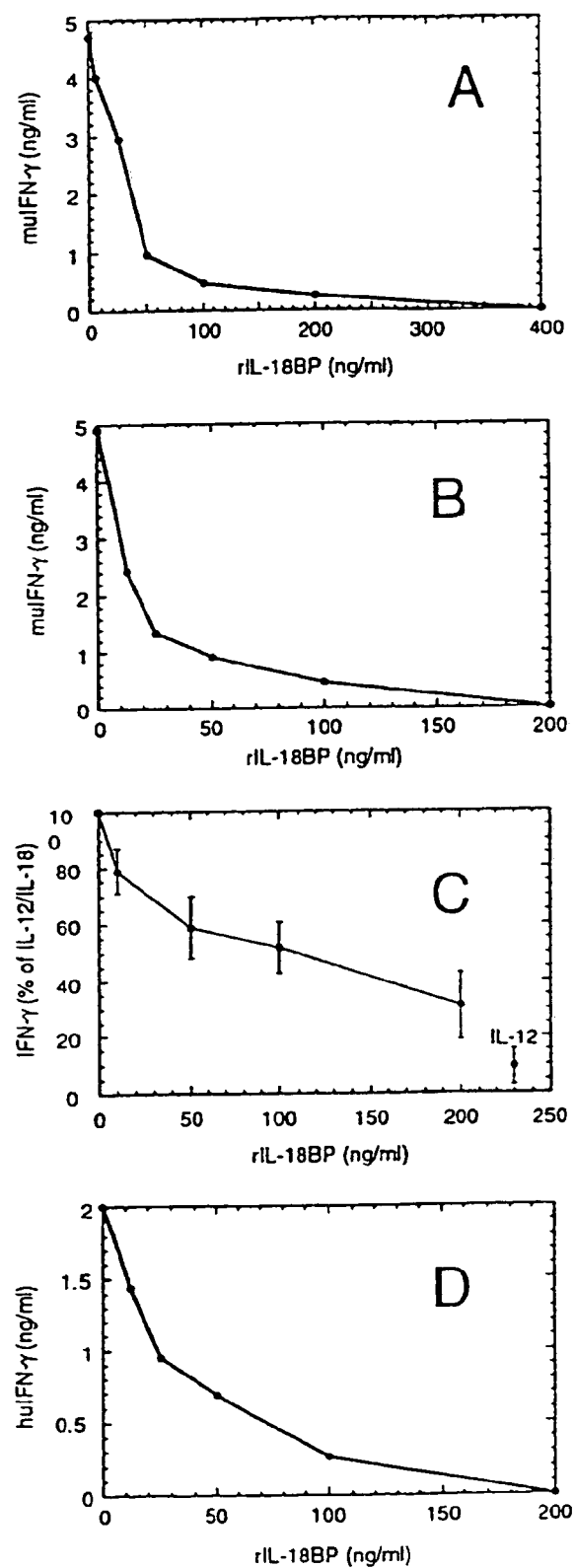
Fig. 9 A-D

SEQUENCE LISTING

<160> NUMBER OF SEQ ID NOS: 15

<210> SEQ ID NO 1
<211> LENGTH: 1348
<212> TYPE: DNA
<213> ORGANISM: Homo sapiens

<400> SEQUENCE: 1

```
gagaagagga cgttgtcaca gataaagagc caggctcacc agctcctgac gcatgcatca      60
tgaccatgag acacaactgg acaccagacc tcagcccttt gtgggtcctg ctcctgtgtg     120
cccacgtcgt cactctcctg gtcagagcca cacctgtctc gcagaccacc acagctgcca     180
ctgcctcagt tagaagcaca aaggacccct gcccctccca gccccagtg ttcccagcag      240
ctaagcagtg tccagcattg gaagtgacct ggccagaggt ggaagtgcca ctgaatggaa     300
cgctgagctt atcctgtgtg gcctgcagcc gcttccccaa cttcagcatc ctctactggc     360
tgggcaatgg ttccttcatt gagcacctcc caggccgact gtgggagggg agcaccagcc     420
gggaacgtgg gagcacaggt acgcagctgt gcaaggcctt ggtgctggag cagctgaccc     480
ctgccctgca cagcaccaac ttctcctgtg tgctcgtgga ccctgaacag gttgtccagc     540
gtcacgtcgt cctggcccag ctctgggctg ggctgagggc aaccttgccc ccacccaag      600
aagccctgcc ctccagccac agcagtccac agcagcaggg ttaagactca gcacagggcc     660
agcagcagca caaccttgac cagagcttgg gtcctacctg tctacctgga gtgaacagtc     720
cctgactgcc tgtaggctgc gtggatgcgc aacacacccc ctccttctct gctttgggtc     780
ccttctctca ccaaattcaa actccattcc cacctaccta gaaaatcaca gcctccttat     840
aatgcctcct cctcctgcca ttctctctcc acctatccat tagccttcct aacgtcctac     900
tcctcacact gctctactgc tcagaaacca ccaagactgt tgatgcctta gccttgcact     960
ccagggccct acctgcattt cccacatgac tttctggaag cctcccaact attcttgctt    1020
ttcccagaca gctcccactc ccatgtctct gctcatttag tcccgtcttc ctcaccgccc    1080
cagcagggga acgctcaagc ctggttgaaa tgctgcctct tcagtgaagt catcctcttt    1140
cagctctggc cgcattctgc agacttccta tcttcgtgct gtatgttttt tttttcccccc   1200
ttcactctaa tggactgttc cagggaaggg atgggggcac cagctgcttc ggatccacac    1260
tgtatctgtg tcatccccac atgggtcctc ataaggatt attcaatgga aaaaaaaaa     1320
aaaaaaaaa aaaaaaaaa aaaaaaaa                                       1348
```

<210> SEQ ID NO 2
<211> LENGTH: 192
<212> TYPE: PRT
<213> ORGANISM: Homo sapiens
<220> FEATURE:
<221> NAME/KEY: SIGNAL
<222> LOCATION: (1)..(28)

<400> SEQUENCE: 2

Met Arg His Asn Trp Thr Pro Asp Leu Ser Pro Leu Trp Val Leu Leu
 1               5                  10                  15

Leu Cys Ala His Val Val Thr Leu Leu Val Arg Ala Thr Pro Val Ser
             20                  25                  30

Gln Thr Thr Thr Ala Ala Thr Ala Ser Val Arg Ser Thr Lys Asp Pro
         35                  40                  45

Cys Pro Ser Gln Pro Pro Val Phe Pro Ala Ala Lys Gln Cys Pro Ala 50                  55                  60
Leu Glu Val Thr Trp Pro Glu Val Glu Val Pro Leu Asn Gly Thr Leu
 65                  70                  75                  80

Ser Leu Ser Cys Val Ala Cys Ser Arg Phe Pro Asn Phe Ser Ile Leu
                 85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Cys Lys Ala Leu Val Leu Glu Gln Leu Thr Pro Ala Leu His Ser Thr
    130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Pro Ser Ser His Ser Ser Pro Gln Gln Gln Gly
            180                 185                 190

<210> SEQ ID NO 3
<211> LENGTH: 1038
<212> TYPE: DNA
<213> ORGANISM: Homo sapiens

<400> SEQUENCE: 3
gagaagagga cgttgtcaca gataaagagc caggctcacc agctcctgac gcatgcatca      60
tgaccatgag acacaactgg acaccagacc tcagcccttt gtgggtcctg ctcctgtgtg     120
cccacgtcgt cactctcctg gtcagagcca cctgtctc gcagaccacc acagctgcca      180
ctgcctcagt tagaagcaca aaggacccct gcccctccca gccccagtg ttcccagcag      240 ctaagcagtg tccagcattg gaagtgacct ggccagaggt ggaagtgcca ctgagctggg     300
ctgagggcaa ccttgccccc cacccaagaa gccctgccct ccagccacag cagtccacag     360
cagcagggtt aagactcagc acagggccag cagcagcaca accttgacca gagcttgggt     420
cctacctgtc tacctggagt gaacagtccc tgactgcctg taggctgcgt ggatgcgcaa     480 cacacccct cctctctgc tttgggtccc ttctctcacc aaattcaaac tccattccca      540
cctacctaga aaatcacagc ctccttataa tgcctcctcc tcctgccatt ctctctccac     600
ctatccatta gccttcctaa cgtcctactc ctcacactgc tctactgctc agaaaccacc     660
aagactgttg atgccttagc cttgcactcc agggcctac ctgcatttcc cacatgactt      720
tctggaagcc tcccaactat tcttgctttt cccagacagc tcccactccc atgtctctgc     780
tcatttagtc ccgtcttcct caccgcccca gcagggaac gctcaagcct ggttgaaatg      840
ctgcctcttc agtgaagtca tcctctttca gctctggccg cattctgcag acttcctatc     900
ttcgtgctgt atgttttttt tttcccccttt cactctaatg gactgttcca gggaagggat    960 ggggcacca gctgcttcgg atccacactg tatctgtgtc atccccacat gggtcctcat     1020
aaaggattat tcaatgga                                                   1038

<210> SEQ ID NO 4
<211> LENGTH: 113
<212> TYPE: PRT
<213> ORGANISM: Homo sapiens
<220> FEATURE:
<221> NAME/KEY: SIGNAL
<222> LOCATION: (1)..(28)

-continued

```
<400> SEQUENCE: 4

Met Arg His Asn Trp Thr Pro Asp Leu Ser Pro Leu Trp Val Leu Leu
 1               5                  10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Ser Trp Ala Glu
 65                  70                  75                  80

Gly Asn Leu Ala Pro His Pro Arg Ser Pro Ala Leu Gln Pro Gln Gln
                85                  90                  95

Ser Thr Ala Ala Gly Leu Arg Leu Ser Thr Gly Pro Ala Ala Ala Gln
            100                 105                 110

Pro

<210> SEQ ID NO 5
<211> LENGTH: 7063
<212> TYPE: DNA
<213> ORGANISM: Homo sapiens

<400> SEQUENCE: 5
gaattcgcgg ccgcgtcgac gccagagggg ctaggatgag agacagaggg tgtgatggtg      60
ggtgctggga aatgtacccg accttggggc tggtggctgg gggagtgggt agcctgggaa     120
aggccaggat gtggacggac tggtatggca ttgagcctga agtggtccaa cttggggttc     180
cccagtgcct aggaaagttg tccccttgaa tgtcagtgtg aaggtgaagg aggaagcaga     240
tgcctgttca tatggaaaca aagacctggc tgtgaagagg ggaggcggac accaaagtcc     300
tgacacttgg gcgggacaga attgatctgt gagagactca tctagttcat accctaggtg     360
accctggggg tggcatgggg gtagattaga gatcccagtc tggtatcctc tggagagtag     420
gagtcccagg agctgaaggt ttctggccac tgaactttgg ctaaagcaga ggtgtcacag     480
ctgctcaaga ttccctggtt aaaaagtgaa agtgaaatag agggtcgggg cagtgctttc     540
ccagaaggat tgctcggcat cctgcccttc ccagaagcag ctctggtgct gaagagagca     600
ctgcctccct gtgtgactgg gtgagtccat attctctctt tgggtctcaa ttttgccttc     660
cctaatgaag gggtaagatt ggactaggta agcatcttac aaccatttgt ggtcatgaga     720 gctgggggtgg ggaaggattg tcacttgacc ccccagctc tgtttctaag tgctgaaaga     780
gctccaggct atgctacggg aggagaagcc agctactgag gaaagccag ctactgagaa     840 aaagcgggag tggtttacca ttctcctccc ccacctttca ccagagaaga ggacgttgtc     900
acacataaag agccaggctc accagctcct gacgcatgca tcatgaccat gagacacaac     960
tggacaccag acctcagccc tttgtgggtc ctgctcctgt gtgcccacgt cgtcactctc    1020
ctggtcagag ccacacctgt ctcgcagacc accacagctg ccactgcctc agttagaagc    1080
acaaaggacc cctgcccctc ccagcccca gtgttcccag cagctaagca gtgtccagca    1140
ttggaagtga cctggccaga ggtggaagtg ccactgaatg gaacgctgag cttatcctgt    1200
gtggcctgca gccgcttccc caacttcagc atcctctact ggctgggcaa tggttccttc    1260
attgagcacc tcccaggccg actgtgggag gggagcacca gccggaacg tgggagcaca    1320 ggtacgcagc tgtgcaaggc cttggtgctg agcagctga cccctgccct gcacagcacc    1380
```

```
aacttctcct gtgtgctcgt ggaccctgaa caggttgtcc agcgtcacgt cgtcctggcc    1440
cagctctggg tgaggagccc aaggagaggc ctccaggaac aggaggagct ctgcttccat    1500
atgtggggag gaaagggtgg gctctgccag agcagcctgt gaactaatgc ccagcattcc    1560
tcaaggtcag ccagacaaaa aggaacttag gtcttgggca gaggaggtgt agcctggggc    1620
aaagtgatga gatgtccctc ctttccttgg cctgatcctt gtctgccttc acttccctag    1680
gctgggctga gggcaacctt gccccccacc caagaagccc tgccctccag ccacagcagt    1740
ccacagcagc agggttaaga ctcagcacag ggccagcagc agcacaacct tgaccagagc    1800
ttgggtccta cctgtctacc tggagtgaac agtccctgac tgcctgtagg ctgcgtggat    1860
gcgcaacaca cccccctcctt ctctgctttg ggtcccttct ctcaccaaat tcaaactcca    1920
ttcccaccta cctagaaaat cacagcctcc ttataatgcc tcctcctcct gccattctct    1980
ctccacctat ccattagcct tcctaacgtc ctactcctca cactgctcta ctgctcagaa    2040
accaccaaga ctgttgatgc cttagccttg cactccaggg ccctacctgc atttcccaca    2100
tgactttctg gaagcctccc aactattctt gcttttccca gacagctccc actccatgt    2160 ctctgctcat ttagtcccgt cttcctcacc gccccagcag gggaacgctc aagcctggtt    2220
gaaatgctgc ctcttcagtg aagtcatcct cttttcagctc tggccgcatt ctgcagactt    2280
cctatcttcg tgctgtatgt ttttttttc cccttcact ctaatggact gttccaggga    2340
agggatgggg gcagcagctg cttcggatcc acactgtatc tgtgtcatcc ccacatgggt    2400
cctcataaag gattattcaa tggaggcatc ctgacatctg ttcatttagg cttcagttcc    2460
actcccagga actttgcctg tcccacgagg gagtatggga gagatggact gccacacaga    2520
agctgaagac aacacctgct tcaggggaac acaggcgctt gaaaagaaa agagagaaca    2580 gcccataatg ctccccggga gcagaggcca ctaatggaga gtgggaagag cctggaaaga    2640
tgtggcctca ggaaaaggga tgagagaaag gaggtggtat ggaagactca gcaggaacaa    2700
ggtaggcttc aaagagccta tattcctctt tttcccacac cgatcaagtc aactcagtac    2760
tcacgggaga aaaatagact ttatttacaa gtaataacat ttagaaaaga tccatccccg    2820
gcccttaaaa accttcccat cactccaaat cccacccag tgcaagtctg ggaaggtag    2880 ggtgtgagct gctgctgaag gctgtccccc aaccccactc ctgagacaca gggcccatcc    2940
gtcctgggaa agagcatcct ctggcaggtg ctcccaccag gtcagaccca gtcctggact    3000
tcaagagtga gggcccctgc tgggcccagc caccaggaca gcaggaacca gggcctactc    3060
ctcttatggt cccttctaga tccagaggct aagaggaaga ctggccaggc caaggaccc    3120 agccatcaaa accagcctca aatctggttg tgatggagaa gtgactttgc tttaagaaaa    3180
aaggaggcaa ggtagggaga gcgcccacac tgtccatgct ccaggccccc tgggccagct    3240
ccgagaaggc gccagtgaag gaccagggac caggccaggg tgcgggcagg catcactgtc    3300
tctaggggtt tggctactgt tggcctggga gctgagagaa ggcactgaga gggacagtag    3360
gcggaggacc aggtgacggc agcatcgggg acacaggtgg ggccactcac tggtactggc    3420
cctttagtgc tttgcctgaa agagacacag tcacatggcc agatgagaac ttgcgatact    3480
agcctgcacc cactggctgg gaagatctct tcctgctccc acgcccctgt ctggatcccc    3540
tcccttgtga gccccagggt tatcagttgc tggctgtgcc tgagcagctc tgggtgctct    3600
ccatgagaat ggggccatct gtcttctctc cttggagagg agctaccagg acagggacac    3660
ctcttacccc acaccctcca gcagcctggc gtggcccat cttggatgct acttggtggg    3720
gcggtctggg gggtgcccat gctctcatcg ggtttccctc cccatcctg ccagtgcctc    3780
```

```
taccttgccc ttggctcgag gggtggcacc aatggcggca gcagtggcgg cgctggctgt    3840
ggtggtggca atgcgcggag aacggcgggt tccactgcga gtgttggggg aagccttgga    3900
cagggccttc tttgaggctc cccgccgcag aaggctgttc cctagcttct tgggtgtgtt    3960
gaggatgctg aaggccatcg actggcgccg gtcagcctgc aaggaagggc tgtcagaccg    4020
ggagacccaa tgctgccttc ccaggccagc gtgctgtgcc acgctgtacc agcaaggtcc    4080
cgccagggcg tcgcttcatc cccttcagc cccagcctca cctgtttagt agaagctgga    4140
gctgctttct tctgggcctc agtagtgctc tgtttgcgcc cttcatgtcg gtctcgggga    4200 gtcatgggc gtgggaaaca gctggtggcc ttcttagact atggagaaga ggacagttag    4260
gcagacagta gcaagaggag tcacatctga agccaggtgt cttgtcctct cagagctgag    4320
tggaccttgt aagtcaacgt gcaacctgct ccccttccca actctgggcc agatccttcc    4380
cttcccaaca gttcccatcc atgggtcagg cccttggaga gagggaaaga gaggggaag    4440 tgagggaagg agagagaagg ctccctttag tccttggtga gctgggcctg acctgagcac    4500
agtgctggag taacccag gagccaccgc gcctacctca ggagttccag ggccctggtg    4560
gggctctagg gagacccgtt tgcgctgctg ccgggtggtg atgccagtgc cctcggctat    4620
ctggattggc tgcatgctgg ctcggcgcag ggtctcttgg gggtctccag ttttcatctc    4680
ctcatctgtg atggtgccca ggctcaggga aggctgcatg ggtggaagag gtggtcagtg    4740
gaccatagct gtatggagat ggaggaggac ctggggctgt tccagaactc tacactcgcc    4800
cgacacttat ggtcgggacc cttcctgcct acgaggtaga aagacacaag cctccttttcc    4860 tgttctgctt tctacctaag ccctgggcaa atggcacaag cagtgcagtc ctgaccagat    4920
tcctctctga gctcctgcct accccaggg acttcacccc tgagtgccct ccagctgtct    4980
gttccacctg gaacatgaga aggtcacccc ttcccctctt cggccagtca gtgatccagg    5040
gccctagtgc tcaggctaga tcagcaggtg ggattccaag gaagggcagg gatgggaggc    5100
cctgcacagt gaccccaggc ctcaccctgg actccaggga tagcaggtct tcagatgtgg    5160
ggggcacact cgattgcgct gctgcagctc tgcaatgcgg ttccagtcat ccagctgctc    5220
aggctcatcc tggcaagtgc ccatgtagaa gctgttcctt cctgtggaag cagggaagt    5280 gggaacaaat gagcctggag tcggcaggtc acctcctggc cctggcatct tgccagcctt    5340
tgctgccacc taccccataa acttgaagcc cggcacacca gtctgattca gtgccgcagg    5400
tgcaggagta cggcacacag actatttcta tcctaggggc ttgctcacca ccttctccct    5460
ggagagggca gaagaggtca cacgcagaga ctgctactac atcttattca cctgccaagg    5520
cttggtggcc aacacccaga ggaacaaatt aaggaccggg aattaattcc caggggctcc    5580
ctggtgccca aaggacaaga gcttccaaga agagtctggc cagcctggcc tttccagcag    5640
cccatcaccg cctgagaagg gcatggagga ctccccacag ctaagtgtca caattgtgct    5700
gggaatcccg ggcccttaac tctggctaag agtgccccca acacagccag ccctagatg    5760 ggcaggtaag gaaggccctg aggctgcagg aaggaggggc aggtggagct ggatggtagc    5820
aaggaggcca gccttggatt tttaaaaagc tttcctcttt tccctgtgcc acgatccacc    5880
ttccagtcta attttggggt atagtaagtc cctgtagtcc cctcacctgg aggggcccca    5940
ctggacaccc cggcctggga acgacgagca gaactgcgag tggtggggcg gtagccaggc    6000
aagctgagca gggctgagtt gccataatcg ggagaaccca ggcgagctag agactgagta    6060
gaggaggtgg ctcgcaggct agcctgggaa gcaggagcag accgcgtgct gtagaacgat    6120
```

-continued

```
gagttggcgc tgtctggctc ttccacatct agcttctgga agacagagtg aatctgttgc    6180
agtgtacagt ccctggcact gtacagaagc ttcccattcc cttccgaagc cctcagatcc    6240
cacggcacat ccatgtattc ccaactgctt tgcaaaggtc cttaaagtgt gtgtctgcaa    6300
gaaatgggcc ttgtcgacag aagccctcac aaggtggtgc tgatgttgtc aagactcttc    6360
tacgcatttt tttcatggag tctattcata atgctttgag gtaggaatg cagagtgttt     6420
atcggcccat tttggagatg aagtgcaaag aaataaagtg actagcccca aatcacactg    6480
ctaggaagta tcagagctgg ggctaggccc catgtctcct gactagtcag gctcatccca    6540
cagcctctgc tgtccctcag tccaaacttc cagggccctt accatgttcc agaacttccc    6600
ccaacttctt ggtagcaggg ggcaccctaa acacacaggt ccccctgct gtaccagggg      6660
cccctctcc cctcctccca aacctccct tcaagatgtg gaaacaaagg caagggcctg        6720
cagcctgtca ggcagtccac tgggcagcaa caatgcctct cagctgcatg ggcatgctg      6780
ggaggcacag gatgggctgc agcttcgcca cgttctctcc cttcaccctg cacaggctca    6840
gtgctacgca tggagagaat gctagcctta gtcaggaggc agggatctaa tcctagccct    6900
gccttttttct tcagaagtgc ccttaaccaa gtcactgccc tttttaagac ctctcagctt    6960
tcccactgta acatggactg gctgctcatc cctccctgct cctgactgag tgcccagtgc    7020
aaagatgccc ttgagaggaa gtgggaattg ctgacctgtc gac                       7063
```

<210> SEQ ID NO 6
<211> LENGTH: 197
<212> TYPE: PRT
<213> ORGANISM: Homo sapiens
<220> FEATURE:
<221> NAME/KEY: SIGNAL
<222> LOCATION: (1)..(28)

<400> SEQUENCE: 6

Met Arg His Asn Trp Thr Pro Asp Leu Ser Pro Leu Trp Val Leu Leu
 1               5                  10                  15

Leu Cys Ala His Val Val Thr Leu Leu Val Arg Ala Thr Pro Val Ser
            20                  25                  30

Gln Thr Thr Thr Ala Ala Thr Ala Ser Val Arg Ser Thr Lys Asp Pro
        35                  40                  45

Cys Pro Ser Gln Pro Pro Val Phe Pro Ala Ala Lys Gln Cys Pro Ala
    50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Cys Lys Ala Leu Val Leu Glu Gln Leu Thr Pro Ala Leu His Ser Thr
    130                 135                 140

Asn Phe Ser Cys Val Leu Val Asp Pro Glu Gln Val Val Gln Arg His
145                 150                 155                 160

Val Val Leu Ala Gln Leu Trp Val Arg Ser Pro Arg Arg Gly Leu Gln
                165                 170                 175

Glu Gln Glu Glu Leu Cys Phe His Met Trp Gly Gly Lys Gly Gly Leu
            180                 185                 190

Cys Gln Ser Ser Leu
        195

<210> SEQ ID NO 7
<211> LENGTH: 1360
<212> TYPE: DNA
<213> ORGANISM: Homo sapiens

<400> SEQUENCE: 7
gcggccgcgt cgaccacgca gctaaacaca gctaacttga gtcttggagc tcctaaaggg      60
aagcttctgg aaaggaaggc tcttcaggac ctcttaggag ccaaagaaga ggacgttgtc     120
acagataaag agccaggctc accagctcct gacgcatgca tcatgaccat gagacacaac     180
tggacaccag acctcagccc tttgtgggtc ctgctcctgt gtgcccacgt cgtcactctc     240
ctggtcagag ccacacctgt ctcgcagacc accacagctg ccactgcctc agttagaagc     300
acaaaggacc cctgcccctc ccagccccca gtgttcccag cagctaagca gtgtccagca     360
ttggaagtga cctggccaga ggtggaagtg ccactgaatg gaacgctgag cttatcctgt     420
gtggcctgca gccgcttccc caacttcagc atcctctact ggctgggcaa tggttccttc     480
attgagcacc tcccaggccg actgtgggag gggagcacca gccgggaacg tgggagcaca     540
ggctgggctg agggcaacct tgccccccac ccaagaagcc ctgccctcca gccacagcag     600
tccacagcag cagggttaag actcagcaca gggccagcag cagcacaacc ttgaccagag     660
cttgggtcct acctgtctac ctggagtgaa cagtccctga ctgcctgtag gctgcgtgga     720
tgcgcaacac acccctcct tctctgcttt gggtcccttc tctcaccaaa ttcaaactcc     780
attcccacct acctagaaaa tcacagcctc cttataatgc ctcctcctcc tgccattctc     840
tctccaccta tccattagcc ttcctaacgt cctactcctc acactgctct actgctcaga     900
aaccaccaag actgttgatg ccttagcctt gcactccagg gccctacctg catttcccac     960
atgactttct ggaagcctcc caactattct tgcttttccc agacagctcc cactcccatg    1020
tctctgctca tttagtcccg tcttcctcac cgccccagca ggggaacgct caagcctggt    1080
tgaaatgctg cctcttcagt gaagtcatcc tctttcagct ctggccgcat tctgcagact    1140
tcctatcttc gtgctgtatg tttttttttt cccccttcac tctaatggac tgttccaggg    1200
aagggatggg ggcagcagct gcttcggatc cacactgtat ctgtgtcatc cccacatggg    1260
tcctcataaa ggattattca atggaggcat cctgacatct gtccatttag gcttcagttc    1320
cactcccagg aactttgcct gtcccacgag ggagtatggg                          1360

<210> SEQ ID NO 8
<211> LENGTH: 161
<212> TYPE: PRT
<213> ORGANISM: Homo sapiens
<220> FEATURE:
<221> NAME/KEY: SIGNAL
<222> LOCATION: (1)..(28)

<400> SEQUENCE: 8

Met Arg His Asn Trp Thr Pro Asp Leu Ser Pro Leu Trp Val Leu Leu
  1               5                  10                  15

Leu Cys Ala His Val Val Thr Leu Leu Val Arg Ala Thr Pro Val Ser
                 20                  25                  30

Gln Thr Thr Thr Ala Ala Thr Ala Ser Val Arg Ser Thr Lys Asp Pro
             35                  40                  45

Cys Pro Ser Gln Pro Pro Val Phe Pro Ala Ala Lys Gln Cys Pro Ala
         50                  55                  60

```
Leu Glu Val Thr Trp Pro Glu Val Glu Val Pro Leu Asn Gly Thr Leu
 65                  70                  75                  80

Ser Leu Ser Cys Val Ala Cys Ser Arg Phe Pro Asn Phe Ser Ile Leu
                 85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Trp Ala Glu
        115                 120                 125

Gly Asn Leu Ala Pro His Pro Arg Ser Pro Ala Leu Gln Pro Gln Gln
    130                 135                 140

Ser Thr Ala Ala Gly Leu Arg Leu Ser Thr Gly Pro Ala Ala Ala Gln
145                 150                 155                 160

Pro

<210> SEQ ID NO 9
<211> LENGTH: 7812
<212> TYPE: DNA
<213> ORGANISM: Homo sapiens

<400> SEQUENCE: 9
gtcgacggta cccccgggaa agatttaata cgactcacta tagggcggga cagaattgat      60
ctgtgagaga ctcatctagt tcatacccta ggtgaccctg ggggtggcat ggggg tagat    120 tagagatccc agtctggtat cctctggaga gtaggagtcc caggagctga aggtttctgg    180
ccactgaact ttggctaaag cagaggtgtc acagctgctc aagattccct ggttaaaaag    240
tgaaagtgaa atagagggtc ggggcagtgc tttcccagaa ggattgctcg catcctgcc    300 cttcccagaa gcagctctgg tgctgaagag agcactgcct ccctgtgtga ctgggtgagt    360
ccatattctc tctttgggtc tcaatttttgc cttccctaat gaaggggtaa gattggacta    420
ggtaagcatc ttacaaccat ttgtggtcat gagagctggg gtggggaagg attgtcactt    480
gaccccccca gctctgtttc taagtgctga agagctcca ggctatgcta cgggaggaga    540
agccagctac tgaggaaaag ccagctactg agaaaaagcg ggagtggttt accattctcc    600
tcccccacct ttcaccagag aagaggacgt tgtcacacat aaagagccag gctcaccagc    660
tcctgacgca tgcatcatga ccatgagaca caactggaca ccaggtaggc cttgggcta     720 cgcatgggca ggcggggtag ggtgaggtct atgaacagaa tggagcaatg ggctaacccg    780
gagccttcac tccaaggcaa accacccagc gcacctggtg ctgttgcttt aagaacctgg    840
gcagatattg tagctctggc tccagtctaa agcttctctg tactctgttc aataaagggc    900
taaggggtgg gtgctgaggg gtccctcttc ccgctctgat tccctggcta gaacccagac    960
atctctgggc tggagttaca tccttacccg ggcagcccac tctgtctcca gagccgctga   1020
cctgtaactg tcctttcctc agacctcagc cctttgtggg tcctgctcct gtgtgcccac   1080
gtcgtcactc tcctggtcag agccacacct gtctcgcaga ccaccacagc tgccactgcc   1140
tcagttagaa gcacaaagga cccctgcccc tcccagcccc cagtgttccc agcagctaag   1200
cagtgtccag cattggaagt gacctggcca gaggtggaag tgccactgag taagaagcac   1260
agtggtggag ggtgggctat gggcacagag gttcccaggg tcgggttgac tcctgagcgc   1320
cagtcccctt ctgcccatgt accaccagct gagccagctg gctgagcac gcaccattct    1380 ccctccccaa cccagtgtca tgggtgcagg cttggcgcag ctcccaagat gctccctatc   1440
aaataggaca gagaactcaa gacataagta atggtcacag gacctcccag agccttggtt   1500
```

```
gcagtggacc ccaaggccag cccctccacc cagagcctgc tggcctctgg ccatctcaga   1560
ggagcagcag ccatccagca ctgcctctgt cacctgggct cccaagtcac cgaggctggg   1620
cactagaaaa ggtcatcctg aggagacagg ttcagaagag gattcatcac gtgaaccaag   1680
gaccattcct cacattcccc gtgtttaggg ctagggcctc tcggagacaa ctgcacttct   1740 gtaacgacg ttcccaccta ggtggtgtgc agagcagttc tctaggttcc agatgcatgg    1800
ggactggggg gagctggcag agagggcaca gcagagcagg gtaggggaag ggcctgctct   1860
tctgaagagc taactgctgc ctgtgtccct agatggaacg ctgagcttat cctgtgtggc   1920
ctgcagccgc ttccccaact tcagcatcct ctactggctg ggcaatggtt ccttcattga   1980
gcacctccca ggccgactgt gggaggggag caccaggtga gggtcgcagc agccaggtgg   2040
gtgggaagga agccttctgc ggccttctca tgacctttcc ttcccttccg ctccagccgg   2100
gaacgtggga gcacaggtac gcagctgtgc aaggccttgg tgctggagca gctgacccct   2160
gccctgcaca gcaccaactt ctcctgtgtg ctcgtggacc ctgaacaggt tgtccagcgt   2220
cacgtcgtcc tggcccagct ctgggtgagg agcccaagga gaggcctcca ggaacaggag   2280
gagctctgct tccatatgtg gggaggaaag ggtgggctct gccagagcag cctgtgaact   2340
aatgcccagc attcctcaag gtcagccaga caaaaaggaa cttaggtctt gggcagagga   2400
ggtgtagcct ggggcaaagt gatgagatgt ccctcctttc cttggcctga tccttgtctg   2460
ccttcacttc cctaggctgg gctgagggca accttgcccc ccacccaaga agccctgccc   2520
tccagccaca gcagtccaca gcagcagggt taagactcag cacagggcca gcagcagcac   2580
aaccttgacc agagcttggg tcctacctgt ctacctggag tgaacagtcc ctgactgcct   2640
gtaggctgcg tggatgcgca acacaccccc tccttctctg ctttgggtcc cttctctcac   2700
caaattcaaa ctccattccc acctacctag aaaatcacag cctccttata atgcctcctc   2760
ctcctgccat tctctctcca cctatccatt agccttccta acgtcctact cctcacactg   2820
ctctactgct cagaaaccac caagactgtt gatgccttag ccttgcactc cagggcccta   2880
cctgcatttc ccacatgact ttctggaagc ctcccaacta ttcttgcttt tcccagacag   2940
ctcccactcc catgtctctg ctcatttagt cccgtcttcc tcaccgcccc agcagggaa    3000 cgctcaagcc tggttgaaat gctgcctctt cagtgaagtc atcctctttc agctctggcc   3060
gcattctgca gacttcctat cttcgtgctg tatgttttt ttttcccct tcactctaat    3120 ggactgttcc agggaaggga tgggggcagc agctgcttcg gatccacact gtatctgtgt   3180
catccccaca tgggtcctca taaaggatta ttcaatggag gcatcctgac atctgttcat   3240
ttaggcttca gttccactcc caggaacttt gcctgtccca cgagggagta tgggagagat   3300
ggactgccac acagaagctg aagacaacac ctgcttcagg gaacacagg cgcttgaaaa    3360 agaaaagaga gaacagccca taatgctccc cgggagcaga ggccactaat ggagagtggg   3420
aagagcctgg aaagatgtgg cctcaggaaa gggatgaga gaaggaggt ggtatggaag     3480 actcagcagg aacaaggtag gcttcaaaga gcctatattc ctcttttcc cacaccgatc    3540 aagtcaactc agtactcacg ggagaaaaat agactttatt tacaagtaat aacatttaga   3600
aaagatccat cccggccct taaaaacctt cccatcactc caaatcccac cccagtgcaa    3660
gtctggggaa ggtagggtgt gagctgctgc tgaaggctgt cccccaaccc cactcctgag   3720
acacagggcc catccgtcct gggaaagagc atcctctggc aggtgctccc accaggtcag   3780
acccagtcct ggacttcaag agtgagggcc cctgctgggc ccagccacca ggacagcagg   3840
aaccagggcc tactcctctt atggtccctt ctagatccag aggctaagag gaagactggc   3900
```

```
caggcccaag gacccagcca tcaaaaccag cctcaaatct ggttgtgatg gagaagtgac    3960
tttgctttaa gaaaaaagga ggcaaggtag ggagagcgcc cacactgtcc atgctccagg    4020 cccctgggc cagctccgag aaggcgccag tgaaggacca gggaccaggc cagggtgcgg     4080
gcaggcatca ctgtctctag ggtttggct actgttggcc tgggagctga gagaaggcac    4140
tgagagggac agtaggcgga ggaccaggtg acggcagcat cggggacaca ggtggggcca    4200
ctcactggta ctggcccttt agtgctttgc ctgaaagaga cacagtcaca tggccagatg    4260
agaacttgcg atactagcct gcacccactg gctgggaaga tctcttcctg ctcccacgcc    4320
cctgtctgga tcccctccct tgtgagcccc agggttatca gttgctggct gtgcctgagc    4380
agctctgggt gctctccatg agaatggggc catctgtctt ctctccttgg agaggagcta    4440
ccaggacagg gacacctctt accccacacc ctccagcagc ctggcgtggc cccatcttgg    4500
atgctacttg gtggggcggt ctgggggtg cccatgctct catcgggttt ccctccccca    4560
tcctgccagt gcctctacct tgcccttggc tcgaggggtg gcaccaatgg cggcagcagt    4620
ggcggcgctg gctgtggtgg tggcaatgcg cggagaacgg cgggttccac tgcgagtgtt    4680
gggggaagcc ttggacaggg ccttctttga ggctccccgc cgcagaaggc tgttccctag    4740
cttcttgggt gtgttgagga tgctgaaggc catcgactgg cgccggtcag cctgcaagga    4800
agggctgtca gaccgggaga cccaatgctg ccttcccagg ccagcgtgct gtgccacgct    4860
gtaccagcaa ggtcccgcca gggcgtcgct tcatcccct tcagcccag cctcacctgt      4920 ttagtagaag ctggagctgc tttcttctgg gcctcagtag tgctctgttt gcgcccttca    4980
tgtcggtctc ggggagtcat ggggcgtggg aaacagctgg tggccttctt agactatgga    5040
gaagaggaca gttaggcaga cagtagcaag aggagtcaca tctgaagcca ggtgtcttgt    5100
cctctcagag ctgagtggac cttgtaagtc aacgtgcaac ctgctcccct tcccaactct    5160
gggccagatc cttcccttcc caacagttcc catccatggg tcaggccctt ggagagaggg    5220
aaagagaggg ggaagtgagg gaaggagaga gaaggctccc tttagtcctt ggtgagctgg    5280
gcctgacctg agcacagtgc tggagtaaca cccaggagcc accgcgccta cctcaggagt    5340
tccagggccc tggtggggct ctagggagac ccgtttgcgc tgctgccggg tggtgatgcc    5400
agtgccctcg gctatctgga ttggctgcat gctggctcgg cgcagggtct cttgggggtc    5460
tccagttttc atctcctcat ctgtgatggt gcccaggctc agggaaggct gcatgggtgg    5520
aagaggtggt cagtggacca tagctgtatg gagatggagg aggacctggg gctgttccag    5580
aactctacac tcgcccgaca cttatggtcg ggacccttcc tgcctacgag gtagaaagac    5640
acaagcctcc tttcctgttc tgcttctac ctaagccctg gcaaatggc acaagcagtg      5700 cagtcctgac cagattcctc tctgagctcc tgcctacccc cagggacttc acccctgagt    5760
gccctccagc tgtctgttcc acctggaaca tgagaaggtc acccctttccc ctcttcggcc    5820 agtcagtgat ccagggccct agtgctcagg ctagatcagc aggtgggatt ccaaggaagg    5880
gcagggatgg gaggccctgc acagtgaccc caggcctcac cctggactcc agggatagca    5940
ggtcttcaga tgtgggggc acactcgatt gcgctgctgc agctctgcaa tgcggttcca    6000
gtcatccagc tgctcaggct catcctggca agtgccatg tagaagctgt tccttcctgt     6060
ggaaggcagg gaagtgggaa caaatgagcc tggagtcggc aggtcacctc ctggccctgg    6120
catcttgcca gcctttgctg ccacctaccc cataaacttg aagcccggca caccagtctg    6180
attcagtgcc gcaggtgcag gagtacggca cacagactat ttctatccta ggggcttgct    6240
```

-continued

```
caccaccttc tccctggaga gggcagaaga ggtcacacgc agagactgct actacatctt    6300
attcacctgc caaggcttgg tggccaacac ccagaggaac aaattaagga ccgggaatta    6360
attcccaggg gctccctggt gcccaaagga caagagcttc aagaagagt  ctggccagcc    6420 tggcctttcc agcagcccat caccgcctga aagggcatg  gaggactccc cacagctaag    6480
tgtcacaatt gtgctgggaa tcccgggccc ttaactctgg ctaagagtgc ccccaacaca    6540
gccagcccct agatgggcag gtaaggaagg ccctgaggct gcaggaagga ggggcaggtg    6600
gagctggatg gtagcaagga ggccagcctt ggatttttaa aaagctttcc tcttttccct    6660
gtgccacgat ccaccttcca gtctaatttt ggggtatagt aagtccctgt agtcccctca    6720
cctggagggg ccccactgga caccccggcc tgggaacgac gagcagaact gcgagtggtg    6780
gggcggtagc caggcaagct gagcagggct gagttgccat aatcgggaga acccaggcga    6840
gctagagact gagtagagga ggtggctcgc aggctagcct gggaagcagg agcagaccgc    6900
gtgctgtaga acgatgagtt ggcgctgtct ggctcttcca catctagctt ctggaagaca    6960
gagtgaatct gttgcagtgt acagtccctg gcactgtaca gaagcttccc attcccttcc    7020
gaagccctca gatcccacgg cacatccatg tattcccaac tgctttgcaa aggtccttaa    7080
agtgtgtgtc tgcaagaaat gggccttgtc gacagaagcc ctcacaaggt ggtgctgatg    7140
ttgtcaagac tcttctacgc attttttca  tggagtctat tcataatgct ttgaggtagg    7200
gaatgcagag tgtttatcgg cccatttTGG agatgaagtg caaagaaata aagtgactag    7260 ccccaaaatca cactgctagg aagtatcaga gctggggcta ggcccatgt  ctcctgacta    7320 gtcaggctca tcccacagcc tctgctgtcc ctcagtccaa acttccaggg cccttaccat    7380
gttccagaac ttcccccaac ttcttggtag caggggcac  cctaaacaca caggtccccc    7440
ctgctgtacc aggggccccc tctcccctcc tcccaaacct cccttcaag  atgtggaaac    7500 aaaggcaagg gcctgcagcc tgtcaggcag tccactgggc agcaacaatg cctctcagct    7560
gcatggggca tgctgggagg cacaggatgg gctgcagctt cgccacgttc tctcccttca    7620
ccctgcacag gctcagtgct acgcatggag agaatgctag ccttagtcag gaggcaggga    7680
tctaatccta gccctgcctt tttcttcaga agtgcccta  accaagtcac tgccctttt    7740 aagacctctc agcttcccca ctgtaacatg gactggctgc tcatccctcc ctgctcctga    7800
ctgagtgccc ag                                                       7812
```

<210> SEQ ID NO 10
<211> LENGTH: 40
<212> TYPE: PRT
<213> ORGANISM: Homo sapiens
<220> FEATURE:
<221> NAME/KEY: variant
<222> LOCATION: (1) to (40)
<223> OTHER INFORMATION: wherein Xaa is any amino acid as defined in the
      specification

<400> SEQUENCE: 10

Thr Pro Val Ser Gln Xaa Xaa Xaa Ala Ala Xaa Ala Ser Val Arg Ser
 1               5                  10                  15

Thr Lys Asp Pro Cys Pro Ser Gln Pro Pro Val Phe Pro Ala Ala Lys
            20                  25                  30

Gln Cys Pro Ala Leu Glu Val Thr
        35                  40

<210> SEQ ID NO 11
<211> LENGTH: 12

```
<212> TYPE: PRT
<213> ORGANISM: Artificial Sequence
<220> FEATURE:
<223> OTHER INFORMATION: Description of Artificial Sequence: Chemically
      synthesized
<220> FEATURE:
<221> NAME/KEY: variant
<222> LOCATION: (1) to (12)
<223> OTHER INFORMATION: wherein Xaa is any amino acid as defined in the
      specification

<400> SEQUENCE: 11

Thr Pro Val Ser Gln Gln Xaa Xaa Xaa Ala Ala Ala
 1               5                  10

<210> SEQ ID NO 12
<211> LENGTH: 50
<212> TYPE: PRT
<213> ORGANISM: Artificial Sequence
<220> FEATURE:
<223> OTHER INFORMATION: Description of Artificial Sequence: Chemically
      synthesized
<220> FEATURE:
<221> NAME/KEY: variant
<222> LOCATION: (1) to (50)
<223> OTHER INFORMATION: wherein Xaa is any amino acid as defined in the
      specification

<400> SEQUENCE: 12

Val Thr Leu Leu Val Arg Ala Thr Xaa Val Xaa Gln Thr Thr Thr Ala
 1               5                  10                  15

Ala Thr Ala Ser Val Arg Ser Thr Lys Asp Pro Cys Pro Ser Gln Pro
             20                  25                  30

Pro Val Phe Pro Ala Ala Lys Gln Cys Pro Ala Leu Glu Val Thr Trp
         35                  40                  45

Pro Glu
     50

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Chemically
      synthesized
<220> FEATURE:
<221> NAME/KEY: variant
<222> LOCATION: (1) to (12)
<223> OTHER INFORMATION: wherein Xaa is any amino acid as defined in the
      specification

<400> SEQUENCE: 13

Ala Xaa Tyr Xaa Arg Ile Pro Ala Xaa Ala Ile Ala
 1               5                  10

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Chemically
      synthesized

<400> SEQUENCE: 14
tatatctaga gccaccatga gacacaactg gacacca                              37

<210> SEQ ID NO 15
<211> LENGTH: 50
```

-continued

```
<212> TYPE: DNA
<213> ORGANISM: Artificial Sequence
<220> FEATURE:
<223> OTHER INFORMATION: Description of Artificial Sequence: Chemically
      synthesized

<400> SEQUENCE: 15
atatctagat taatgatgat gatgatgatg accctgctgc tgtggactgc            50
```

INTERLEUKIN-18 BINDING PROTEINS, THEIR PREPARATION AND USE

RELATED APPLICATIONS

This application is a continuation of U.S. Ser. No. 10/434, 583, filed May 8, 2003, now issued U.S. Pat. No. 7,101,689 which is a divisional application of U.S. Ser. No. 09/485,632 file Oct. 12, 2000, now issued U.S. Pat. No. 6,605,250 which is a national stage application, filed under 35 U.S.C. §371, of International Application No. of PCT Application IL98/00379, filed Aug. 13, 1998 which claims the priority to Israel application 125463, filed Jul. 22, 1998, Israel application 122134, filed Nov. 6, 1997, Israel application 121860, filed Sep. 29, 1997 Israel application 121639, filed Aug. 27, 1997, and Israel application 121554, filed Aug. 14, 1997. Each of these applications is incorporated by reference in its entirety.

FIELD OF THE INVENTION

The present invention relates to interleukin-18 (IL-18) binding protein, hereinafter IL-18BP, capable of binding IL-18. More particularly, this invention relates to a soluble IL-18BP obtainable from body fluids, to soluble IL-18BPs obtainable by expression of suitable DNA vectors in host cells, to virus-encoded homologues of IL-18BP obtainable by expression of suitable DNA vectors in host cells, to vectors expressing the various IL-18BPs, to vectors useful for expression of IL-18BP in humans and other mammals, to antibodies against IL-18BPs, to therapeutic use of said IL-18BPs by modulating and/or blocking IL-18 activity, to therapeutic use of said expression vectors in modulating and/or blocking IL-18 activity and to use of the antibodies.

BACKGROUND OF THE INVENTION

In 1989, an endotoxin-induced serum activity that induced interferon-γ (IFN-γ) obtained from mouse spleen cells was described (27). This serum activity functioned not as a direct inducer of IFN-γ but rather as a co-stimulant together with IL-2 or mitogens. An attempt to purify the activity from post-endotoxin mouse serum revealed an apparently homogeneous 50-55 kDa protein (26). Since other cytokines can act as co-stimulants for IFN-γ production, the failure of neutralizing antibodies to IL-1, IL-4, IL-5, IL-6, or TNF to neutralize the serum activity suggested it was a distinct factor. In 1995, the same scientists demonstrated that the endotoxin-induced co-stimulant for IFN-γ production was present in extracts of livers from mice preconditioned with *P. acnes* (31). In this model, the hepatic macrophage population (Kupffer cells) expand and in these mice, a low dose of bacterial lipopolysaccharide (LPS), which in non-preconditioned mice is not lethal, becomes lethal. The factor, named IFN-γ-inducing factor (IGIF) and later designated interleukin-18 (IL-18), was purified to homogeneity from 1,200 grams of *P. acnes*-treated mouse livers. Degenerate oligonucleotides derived from amino acid sequences of purified IL-18 were used to clone a murine IL-18 cDNA (31). IL-18 is an 18-19 kDa protein of 157 amino acids, which has no obvious similarities to any peptide in the databases. Messenger RNAs for IL-18 and interleukin-12 (IL-12) are readily detected in Kupffer cells and activated macrophages. Recombinant IL-18 induces IFN-gamma more potently than does IL-12, apparently through a separate pathway (31). Similar to the endotoxin-induced serum activity, IL-18 does not induce IFN-γ by itself, but functions primarily as a co-stimulant with mitogens or IL-2. IL-18 enhances T cell proliferation, apparently through an IL-2-dependent pathway, and enhances Th1 cytokine production in vitro and exhibits synergism when combined with IL-12 in terms of enhanced IFN-γ production (24).

Neutralizing antibodies to mouse IL-18 were shown to prevent the lethality of low-dose LPS in *P. acnes* pre-conditioned mice. Others had reported the importance of IFN-γ as a mediator of LPS lethality in pre-conditioned mice. For example, neutralizing anti-IFN-γ antibodies protected mice against Shwartzman-like shock (16), and galactosamine-treated mice deficient in the IFN-γ receptor were resistant to LPS-induced death (7). Hence, it was not unexpected that neutralizing antibodies to murine IL-18 protected *P. acnes*-preconditioned mice against lethal LPS (31). Anti-murine IL-18 treatment also protected surviving mice against severe hepatic cytotoxicity.

After the murine form was cloned, the human cDNA sequence for IL-18 was reported in 1996 (38). Recombinant human IL-18 exhibits natural IL-18 activity (38). Human recombinant IL-18 is without direct IFN-γ-inducing activity on human T-cells, but acts as a co-stimulant for production of IFN-γ and other T-helper cell-1 (Th1) cytokines (38). To date, IL-18 is thought of primarily as a co-stimulant for Th1 cytokine production (IFN-γ, IL-2 and granulocyte-macrophage colony stimulating factor) (20) and also as a co-stimulant for FAS ligand-mediated cytotoxicity of murine natural killer cell clones (37).

By cloning IL-18 from affected tissues and studying IL-18 gene expression, a close association of this cytokine with an autoimmune disease was found. The non-obese diabetic (NOD) mouse spontaneously develops autoimmune insulitis and diabetes, which can be accelerated and synchronized by a single injection of cyclophosphamide. IL-18 mRNA was demonstrated by reverse transcriptase PCR in NOD mouse pancreas during early stages of insulitis. Levels of IL-18 mRNA increased rapidly after cyclophosphamide treatment and preceded a rise in IFN-γ mRNA, and subsequently diabetes. Interestingly, these kinetics mimic that of IL-12-p40 mRNA, resulting in a close correlation of individual mRNA levels. Cloning of the IL-18 cDNA from pancreas RNA followed by sequencing revealed identity with the IL-18 sequence cloned from Kupffer cells and in vivo pre-activated macrophages. Also NOD mouse macrophages responded to cyclophosphamide with IL-18 gene expression while macrophages from Balb/c mice treated in parallel did not. Therefore, IL-18 expression is abnormally regulated in autoimmune NOD mice and closely associated with diabetes development (32).

IL-18 plays a potential role in immunoregulation or in inflammation by augmenting the functional activity of Fas ligand on Th1 cells (10). IL-18 is also expressed in the adrenal cortex and therefore might be a secreted neuro-immuno-modulator, playing an important role in orchestrating the immune system following a stressful experience (9).

In vivo, IL-18 is formed by cleavage of pro-IL-18, and its endogenous activity appears to account for IFN-γ production in *P. acnes* and LPS-mediated lethality. Because of its activity, blocking the biological activity of IL-18 in human disease is a therapeutic strategy in many diseases. This can be accomplished using soluble receptors or blocking antibodies to the cell-bound IL-18 receptor.

Cytokine binding proteins (soluble cytokine receptors) correspond to the extracellular ligand binding domains of their respective cell surface cytokine receptors. They are derived either by alternative splicing of a pre-mRNA, common to the cell surface receptor, or by proteolytic cleavage of the cell surface receptor. Such soluble receptors have been described in the past, including among others, the soluble receptors of IL-6 and IFN-γ (30), TNF (11, 12), IL-1 and IL-4 (21), IFN-α/β (28, 29) and others. One cytokine-binding protein, named osteoprotegerin (OPG, also known as osteoclast inhibitory factor—OCIF), a member of the TNFR/Fas family, appears to be the first example of a soluble receptor that exists only as a secreted protein (1, 34, 39).

SUMMARY OF THE INVENTION

The present invention provides IL-18 binding proteins (IL-18BPs) and virally encoded IL-18BP homologues (hereinafter, viral IL-18BPs), and fused proteins, muteins, functional derivatives, active fragments and circularly permutated derivatives thereof, capable of binding to IL-18. The invention also provides a process for isolating IL-18BPs from human fluids, and a process to obtain them by recombinant means. The invention also provides expression vectors of IL-18BPs, suitable for expression of IL-18BP in humans and other mammals. Specific IL-18BPs, virally encoded IL-18BP homologues, fused proteins, muteins, functional derivatives, active fragments and circularly permutated derivatives thereof of the present invention are useful for modulating and/or blocking the biological activities of IL-18.

Replicable expression vehicles containing DNAs suitable for expression of the various IL-18BPs in host cells, host cells transformed herewith and proteins and polypeptides produced by expression of such hosts are also provided.

The invention further provides pharmaceutical compositions consisting of suitable vehicles and IL-18BPs, or viral IL-18BPs, or vectors for expressing same in humans and other mammals, for the treatment of diseases or conditions which require modulation or blocking of IL-18 activity.

The invention further provides antibodies to the IL-18BPs and the viral IL-18BPs, suitable for affinity purification and immunoassays of same.

DESCRIPTION OF THE FIGURES

FIGS. 3A-3E show inhibition of IL-18-induced production of IFN-γ by IL-18BP (A) Mouse splenocytes were stimulated (24 hr, 37° C.) with the indicated combinations of LPS (1 μg/ml) and human IL-18 (5 ng/ml), added either directly, or after pre-mixing (1 h, 37° C.) with urinary IL-18BP. The level of muIFN-γ in the culture was determined after 24 hr.

Figure 1:
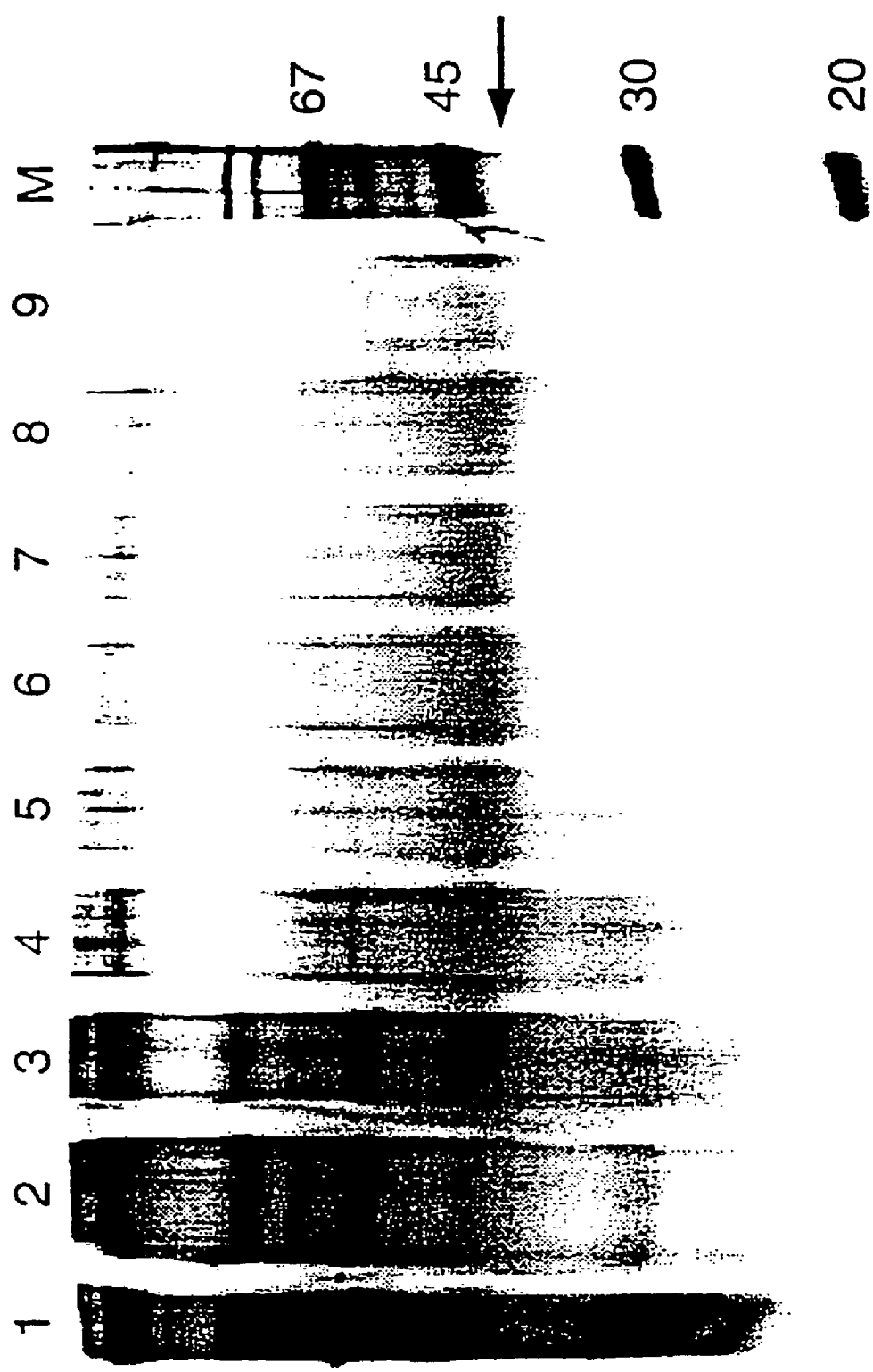
FIG. 1 shows SDS-PAGE (sodium dodecyl sulfate polyacrylamide gel electrophoresis) of ligand affinity purified IL-18 binding protein. Crude urinary proteins (concentrated by ultrafiltration of 500 L normal human urine) were loaded on an IL-18-agarose column. The column was washed and bound proteins eluted at pH 2.2. Eluted fractions were neutralized and aliquots were analyzed by SDS-PAGE (10% acrylamide) under non-reducing conditions and silver staining. The lanes are: 1: crude urinary proteins (1.5 μg, loaded on the gel); 2-9: elutions 1-8, respectively, from the IL-18-agarose column; 10: molecular weight markers, in kD, as indicated on the right side. An arrow indicates the band corresponding to IL-18BP.

(B) Mouse splenocytes were incubated (24 h) with LPS (1 μg/ml) together with murine IL-18 (10 ng/ml) pre-mixed (1 h, 37° C.) with increasing concentrations of human IL-18BP.

(C) Mouse splenocytes were incubated (24 h) with LPS (10 μg/ml) together with increasing concentrations of human IL-18BP.

(D) Mouse splenocytes were incubated (24 h) with Con A (I % g/ml), together with increasing concentrations of human IL-18BP.

(E) Human KG-1 cells were stimulated with TNF-α (20 ng/ml) and huIL-18 (25 ng/ml), added either alone, or after pre-mixing (1 h, 37° C.) with urinary IL-18BP.

FIGS. 4 and 4A show the sequence of human IL-18BPa cDNA and protein. The signal peptide is underlined.

FIGS. 5 and 5A show the sequence of human IL-18BPb cDNA and protein. The signal peptide is underlined.

FIGS. 6-6E show the sequence of human IL-18BPc cDNA and protein. The signal peptide is underlined.

FIGS. 7 and 7A show the sequence of human IL-18BPd cDNA and protein. The signal peptide is underlined.

FIGS. 8-8F show the sequence of human IL-18BP gene. The sequence of a human genomic clone (7.1 kb) was determined and compared with that of the various cDNA clones isolated from 3 cDNA libraries. the common translation start codon is nucleotides 683-685. The NuMA1 gene is located on the negative strand, from nucleotide 3578 to the end.

FIGS. 9A-9D show the effect of recombinant IL-18BP on human and mouse IL-18 activity.

His$_6$-tagged IL-18BPa was transiently expressed in COS7 cells and purified.

(A) Human IL-18 (5 ng/ml) was pre-mixed with either His$_6$-tagged-IL-18BPa or RPMI and added to mouse spleen cells together with LPS (1 μg/ml). IFN-γ production was measured after 24 h.

(B) Mouse IL-18 (10 ng/ml) was pre-mixed with either His$_6$-tagged-IL-18BPa or RPMI and added to mouse spleen cells together with LPS (1 μg/ml). IFN-γ production was measured after 24 h.

(C) Human IL-18 (25 ng/ml) was pre-mixed with either COS7—IL-18BPa or RPMI and added to Human PBMC in the presence of IL-12 (10 ng/ml).

(D) Human IL-18 (25 ng/ml) was pre-mixed with either COS7—IL-18BPa or RPMI and added to Human KG-1 cells in the presence of TNF-α (20 ng/ml).

DETAILED DESCRIPTION OF THE INVENTION

The present invention relates to various IL-18BPs and viral IL-18BPs which bind to IL-18. Such IL-18BPs may be capable of modulating and/or blocking the biological activities of IL-18. The term, "IL-18BPs and viral IL-18BPs," includes the mature protein (without the signal sequence), the protein comprising signal sequences, muteins of IL-18BPs and viral IL-18BPs, derivatives of IL-18BPs and viral IL-18BPs and truncated forms of IL-18BPs and viral IL-18BPs and salts thereof.

The invention further relates to replicable expression vehicles, suitable for expression of various IL-18BPs or viral IL-18BPs in host cells and host bacteria. The invention further relates to expression vectors, suitable for expression of various IL-18BPs or viral IL-18BPs in humans and in other mammals.

The invention further relates to DNAs coding for various IL-18BPs, viral IL-18BPs, muteins, fused proteins, functional derivatives, active fractions and mixtures thereof. Said DNA may be a genomic DNA, a cDNA, a synthetic DNA, a PCR product or combinations thereof. These DNAs may be inserted into replicable expression vehicles for expression of various IL-18BPs and viral IL-18BPs in host cells, according to the invention. DNAs capable of hybridizing to the above DNAs under stringent conditions and encoding proteins or polypeptides which are also capable of binding IL-18 are also included in the present invention.

One such DNA encodes an IL-18BP including the amino acid sequence of SEQ ID NO:10 and provided with a stop codon at its 3' end.

The expression vectors, suitable for expression of various IL-18BPs or viral IL-18BPs in humans and in other mammals, i.e. for gene therapy, may be viral vectors or other types of vectors in which an IL-18BP gene or an IL-18BP cDNA or a DNA encoding a viral IL-18BP was inserted in a way that enables efficient expression of an IL-18BP or a viral IL-18BP in humans and other mammals. DNA molecules hybridizing to the above DNAs under stringent conditions and encoding proteins or polypeptides which are capable of binding IL-18, are also included in the present invention.

Isolation of IL-18BP may be carried out in accordance with the invention, e.g. by passing a human fluid, such as urine or serum, through a chromatographic column to which IL-18 is coupled, and thereafter, eluting the bound IL-18BP.

The various IL-18BPs and viral IL-18BPs can also be prepared by recombinant means, i.e. by expressing IL-18BP in a suitable host, after operatively linking promoters, expression enhancers, regulatory sequences, etc., suitable for the particular host employed which e.g. allow expression in the correct orientation.

The various IL-18BPs and viral IL-18BPs and vectors for expressing IL-18 Bp in humans and other mammals may be employed in the treatment and alleviation of conditions in which IL-18 is involved or caused by an excess of exogenously administered or endogenously produced IL-18. Such conditions are, e.g., autoimmune diseases, type I diabetes, rheumatoid arthritis, graft rejections, inflammatory bowel disease, sepsis, multiple sclerosis, ischemic heart diseases (including heart attacks), ischemic brain injury, chronic hepatitis, psoriasis, chronic pancreatitis, acute pancreatitis and the like.

sis. In both cases, two polypeptide sequences were obtained. A major sequence and a minor sequence, the latter corresponding to a fragment of human defensin (accession number p11398), starting at amino acid 65. Subtraction of the known defensin sequence provided the following new sequence:

```
                    10
   T-P-V-S-Q-Q-x-x-x-A-A-A-      (SEQ ID NO: 11)
   1 . . . 5 . . =. =10 . .
``` wherein x represents a yet undetermined amino acid.

In order to obtain a longer and more accurate sequence and in order to identify potential cysteine residues, an aliquot of the eluted fraction was reduced with DTT under denaturing conditions, reacted with 4-vinyl pyridine, desalted by a micro-ultrafiltration device (Ultrafree, cutoff 10,000 Da, Millipore) and subjected to protein microsequence analysis. After sequencing cycle No. 1 the residual protein was reacted with o-phtalaldehyde to block all N-terminal polypeptides other than Pro and sequencing was then resumed. In this way the following single protein sequence was obtained:

```
                                              (SEQ ID NO: 10)
TPVSQXXXAA XASVRSTKDP CPSQPPVFPA AKQCPALEVT
1========10=======20=========30============40

(T = Thr; P = Pro; V = Val; S = Ser; Q=Gln;
X = Unknown; A = Ala; R=Arg; K = Lys; D = Asp;
C = Cys; F = Phe; L = Leu; E = Glu)
```

The resulting sequence is significantly different from that of any other known protein, as determined by searching protein databases. However, searching the database of The Institute of Genomic Research by the tblastn search program provided a cDNA file, denoted THC 123801, whose open reading frame (218 codons), when translated, contains a sequence highly homologous to that of the N-terminal sequence of IL-18BP. The homology is hereby shown:

```
 1   ...TPVSQXXXAAXASVRSTKDPCPSQPPVFPAAKQCPALEVT...    40   (SEQ ID NO: 10)
        | | |    |||||||||||||||||||||||||||||||
51   VTLLVRATXVXQTTTAATASVRSTKDPCPSQPPVFPAAKQCPALEVTWPE  100  (SEQ ID NO: 12)
```

According to the present invention, IL-18BP was isolated from normal human urine by one chromatographic step. A preparation of crude human urinary proteins concentrated from 500 l of normal human urine was loaded on a column consisting of human IL-18 bound to agarose. The column was washed and bound proteins were eluted at low pH. Eluted fractions were neutralized and aliquots were analyzed by SDS-PAGE (10% acrylamide) under non-reducing conditions and silver staining. A protein band of ~40 kD was specifically obtained in the eluted fractions (FIG. 1).

Figure 2:
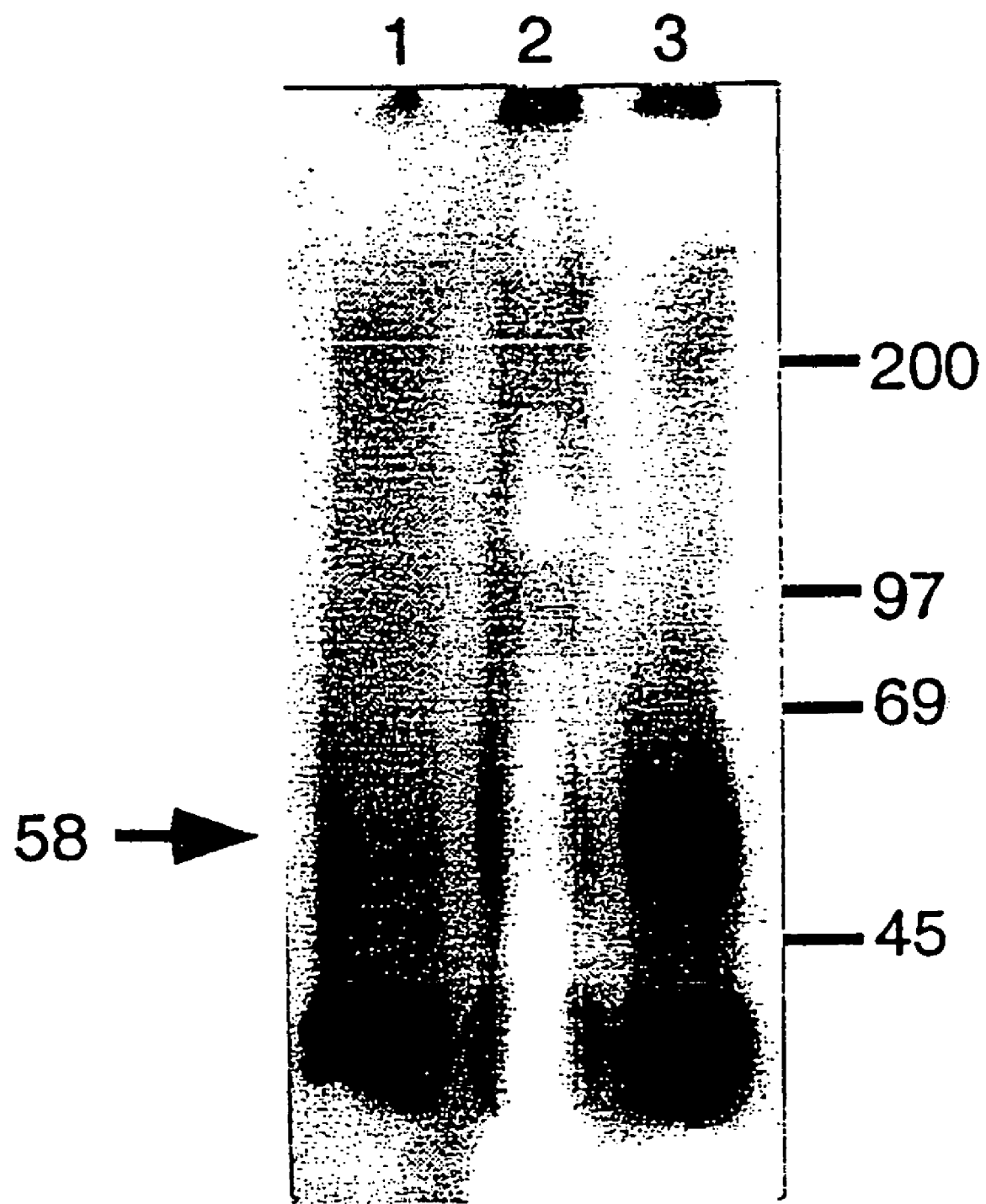
FIG. 2 shows an autoradiogram of SDS-PAGE (7.5% acrylamide) of complexes consisting of $^{125}$I-IL-18 (apparent molecular weight 19 kD), cross-linked to the following preparations of soluble IL-18 binding protein: Lane 1: Wash of the IL-18 affinity column. Lane 2: Elution 2 of the IL-18 affinity column. Lane 3: Elution 3 of the IL-18 affinity column. Molecular weight markers are indicated on the right side (in kD). An arrow indicates the cross-linked product (58 kD).

The ~40 kD protein obtained in the first step was identified as an IL-18 binding protein by its ability to specifically cross-link with $^{125}$I-IL-18 (FIG. 2). The ~40 kD protein was further characterized by N-terminal protein sequence analysis. Aliquots from the eluted protein were subjected to SDS-PAGE, electroblotted to a PVDF membrane and subjected to protein microsequence analysis. Similarly, aliquots from the eluted protein were subjected to direct protein microsequence analy- (The upper sequence (1-40) is that of the isolated IL-18BP; the lower sequence (51-100) is derived by translation of TIGR file THC123801).

The cDNA sequence identified as THC123801 is, however, only an EST (expressed sequence tag), i.e. a randomly selected cDNA clone. It has never been analyzed whether this EST contains an open reading frame, whether a protein is expressed from the gene corresponding to the EST or from the EST itself, nor has any function of a protein encoded by THC123801 ever been identified. No information was available at all that THC123801 contains an open reading frame coding for an IL-18BP.

The affinity-purified urinary IL-18BP retained the ability to bind its labeled ligand ($^{125}$I-IL-18), and following covalent cross-linking, a complex of molecular weight 58 kD was formed. The molecular weight of this complex corresponded to a 1:1 ratio of the ~40 kD IL-18BP and the 19 kD IL-18 (FIG. 2).

The affinity-purified urinary IL-18BP blocked the biological activity of human as well as mouse IL-18. Thus when IL-18BP was added to either human or mouse IL-18 it blocked the ability of IL-18 to induce the production of interferon-γ when added together with lipopolysaccharide (LPS) to cultures of mouse spleen cells (FIG. 3).

For the purpose of the present description the expression "biological activity of IL-18" refers inter alia to at least one of the following biological properties:

(i) induction of IFN-γ, primarily as a co-stimulant with mitogens, IL-1, IL-12, TNF-α, LPS in various cell types, such as mononuclear cells, murine splenocytes, human peripheral blood mononuclear cells, the human KG-1 cell line and T-cells,
(ii) enhancement of T-cell proliferation,
(iii) enhancement of Th-1 cytokine production in vitro, primarily as a co-stimulant,
(iv) synergism with IL-12 in terms of enhanced IFN-γ production, co-stimulatory action for production of IFN-γ and other T-helper cell-1 cytokines,
(v) co-stimulatory action for FAS ligand-mediated cytotoxicity of murine natural killer cell clones,
(vi) induction of the activation of NF-κB in human KG-1 cells, probably by inducing the formation of the 50 NF-κB homodimer and the p65/p50 NF-κB heterodimer,
(vii) induction of IL-8.

As used herein, the expression "binding to IL-18" means the capability of IL-18BP to bind IL-18, e.g. as evidenced by its binding to labeled IL-18 when affinity purified as in Example 2 herein.

As used herein, the expression "modulating the activity of IL-18" means the capability of IL-18BP to modulate any IL-18 activity other than blocking, e.g. partial inhibition, enhancement, or the like.

As used herein, the expression "blocking the activity of IL-18" refers to the activity of IL-18BP to block at least one of the above exemplified biological activities of IL-18. The IL-18 blocking activity of IL-18BP is exemplified by the ability of IL-18BP to block the IL-18 associated IFN-γ expression in murine splenocytes. As it will be shown below in more detail, the modulating or blocking activity of IL-18BP is in part due to the fact that IL-18BP inhibits the activation of NF-κB by IL-18. Furthermore, IL-18BP blocks at least one of the following activities of IL-18, namely induction of IFN-γ in human and mouse cells, induction of IL-8 and activation of NF-κB.

A DNA probe for screening cDNA libraries was prepared by reverse-transcription PCR with specific sense and antisense primers and RNA from the human Jurkat T cells with primers from the TIGR sequence. The resulting PCR product was confirmed by DNA sequence analysis. This PCR product was labeled with $^{32}$[P] and used as a probe for screening of four human cDNA libraries, derived from peripheral blood monocytes, from the Jurkat T-cell line, from PBMC and from human spleen. The various independent cDNA clones corresponded to four IL-18BP splice variants (SEQ ID NO:1, 3, 5 and 7). All splice variants coded for putative soluble secreted proteins. The most abundant one (IL-18BPa) had an open reading frame of 192 codons, coding for a signal peptide herein sometimes referred to as a "leader sequence" of 28 amino acid residues followed by a mature putative IL-18BPa, whose first 40 residues matched perfectly with the N-terminal protein sequence of the urinary IL-18BP (SEQ ID NO:2). The position of the cysteine residues suggested that this polypeptide belongs to the immunoglobulin (Ig) super-family. Interestingly, each of the four Gln residues within mature IL-18BPa was a potential N-glycosylation site. The three other variants of IL-18BP were less abundant than IL-18BPa. They included a shorter 1 kb IL-18BPb cDNA, coding for a signal peptide of 28 amino acid residues followed by a mature protein of 85 amino acid residues (SEQ ID NO:4). A third variant, IL-18BPc was represented by a 2.3 kb cDNA, coding for a signal peptide of 28 amino acid residues followed by a mature IL-18BP of 169 amino acid residues (SEQ ID NO:6). The fourth variant, IL-18BPd, coded for a signal peptide of 28 amino acid residues followed by a mature IL-18BP of 133 amino acid residues (SEQ ID NO:8).

To further study the possible existence of additional IL-18BP splice variants, a human genomic library was screened with a probe corresponding to full length IL-18BP cDNA. Five genomic clones, differing in length, were identified in this library. These clones were subjected to DNA sequence analysis with external and internal primers. Altogether, a 7.8 kb sequence was assembled from these clones (SEQ ID NO:9). No exon coding for a trans-membrane (TM) receptor was identified within the 7.8 kb sequence. All variants shared a common translation start site, coded for the same signal peptide of 28 amino acid residues and soluble mature proteins of varying sizes and C-terminal sequences. The IL-18BP locus contains an additional gene, coding for the nuclear mitotic apparatus protein 1 (NUMA1), positioned at the minus strand. This finding localizes the IL-18BP gene to human chromosome 11q13 (36).

An homology search was done with the complete protein sequence of IL-18BPa and the GenPept database, using the Smith Watermann algorithm. It was found that homologues of IL-18BP are expressed in several Poxviruses as secreted proteins of a previously unknown function. It was previously reported that viruses code for various cytokine receptors and that such virally encoded molecules serve as decoy receptors that inhibit immune responses by neutralizing their corresponding cytokine (reviewed by Spriggs, M K, 1994, Curr. Opin. Immunol., 6, 526-529). Therefore the invention further relates to virally encoded homologues of IL-18BP that may also serve as blockers or modulators of the biological activity of IL-18. Examples of virus-encoded homologues of IL-18BP are provided in Table 1.

According to the present invention the virus encoded homologue of IL-18BP may be expressed in a prokaryotic or eukaryotic host. As used herein, the expression "virus encoded homologue IL-18BP" refers to a similarity of at least 50% in a sequence of at least 70 amino acid residues. More preferably, it has at least 50%, at least 60%, at least 70%, at least 80% or, most preferably, at least 90% similarity thereto in a sequence of 100 amino acid residues.

TABLE 1

Virus-encoded proteins, showing high homology to human IL-18BP

| GenPept sequence | Virus type |
|---|---|
| MCU60315_54 | U60315 Molluscum contagiosum virus subtype 1 |
| MCU60315_53 | U60315 Molluscum contagiosum virus subtype 1 |
| SWPHLSB_12 | L22013 Swinepox virus |
| CV41KBPL_14 | Cowpox virus |
| VVCGAA_5 | Variola virus |
| U01161_3 174 | Ectromelia virus (mouse Poxvirus) |
| VVU18340_6 | Variola virus |
| VVU18338_7 | Variola virus |
| VVU18337_7 | Variola virus |
| VARCG_7 173 | Variola major virus |
| MCU60315_51 | Molluscum contagiosum virus |
| HNABV_1 | New Hepatitis non-A, non-B associated virus |

IL-18BPa was expressed in monkey COS7 cells. For this purpose, the cDNA of IL-18BPa was inserted into the mammalian expression vector pEF-BOS. A cassette coding for an (His)$_6$ sequence was added to the 3'-end of the IL-18BP ORFs in frame, in order to facilitate purification of the recombinant protein. COS7 cells were transiently transfected with the expression vector and serum-free medium of these cells (150 ml) was concentrated and purified by metal chelate chromatography. IL-18BPa ran as a single band upon SDS-PAGE with silver staining under reducing and non-reducing conditions and had the same apparent molecular mass as that of the urinary IL-18BP. Protein sequence analysis of this preparation revealed the same N-terminal sequence as that of the urinary IL-18BP. Immunoblot analysis of IL-18BPa with antibodies raised against the urinary IL-18BP revealed the same molecular mass band as that of the urinary protein. Furthermore, using immunoprecipitation followed by SDS-PAGE and autoradiography, IL-18BPa was able to displace urinary $^{125}$I-IL-18BP from binding to the antibody. Therefore, IL-18BPa corresponds structurally to the IL-18BP isolated from urine.

Crude and purified IL-18BPa were tested for their ability to inhibit the biological activity of IL-18. IL-18BPa inhibited the activity of human and mouse IL-18 in murine splenocytes, PBMC and the human KG-1 cell line (FIG. 9). These results confirm the identity of IL-18BPa cDNA as the one coding for a biologically active IL-18BP.

The invention further relates to muteins and fragments of IL-18BPs and viral IL-18BPs and to fused proteins consisting of wild type IL-18BPs and viral IL-18BPs or their muteins or their fragments, fused to another polypeptide or protein and being capable of binding IL-18 or its homologues.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the capability of the resulting products as compared with the wild type IL-18BP or viral IL-18BP to bind to IL-18. These muteins are prepared by known synthesis and/or by site-directed mutagenesis techniques, or any other known technique suitable therefor.

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mutein has at least 40% identity or homology with the sequence of either an IL-18BP or a virally-encoded IL-18BP homologue. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978; and Creighton, T. E., *Proteins: Structure and Molecular Properties*, W.H. Freeman & Co., San Francisco, 1983, which are hereby incorporated by reference. For a presentation of nucleotide sequence substitutions, such as codon preferences, see Ausubel et al, supra, at §§ A.1.1-A.1.24, and Sambrook et al, supra, at Appendices C and D.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule, Grantham, *Science*, Vol. 185, pp. 862-864 (1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues, Anfinsen, "Principles That Govern The Folding of Protein Chains", *Science*, Vol. 181, pp. 223-230 (1973). Proteins and muteins produced by such deletions and/or insertions come within the purview of the present invention.

However, cysteine residues which are not required for biological activity may be replaced with other residues, e.g. in order to avoid the formation of undesired intramolecular or intermolecular disulfide bridges which may cause a reduction in the activity of the IL-18BPs.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

| More Preferred Groups of Synonymous Amino Acids | |
|---|---|
| Amino Acid | Synonymous Group |
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

| Most Preferred Groups of Synonymous Amino Acids | |
|---|---|
| Amino Acid | Synonymous Group |
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. RE 33,653, 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In another preferred embodiment of the present invention, any mutein of an IL-18BP or a viral IL-18BP, has an amino acid sequence essentially corresponding to that of an IL-18BP, or to a viral IL-18BP. The term "essentially corresponding to" is intended to comprehend proteins with minor changes to the sequence of the natural protein which do not affect the basic characteristics of the natural proteins, particularly insofar as their ability to bind IL-18. The type of changes which are generally considered to fall within the "essentially corresponding to" language are those which would result from conventional mutagenesis techniques of the DNA encoding these proteins, resulting in a few minor modifications, and screening for the desired activity in the manner discussed above. In addition to binding IL-18, the muteins may also modulate and/or block IL-18 activity.

Muteins in accordance with the present invention include proteins encoded by a nucleic acid, such as DNA or RNA, which hybridizes to DNA or RNA, which encodes an IL-18BP or encodes a viral IL-18BP, in accordance with the present invention, under stringent conditions. The invention also includes such nucleic acid, which is also useful as a probe in identification and purification of the desired nucleic acid. Furthermore, such nucleic acid would be a prime candidate to determine whether it encodes a polypeptide, which retains the functional activity of an IL-18BP of the present invention. The term "stringent conditions" refers to hybridization and subsequent washing conditions, which those of ordinary skill in the art conventionally refer to as "stringent". See Ausubel et al., *Current Protocols in Molecular Biology*, supra, Interscience. N.Y., §§6.3 and 6.4 (1987, 1992), and Sambrook et al., supra. Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

The invention further includes nucleic acids which code for IL-18BP according to the present invention, but which differ in codon sequence due to the degeneracy of the genetic code. Such a DNA which possibly does not hybridize under stringent conditions to the DNA sequences shown in FIGS. 4 to 7, but is nevertheless capable of encoding an IL-18BP according to the present invention is also included by the invention.

The term "fused protein" refers to a polypeptide comprising an IL-18BP, or a viral IL-18BP, or a mutein thereof, fused with another protein, which, e.g., has an extended residence time in body fluids. An IL-18BP or a viral IL-18BP, may thus be fused to another protein, polypeptide or the like, e.g., an immunoglobulin or a fragment thereof. It may also be fused to polyethylene glycol (PEG) in order to prolong residence time.

The term "salts" herein refers to both salts of carboxyl groups and to acid addition salts of amino groups of an IL-18BP, a viral IL-18BP, muteins, or fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course, any such salts must have substantially similar activity to IL-18BP.

"Functional derivatives" as used herein cover derivatives of IL-18BPs or a viral IL-18BP, and their muteins and fused proteins, which may be prepared e.g. from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it. These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction substantially retains the capability of binding IL-18.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

Various recombinant cells such as prokaryotic cells, e.g., *E. coli*, or other eukaryotic cells, such as yeast or insect cells can produce IL-18BPs or viral IL-18BPs. Methods for constructing appropriate vectors, carrying DNA that codes for an IL-18BP and suitable for transforming (e.g., *E. coli*, mammalian cells and yeast cells), or infecting insect cells in order to produce a recombinant IL-18BP or a viral IL-18BP are well known in the art. See, for example, Ausubel et al., eds. "Current Protocols in Molecular Biology" *Current Protocols*, 1993; and Sambrook et al., eds. "Molecular Cloning: A Laboratory Manual", 2nd ed., Cold Spring Harbor Press, 1989.

For the purposes of expression of IL-18BP proteins, or viral IL-18BPs, DNA encoding an IL-18BP or a viral IL-18BP, their fragments, muteins or fused proteins, and the operably linked transcriptional and translational regulatory signals, are inserted into vectors which are capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototrophy to an auxotropic host, biocide resistance, e.g., antibiotics, or resistance to heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals.

Said DNA molecule to be introduced into the cells of choice will preferably be incorporated into a plasmid or viral vector capable of autonomous replication in the recipient host. Preferred prokaryotic plasmids are derivatives of pBr322. Preferred eukaryotic vectors include BPV, vaccinia, SV40, 2-micron circle, etc., or their derivatives. Such plasmids and vectors are well known in the art (2-5, 22). Once the vector or DNA sequence containing the construct(s) has been prepared for expression, the expression vector may be introduced into an appropriate host cell by any of a variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as *E. coli, Bacillus, Streptomyces, Pseudomonas, Salmonella, Serratia*, etc. The most preferred prokaryotic host is *E. coli*. Bacterial hosts of particular interest include *E. coli* K12 strain 294 (ATCC 31446). *E. coli* X1776 (ATCC 31537), *E. coli* W3110 ($F^-$, lambda$^-$, phototropic (ATCC 27325). Under such conditions, the protein will not be glycosylated. The prokaryotic host must be compatible with the replicon and control sequences in the expression plasmid.

However, since natural IL-18BPs are glycosylated proteins, eukaryotic hosts are preferred over prokaryotic hosts. Preferred eukaryotic hosts are mammalian cells, e.g., human, monkey, mouse and Chinese hamster ovary (CHO) cells, because they provide post-translational modifications to protein molecules including correct folding, correct disulfide bond formation, as well as glycosylation at correct sites. Also yeast cells and insect cells can carry out post-translational peptide modifications including high mannose glycosylation.

A number of recombinant DNA strategies exist which utilize strong promoter sequences and high copy number of plasmids, which can be utilized for production of the desired proteins in yeast and in insect cells. Yeast and insect cells recognize leader sequences on cloned mammalian gene products and secrete mature IL-18BP. After the introduction of the vector, the host cells are grown in a selective medium, which selects for the growth of vector-containing cells. Expression of the cloned gene sequence(s) results in the production of an IL-18BP, a viral IL-18BP, fusion proteins, or muteins or fragments thereof. The above-mentioned cloning, clone isolation, identification, characterization and sequencing procedures are described in more detail hereinafter in the Examples.

The expressed proteins are then isolated and purified by any conventional procedure involving extraction, precipitation, chromatography, electrophoresis, or the like, or by affinity chromatography, using, e.g., an anti-IL-18BP monoclonal antibodies immobilized on a gel matrix contained within a column. Crude preparations containing said recombinant IL-18BP are passed through the column whereby IL-18BP will be bound to the column by the specific antibody, while the impurities will pass through. After washing, the protein is eluted from the gel under conditions usually employed for this purpose, i.e. at a high or a low pH, e.g. pH 11 or pH 2.

The invention further relates to vectors useful for expression of an IL-18BP or a viral IL-18BP or their derivatives in mammals and more specifically in humans. Vectors for short and long-term expression of genes in mammals are well known in the literature. Studies have shown that gene delivery to e.g., skeletal muscle, vascular smooth muscle and liver result in systemic levels of therapeutic proteins. Skeletal muscle is a useful target because of its large mass, vascularity and accessibility. However, other targets and particularly bone marrow precursors of immune cells have been used successfully. Currently available vectors for expression of proteins in e.g., muscle include plasmid DNA, liposomes, protein-DNA conjugates and vectors based on adenovirus, adeno-associated virus and herpes virus. Of these, vectors based on adeno-associated virus (AAV) have been most successful with respect to duration and levels of gene expression and with respect to safety considerations (Kessler, P. D. 1996, Proc. Natl. Acad. Sci. USA 93, 14082-14087).

Procedures for construction of an AAV-based vector have been described in detail (Snyder et al, 1996, Current Protocols in Human Genetics, Chapters 12.1.1-12.1.17, John Wiley & Sons) and are incorporated into this patent. Briefly plasmid psub201, containing the wild-type AAV genome is cut with the restriction enzyme Xba I and ligated with a construct consisting of an efficient eukaryotic promoter, e.g., the cytomegalovirus promoter, a Kozak consensus sequence, a DNA sequence coding for an IL-18BP or a viral IL-18BP, or their muteins or fusion proteins or fragments thereof, a suitable 3' untranslated region and a polyadenylation signal, e.g., the polyadenylation signal of simian virus 40. The resulting recombinant plasmid is cotransfected with an helper AAV plasmid e.g., pAAV/Ad into mammalian cells e.g., human T293 cells. The cultures are then infected with adenovirus as a helper virus and culture supernatants are collected after 48-60 hours. The supernatants are fractionated by ammonium sulfate precipitation, purified on a CsCl density gradient, dialyzed and then heated at 56° C. to destroy any adenovirus, whereas the resulting recombinant AAV, capable of expressing IL-18BP or a viral IL-18BP, or their muteins or fusion proteins remains stable at this step.

So far, the physiological role of the soluble cytokine receptors has not been established. The soluble receptors bind their specific ligands and in most cases inhibit their biological activity, as was shown, e.g., in the TNF system (11, 12). In very few cases, e.g., IL-6, the soluble receptor enhances the biological activity. The recombinant soluble TNF receptor, also known as TBP (TNF binding protein) was found to prevent septic shock in animal models, while soluble forms of IL-1 receptor were found to have profound inhibitory effects on the development of in vivo alloreactivity in mouse allograft recipients.

Similarly, the IL-18BPs and viral IL-18BPs of the present invention may find use as modulators of IL-18 activity, e.g. in type I diabetes, in sepsis, in autoimmune diseases, in graft rejections, rheumatoid arthritis, inflammatory bowel disease, sepsis, multiple sclerosis, ischemic heart disease including acute heart attacks, ischemic brain injury, chronic hepatitis, psoriasis, chronic hepatitis and acute hepatitis. They may thus be used, e.g. in any disease in which endogenous production or exogenous administration of IL-18 induces the disease or aggravates the situation of the patient.

The present invention further relates to pharmaceutical compositions comprising a pharmaceutically acceptable carrier and an IL-18BP or a viral IL-18BP of the invention or their active muteins, fused proteins and their salts, functional derivatives or active fractions thereof.

The present invention further relates to pharmaceutical compositions comprising a pharmaceutically acceptable carrier and e.g., a viral vector such as any one of said AAV-based viral vectors or another vector expressing an IL-18BP or viral IL-18BP or their muteins, fragments or fusion proteins thereof and suitable for administration to humans and other mammals for the purpose of attaining expression in vivo of IL-18BP or a viral IL-18BP or their muteins or fragments or fusion protein of the invention, i.e. for use in gene therapy.

The pharmaceutical compositions of the invention are prepared for administration by mixing an IL-18BP or a viral IL-18BP, or their derivatives, or vectors for expressing same with physiologically acceptable carriers, and/or stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, subcutaneously, by local injection or topical application, or continuously by infusion, etc. The amount of active compound to be administered will depend on the route of administration, the disease to be treated and the condition of the patient. Local injection, for instance, will require a lower amount of the protein on a body weight basis than will intravenous infusion.

Accordingly, IL-18BPs, or viral IL-18BPs, or vectors expressing same in vivo are indicated for the treatment of autoimmune diseases, Type I diabetes, rheumatoid arthritis, graft rejections, inflammatory bowel disease, sepsis, multiple sclerosis, ischemic heart disease including acute heart attacks, ischemic brain injury, chronic hepatitis, psoriasis, chronic pancreatitis and acute pancreatitis and similar diseases, in which there is an aberrant expression of IL-18, leading to an excess of IL-18 or in cases of complications due to exogenously administered IL-18.

The invention also includes antibodies against an IL-18BP or a viral IL-18BP, as well as against their muteins, fused proteins, salts, functional derivatives and active fractions. The term "antibody" is meant to include polyclonal antibodies, monoclonal antibodies (MAbs), chimeric antibodies, anti-idiotypic (anti-Id) antibodies to antibodies that can be labeled in soluble or bound form, and humanized antibodies as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, Nature 256:495-497 (1975); U.S. Pat. No. 4,376, 110; Ausubel et al, eds., supra, Harlow and Lane, ANTIBODIES: A LABORATORY MANUAL, Cold Spring Harbor Laboratory (1988); and Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a MAb of the present invention may be cultivated in vitro, in situ or in vivo. Production of high titers of MAbs in vivo or in situ makes this the presently preferred method of production.

Chimeric antibodies are molecules, different portions of which are derived from different animal species, such as those having the variable region derived from a murine MAb and a human immunoglobulin constant region. Chimeric antibodies are primarily used to reduce immunogenicity in application and to increase yields in production, for example, where murine MAbs have higher yields from hybridomas but higher immunogenicity in humans, such that human/murine chimeric MAbs are used. Chimeric antibodies and methods for their production are known in the art (Cabilly et al, *Proc. Natl. Acad. Sci. USA* 81:3273-3277 (1984); Morrison et al., *Proc. Natl. Acad. Sci. USA* 81:6851-6855 (1984); Boulianne et al., *Nature* 312:643-646 (1984); Cabilly et al., European Patent Application 125023 (published Nov. 14, 1984); Neuberger et al., Nature 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066-1074 (1986); Robinson et al., International Patent Publication, WO 9702671 (published 7 May 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988); and Harlow and Lane, ANTIBODIES: A LABORATORY MANUAL, supra. These references are entirely incorporated herein by reference.

An anti-idiotypic (anti-Id) antibody is an antibody, which recognizes unique determinants generally, associated with the antigen-binding site of an antibody. An Id antibody can be prepared by immunizing an animal of the same species and genetic type (e.g., mouse strain) as the source of the MAb with the MAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original MAb, which induced the anti-Id. Thus, by using antibodies to the idiotypic determinants of a MAb, it is possible to identify other clones expressing antibodies of identical specificity.

Accordingly, MAbs generated against IL-18BP and related proteins of the present invention may be used to induce anti-Id antibodies in suitable animals, such as BALB/c mice. Spleen cells from such immunized mice are used to produce anti-Id hybridomas secreting anti-Id Mabs. Further, the anti-Id Mabs can be coupled to a carrier such as keyhole limpet hemocyanin (KLH) and used to immunize additional BALB/c mice. Sera from these mice will contain anti-anti-Id antibodies that have the binding properties of the original MAb specific for an IL-18BP epitope or epitopes of a viral IL-18BP.

The anti-Id MAbs thus have their own idiotypic epitopes, or "idiotopes" structurally similar to the epitope being evaluated, such as an IL-18BP or a viral IL-18BP.

The term "humanized antibody" is meant to include e.g. antibodies which were obtained by manipulating mouse antibodies through genetic engineering methods so as to be more compatible with the human body. Such humanized antibodies have reduced immunogenicity and improved pharmacokinetics in humans. They may be prepared by techniques known in the art, such as described, e.g. for humanzied anti-TNF antibodies in Molecular Immunology, Vol. 30, No. 16, pp. 1443-1453, 1993.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316-325 (1983)). It will be appreciated that Fab and F(ab')$_2$ and other fragments of the antibodies useful in the present invention may be used for the detection and quantitation of an IL-18BP or a viral IL-18BP, according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to detect quantitatively or qualitatively an IL-18BP or a viral IL-18BP, or related proteins in a sample or to detect presence of cells, which express such proteins of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of an IL-18BP or a viral IL-18BP, and related proteins of the present invention. In situ detection may be accomplished by removing a histological specimen from a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of an IL-18BP or a viral IL-18BP, or related proteins but also its distribution on the examined tissue. Using the present invention, those of ordinary skill will readily perceive that any of wide variety of histological methods (such as staining procedures) can be modified in order to achieve such in situ detection.

Such assays for an IL-18BP or a viral IL-18BP, or related proteins of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying IL-18BP or related proteins, and detecting the antibody by any of a number of techniques well-known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of antibody in accordance with the present invention may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods, which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect an IL-18BP or a viral IL-18BP, through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmuno Assay and Related Techniques" by Chard, T., incorporated by reference herein. The radioactive isotope can be detected by such means as the use of a gamma counter or a scintillation counter or by autoradiography.

It is also possible to label an antibody in accordance with the present invention with a fluorescent compound. When the fluorescently labeled antibody is exposed to light of the proper wavelength, its presence can be then be detected due to fluorescence. Among the most commonly used fluorescent labeling compounds are fluorescein isothiocyanate, rhodamine, phycoerythin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriamine pentaacetic acid (ETPA).

The antibody can also be detectably labeled by coupling it to biotin. Biotinylated antibody can then be detected by avidin or streptavidin coupled to a fluorescent compound or to an enzyme such as peroxidase or to a radioactive isotope and the like.

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The present invention also provides DNA molecules encoding any of the proteins of the present invention as defined above, replicable expression vehicles comprising any such DNA molecules, host cells transformed with any such expression vehicles including prokaryotic and eukaryotic and host cells, preferably CHO cells. The invention also includes a process for the production of expression vectors coding for any of the proteins of the present invention for the purpose of their expression in humans and other mammals.

The invention also includes a process for the production of any of the proteins of the present invention by culturing a transformed cell in accordance with the present invention and recovering the protein encoded by the DNA molecule and the expression vehicle within such transformed host cell.

In addition to the use of an IL-18BP or a viral IL-18BP, in modulating the activity of IL-18, they can, of course, also be employed for the purification of IL-18 itself. For this purpose, IL-18BP or a viral IL-18BP is coupled to an affinity column and crude IL-18 is passed through. The IL-18 can then be recovered from the column by, e.g., elution at low pH.

The invention will now be illustrated by the following non-limiting examples:

EXAMPLE 1

Isolation of an IL-18 Binding Protein

*E. coli* IL-18 (2.5 mg, Peprotech, NJ) was coupled to Affi-gel-10 (0.5 ml, BioRad), according to the manufacturer's instructions and packed into a column. Crude urinary proteins (1000-fold concentrated, 500 ml) were loaded onto the column at a flow rate of 0.25 ml/min. The column was washed with 250 ml 0.5M NaCl in phosphate buffered saline (PBS). Bound proteins were then eluted with 25 mM citric acid, pH 2.2 and benzamidine (1 mM), immediately neutralized by 1M $Na_2CO_3$. Fractions of 1 ml were collected. The fractions were analyzed by SDS-PAGE and silver staining. The IL-18 binding protein eluted in fractions 2-8 as a ~40,000 Dalton protein (FIG. 1). The ~40 kD band, corresponding to the IL-18BP exhibited a distinct yellow color upon silver staining. The various fractions were analyzed by cross-linking with $^{125}$I-IL-18, SDS-PAGE and autoradiography as described in Example 2. An IL-18 binding protein was found in fractions 2-8, eluted from the IL-18-agarose column (FIG. 2).

EXAMPLE 2

Cross-Linking of Affinity-Purified IL-18BP to Labeled IL-18

Samples (40 μl) of IL-18BP from the affinity purification step were incubated (70 min. at 4° C.) with $^{125}$I-IL-18 (5,000,000 cpm). Disuccinimidyl suberate (DSS), dissolved in dimethyl sulfoxide ($Me_2SO$, 20 mM), was then added to a final concentration of 2 mM and the mixture was left for 20 min. at 4° C. The reaction was stopped by the addition of 1M Tris-HCl pH 7.5, and 1M NaCl to a final concentration of 100 mM. A sample buffer containing Dithiothreitol (DTT, 25 mM final) was added and the mixtures were analyzed by SDS-PAGE (7.5% acrylamide) followed by autoradiography (FIG. 2).

A specific band of molecular weight 58 kD, probably consisting of a ~40 kD protein cross-linked to the ~20 kD $^{125}$I-IL-18, was observed in fractions eluted from the IL-18 affinity column (lanes 2 and 3) but not in the column wash (lane 1), containing all other crude urinary proteins.

EXAMPLE 3

Protein Sequence Analysis

Eluted fractions from the affinity column of Example 1 were resolved by SDS-PAGE (10% acrylamide) under non-reducing conditions, electroblotted on a PVDF membrane (Pro-Blot, Applied Biosystems, USA). The membrane was stained with coomassie blue, the ~40 kD band was excised and subjected to protein sequence analysis by a Procise microsequencer (Applied Biosystems, USA). The following major sequence was obtained:

```
T-P-V-S-Q-Q-x-x-A-A-A      (SEQ ID NO: 11)
1 . . . 5 . . . . 10 . .
``` wherein x represents a yet undetermined amino acid.

In addition, a minor sequence was obtained:

```
A-x-Y-x-R-I-P-A-x-A-I-A    (SEQ ID NO: 13)
1 . . . 5 . . . . 10 . .
```

Because of this double sequence it was not possible to obtain a longer sequence data. The minor sequence was identified as a fragment of human defensin, (accession No. p11398) starting at amino acid 65 of defensin. The major sequence could not be associated with any other known protein, as determined by searching all available databases in NCBI and TIGR by the blastp and tblastn search programs.

In order to obtain a longer and more accurate sequence and in order to identify potential cysteine residues, another aliquot of the fraction eluted from the IL-18-agarose column was reduced with DTT in 6 M guanidine HCl, reacted with 4-vinyl pyridine, desalted by a micro-ultrafiltration device (Ultrafree, cutoff 10,000 Daltons, Millipore) and subjected to protein microsequence analysis. After cycle No. 1 of sequencing, the filter was reacted with o-phtalaldehyde to block all N-terminal polypeptides other than Pro. In this way only the major sequence was obtained as follows:

```
                                          (SEQ ID NO: 10)
TPVSQXXXAA XASVRSTKDP CPSQPPVFPA AKQCPALEVT
1========10=========20=========30=========40

(T = Thr; P = Pro; V = Val; S =
Ser; G = Gln; X = Unknown; A = Ala;
R = Arg; K = Lys; D = Asp; C =
Cys; F = Phe; L = Leu; E = Glu)
```

In cycles 6, 7, 8 and 11 a low level of a Thr signal was obtained. Because of this low level we considered it more prudent not to assign a specific amino acid residue at said cycles.

The resulting sequence is significantly different from that of any other known protein, as determined by searching protein databases. However, searching the TIGR database by the tblastn search program provided a cDNA file, denoted THC123801, whose open reading frame (218 codons), when translated contains a sequence highly homologous to that of the N-terminal sequence of IL-18BP. The homology is hereby shown:

```
 1    ...TPVSQXXXAAXASVRSTKDPCPSQPPVFPAAKQCPALEVT....    40   (SEQ ID NO: 10)
         | | |    ||||||||||||||||||||||||||||||||
51    VTLLVRATXVXQTTTAATASVRSTKDPCPSQPPVFPAAKQCPALEVTWPE  100  (SEQ ID NO: 11)
```

(The upper sequence (1-40) is that of the IL-18BP isolated according to the invention; the lower sequence (51-100) is deduced by translation of the cDNA of TIGR file THC123801).

The putative protein sequence, obtained by translating file THC123801, was ambiguous at residues 2 and 4 of the IL-18BP. It confirms the identity of amino acid residues 6, 7 and 8 of IL-18BP as Thr and seems to do so also for residue 11.

EXAMPLE 4

The IL-18BP is a Glycoprotein

Aliquot (0.3 ml) of eluted fractions of Example 1 were further purified by size exclusion chromatography on a Superose 12 column (1×30 cm, Pharmacia, Sweden). The column was pre-equilibrated and eluted with phosphate buffered saline and sodium azide (0.02%) at a flow rate of 0.5 m/min. and fractions of 1 min. were collected. The IL-18 binding protein eluted in fractions 20-25 as a ~40,000 Dalton protein, as determined by SDS-PAGE and silver staining. A sample containing the ~40,000 Dalton protein (fraction 23, 50 µl, ~50 ng protein) was reacted with N-glycosidase F (PNGase F, Biolab) according to the manufacturers instructions. Briefly, the aliquot was denatured by boiling in the presence of 5% SDS for 10 min., 10xG7 buffer (2.5 µl), 10% NP-40 (2.5 µl) and PNGase F (1 µl), 1 h at 37° C. The sample was analyzed by SDS-PAGE (10% acrylamide) under non-reducing conditions and compared with undigested IL-18BP from the same Superose 12 fraction. It was found that the ~40 kD band of IL-18BP disappeared in the PNGase-treated fraction. New bands, corresponding to 30 kD (just above the PNGase band) and 20 kD were obtained. The elimination of the ~40 kD band indicates that this band is an N-glycosylated protein.

EXAMPLE 5

Blocking of the Biological Activity of IL-18 by IL-18BP

Figure 3A:
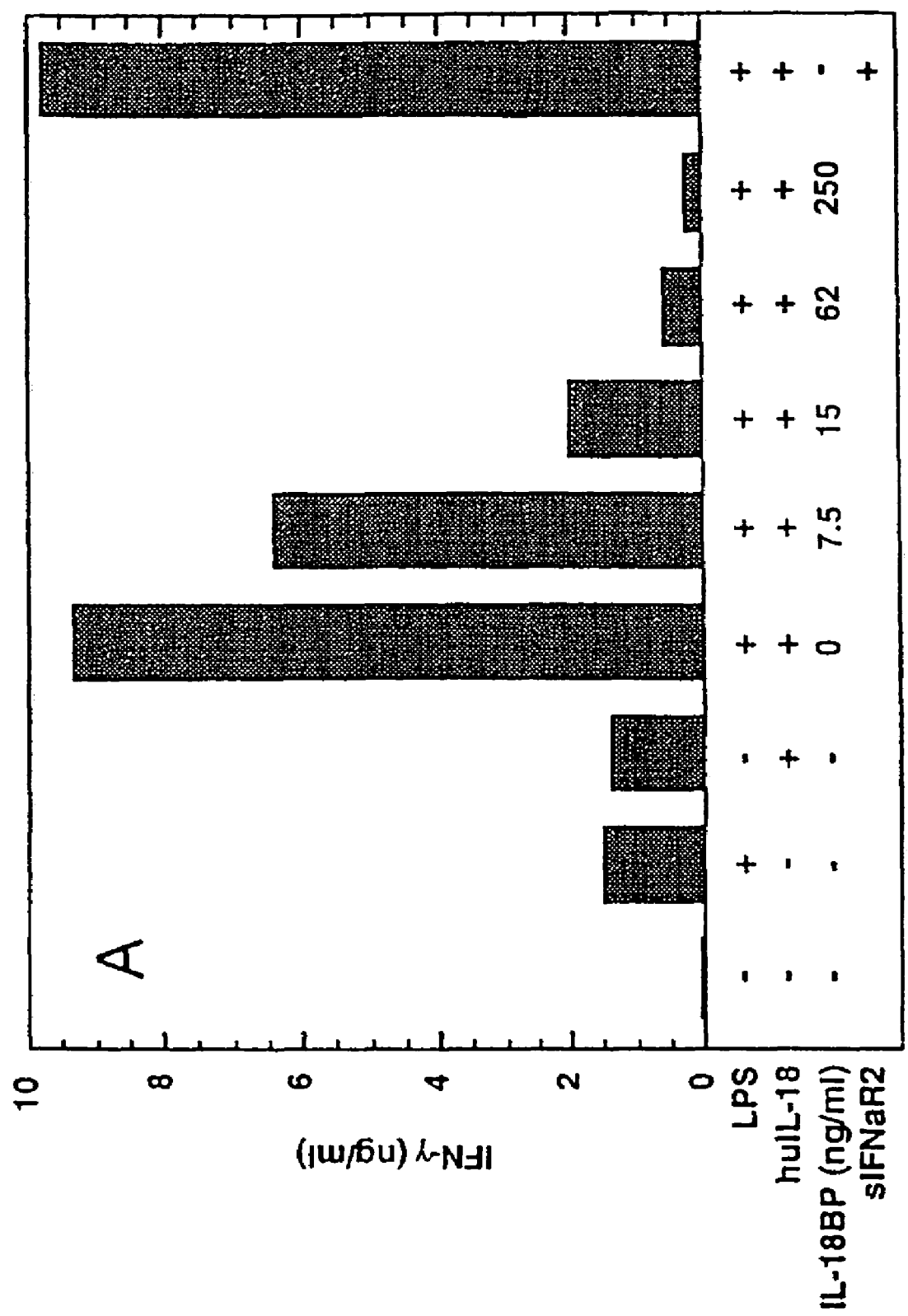
Figure 3E:
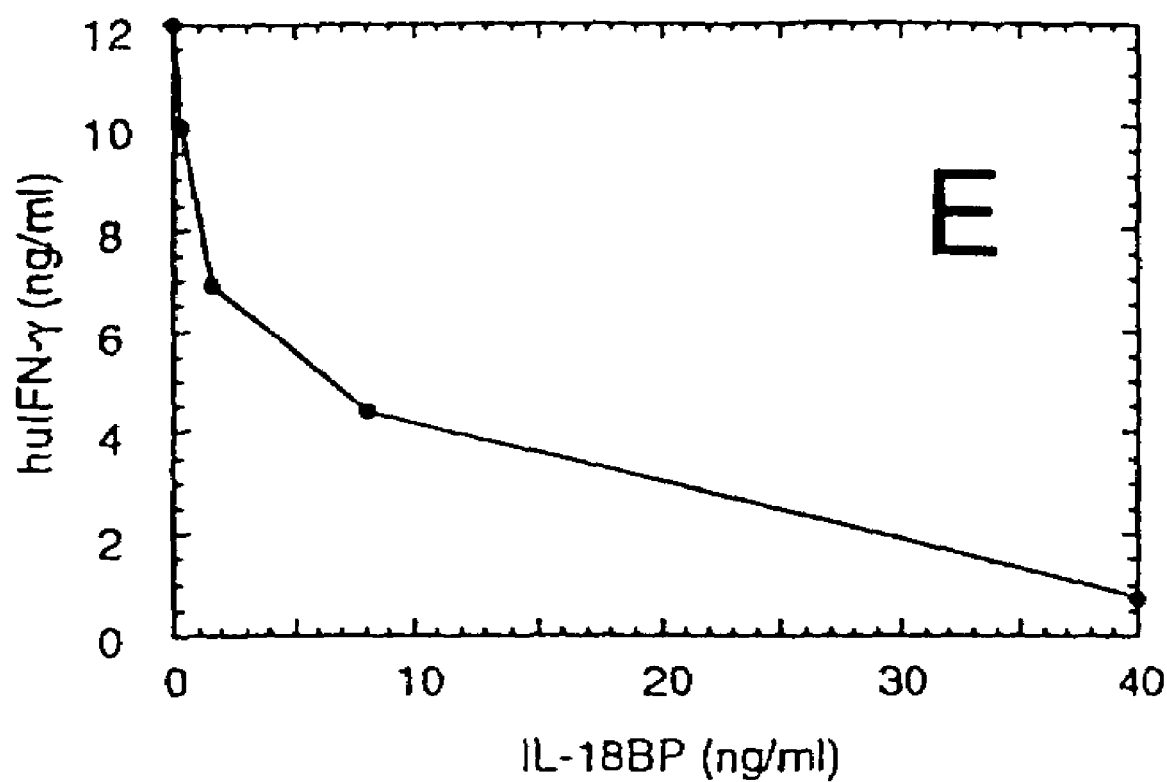

The ability of the IL-18BP isolated from urine to block IL-18 activity was determined by measuring the IL-18-induced production of IFN-γ in mononuclear cells. IL-18 induces IFN-γ when added together with either low concentration of LPS, IL-12, IL-2, or other stimulants. The activity of IL-18 was tested in murine splenocytes, in human peripheral blood mononuclear cells (PBMC) and in the human KG-1 cell line. Spleen cells were prepared from a healthy mouse, washed and suspended in RPMI 1640 medium supplemented with 10% fetal bovine serum at $5 \times 10^6$ cells/ml. 1.0 ml cultures were stimulated with LPS (either 0.5 or 1 µg/ml) together with recombinant human or murine IL-18 (either 0.5 or 5 ng/ml). Human IL-18 binding protein (0, 5 or 50 ng/ml) was added to the recombinant IL-18 before adding to spleen cells. After culturing for 24 h, the spleen cells were subjected to three freeze (−70° C.) and thaw (room temperature) cycles, the cellular debris was removed by centrifugation and the supernatants were assayed for IFN-γ using the ELISA kits for mouse IFN-γ (Endogen). As shown in FIG. 3A, IL-18BP blocked the activity of huIL-18 in murine splenocytes in a dose-dependent manner. In contrast, as a control, soluble interferon-α/β receptor had no effect. The activity of recombinant murine IL-18 was similarly inhibited by the human IL-18BP, suggesting that human IL-18BP recognizes murine IL-18 (FIG. 3B). Endogenous IL-18 is induced in murine splenocytes by high concentrations of LPS, leading to production of IFN-γ. Indeed, IFN-γ induction by LPS (10 µg/ml) was also inhibited by the urinary IL-18BP (FIG. 3C). Concanavalin A (con A) activates T-cells to produce IFN-γ in the absence of IL-18 (13)]. Indeed, induction of IFN-γ by Con A was not inhibited by IL-18BP even at high concentrations (FIG. 3D). This observation demonstrated that IL-18BP was a specific inhibitor of IL-18 bioactivity rather than a non-specific inhibitor of IFN-γ production. IL-18BP also inhibited the activity of human IL-18 in human KG-1 cells induced by a combination of IL-18 and TNF-α (FIG. 3E).

The above data demonstrate that urinary IL-18BP inhibits human as well as murine IL-18 activity as measured by co-induction of IFN-γ in human and murine mononuclear cells. The concentration of IL-18BP which reduced IL-18 activity by >90% was comparable to that of IL-18 itself, suggesting a high affinity interaction between these two proteins.

EXAMPLE 6

Isolation of cDNA Clones Coding for IL-18BP

Total RNA from Jurkat T-cells (CRL 8163, American Type Culture Collection) was reverse-transcribed with SuperScript RNase H$^-$ reverse transcriptase (Gibco-BRL) and random primers (Promega, Madison Wis.). The resulting cDNA fragments were then amplified by PCR, using Taq DNA polymerase (Sigma) and primers corresponding to TIGR clone THC123801 nucleotides 2444 (sense) and 500-481 (reverse). The amplification was done in 30 cycles of annealing (55° C., 2 min) and extension (70° C., 1 min). The resulting PCR products were resolved by agarose (1%) gel electrophoresis, eluted and cloned into pGEM-Teasy TA cloning vector (Promega). DNA from individual clones was sequenced with T7 and SP6 primers.

The resulting 477 bp fragment was $^{32}$P-labeled by random priming. This probe was used for screening various human cDNA and genomic libraries. Duplicate nitrocellulose filters were lifted and hybridized with the probe at 60° C. in a buffer consisting of 6×SSC, 10× Denhardt's solution, 0.1% SDS and 100 µg/ml Salmon sperm DNA. The filters were washed and exposed overnight at −80° C. to Kodak XAR film. Double positive clones were plaque-purified. Plasmids were excised from the λpCEV9 clones and self-ligated. cDNA clones from other libraries were isolated according to the manufacturer's instructions. Automated DNA sequence analysis of the isolated clones was performed with Models 373A and 377 sequencers (Applied Biosystems) using sense and antisense primers. Standard protocols were used for these cloning procedures (33).

The following libraries were screened: a human monocyte cDNA library, constructed in λpCEV9 cloning vector (15), kindly provided by T. Miki; a human Jurkat leukemic T-cell cDNA library, a human peripheral blood leukocyte cDNA library and a human spleen cDNA library, all from Clontech (Palo Alto, Calif.). A human placenta genomic library in lambda FIX II vector was from Stratagene (La Jolla, Calif.).

All cDNA clones corresponded to four different IL-18BP splice variants were obtained and characterized. All splice variants coded for putative soluble secreted proteins. The most abundant one (IL-18BPa) had an open reading frame of 192 codons, coding for a signal peptide of 28 amino acid residues followed by a mature putative IL-18BPa, whose first 40 residues (SEQ ID NO:10) matched perfectly with the N-terminal protein sequence of the urinary IL-18BP (SEQ ID NO:2). The position of the cysteine residues suggested that this polypeptide belongs to the immunoglobulin (Ig) super-family. Each of the four Gln residues within mature IL-18BPa was a potential N-glycosylation site. The other three splice variants of IL-18BP were significantly less abundant.

Another 1 kb IL-18BPb cDNA coded for a mature protein of 85 amino acid residues (SEQ ID NO:4). A third variant, IL-18BPc, was represented by a 2.3 kb cDNA, coding for a mature IL-18BP of 169 amino acid residues (SEQ ID NO:6). The fourth variant, IL-18BPd coded for a mature IL-18BP of 133 amino acid residues (SEQ ID NO:8). In-exon splicing occurred at two sites along the pro-mRNA. These events and an additional 5' exon in IL-18BPd gave rise to 3 different 5' UTRs in the various cDNA clones. It is therefore quite possible that different IL-18BP variants may be generated in response to distinct transcription regulation signals.

No cDNA coding for a receptor with a transmembrane domain was found so far.

EXAMPLE 7

Construction of a Mammalian Expression Vector, Production of Recombinant IL-18BP, and Evaluation of the Biological Activities of Recombinant IL-18BP The coding region of the IL-18BPa cDNA was amplified by PCR with the sense primer

```
                                           (SEQ ID NO: 14)
5' TATATCTAGAGCCACCATGAGACACAACTGGACACCA
``` and the reverse primer:

```
                                           (SEQ ID NO: 15)
5' ATATCTAGATTAATGATGATGATGATGACCCTGCTGCTGTGGAC
TGC
```

The PCR products were cut with Xba I and cloned into the Xba I site of the pEF-BOS expression vector (25), to yield pEF-BOS-IL-18BPa. The constructs were confirmed by DNA sequencing.

Batches of $6 \times 10^7$ COS7 cells in 1.4 ml TD buffer, containing pEF-BOS-IL-18BPa plasmid DNA (10 µg) and DEAE-dextran (120 µg) were incubated for 30 min at room temperature, as described (35). The cells were then washed with DMEM-10% FBS, plated for 4 hr in DMEM-10, washed and incubated for 3-5 days in serum-free DMEM. Culture medium was collected, concentrated 6-fold by ultrafiltration (10 kD cutoff) and the IL-18BP-His$_6$ was isolated on a Talon column (Clontech) with imidazole as eluant according to the manufacturer's instructions.

Immunological cross-reactivity of the urinary and the COS7-expressed IL-18BP was assessed as follows: Urinary IL-18BP (5 µg) was labeled with $^{125}$I by the chloramine T procedure. Supernatants of COS7 cells (250 µl) were mixed (1 h, room temperature final volume 500 µl) with the antibody to urinary IL-18BP, diluted 1:1000 in phosphate-buffered saline (PBS), 0.05% Tween 20 and 0.5% bovine serum albumin (Wash Buffer). $^{125}$I-labeled urinary IL-18BP (106 cpm) was then added and after 1 h protein G-sepharose (20 µl) was added. The mixture was suspended (1.5 h, 4° C.), the beads were then isolated and washed wash 3× Wash Buffer and once in PBS. The beads were then eluted with a Sample buffer, resolved by SDS-PAGE (10% acrylamide under reducing conditions followed by Autoradiography.

IL-18BPa ran as a single band upon SDS-PAGE with silver staining under reducing and non-reducing conditions and had the same apparent molecular mass as that of the urinary IL-18BP (data not shown). Protein sequence analysis of this preparation revealed the same N-terminal sequence as that of the urinary IL-18BP, indicating that the latter was not degraded at its N-terminus.

Immunoblot analysis of IL-18BPa with antibodies raised against the urinary IL-18BP revealed the same molecular mass band as that of the urinary protein. Furthermore, using immunoprecipitation followed by SDS-PAGE and autoradiography, IL-18BPa was able to displace urinary $^{125}$I-IL-18BP from binding to the antibody. Therefore, IL-18BPa corresponds structurally to the urinary IL-18BP.

Crude and purified IL-18BPa was tested for its ability to inhibit the biological activity of IL-18. IL-18BPa inhibited in a dose dependent manner the IFN-γ inducing activity of human and mouse IL-18 in murine splenocytes, PBMC and the human KG-1 cell line (FIG. 9).

The results of the various bioassays as well as the mobility shift assay (Example 8) demonstrated that inhibition of IL-18 activity is an intrinsic property of the cloned IL-18BP and not that of any accompanying impurities in urinary IL-18BP, such as the co-eluting fragment of defensin.

EXAMPLE 8

Electrophoretic Mobility Shift Assays

The effect of the urinary and the recombinant IL-18BP on IL-18-induced activation of NF-κB in human KG-1 cells was also studied. Human KG-1 cells ($4 \times 10^6$ in 1 ml RMPI) were stimulated with either huIL-18 (10 ng/ml) or huIL-18 pre-mixed with an IL-18BP (20 min, room temperature). After 20 min at 37° C., cells were washed three times with ice-cold PBS and immediately frozen in liquid nitrogen. Cell pellets were resuspended in three times the packed cell volume in buffer A (20 mM Tris pH 7.6, 0.4M NaCl, 0.2 mM EDTA, glycerol (20% by volume), 1.5 mM MgCl$_2$, 2 mM dithiothreitol (DDT), 0.4 mM PMSF, 1 mM Na$_3$VO$_4$, 2 µg/ml each of leupeptin, pepstatin and aprotinin). Cell debris was removed by centrifugation (15,000×g, 15 min.), aliquots of the supernatant were frozen in liquid nitrogen and stored at -80° C. Protein concentration was determined by a Bradford assay (Bio-Rad) using bovine serum albumin as standard. A double-stranded oligonucleotide corresponding to NF-κB binding element (10 pmol, Promega) was labeled with [$^{32}$P] dCTP (300 Ci/mmol) and T4 polynucleotide kinase (New England Biolabs). Free nucleotides were removed by a spin column. Extracts (10 µg protein) of cells treated with IL-18 or IL-18 plus IL-18BP were incubated (15 min., room temperature) with the labeled probe ($3 \times 10^4$ cpm) together with poly dI.dC (500 ng, Pharmacia) and denatured salmon sperm DNA (100 ng, Sigma) in 20 µl buffer consisting of HEPES (pH 7.5, 10 mM), 60 mM KCl, 1 mM MgCl$_2$, 2 mM EDTA, 1 mM DTF and glycerol (5% by volume). The mixtures were then loaded onto 5% non-denaturing polyacrylamide gels. Electrophoresis was performed at 185 V in 0.5×TBE (40 mM Tris HCl, 45 mM boric acid and 2.5 mM EDTA). Gels were vacuum dried and autoradiographed overnight at -80° C. IL-18 was found to induce the formation of the p50 NF-κB homodimer and the p65/p50 NF-κB heterodimer. Urinary as well as recombinant IL-18BP inhibited the activation of NF-κB by IL-18, as determined by an electrophoretic mobility shift assay with KG-1 cell extracts binding a radiolabeled oligonucleotide corresponding to the NF-κB consensus sequence.

EXAMPLE 9

Expression of IL-18BP in *E. coli*, Yeast and Insect Cells

IL-18BP may also be produced by other recombinant cells such as prokaryotic cells, e.g., *E. coli*, or other eukaryotic cells, such as yeast and insect cells. Well known methods are available for constructing appropriate vectors, carrying DNA that codes for either IL-18BP and suitable for transforming *E. coli* and yeast cells, or infecting insect cells in order to produce recombinant IL-18BP. For expression in yeast cells, the DNA coding for IL-18BP (Example 6) is cut out and inserted into expression vectors suitable for transfection of yeast cells. For expression in insect cells, a DNA coding for IL-18BP is inserted into baculovirus and the insect cells are infected with said recombinant baculovirus. For expression in *E. coli*, the DNA coding for IL-18BP is subjected to site directed mutagenesis with appropriate oligonucleotides, so that an initiation ATG codon is inserted just prior to the first codon of mature IL-18BP. Alternatively, such DNA can be prepared by PCR with suitable sense and antisense primers. The resulting cDNA constructs are then inserted into appropriately constructed prokaryotic expression vectors by techniques well known in the art (23).

EXAMPLE 10

Construction of Adeno-Associated Expression Vector for In Vivo Expression of IL-18BPa A functional gene coding for IL-18BPa is constructed based on plasmid pcDNA3 (Invitrogen, San Diego Calif.). The IL-18BP cDNA with a Kozak consensus sequence at the 5' end is ligated into the Xba I site of pcDNA3 in a way that destroys the restriction site. New Xba I sites are inserted by site-directed mutagenesis before the neomycin cassette (base 2151 of the original pcDNA3 sequence) and after the SV40 polyadenylation signal (base 3372 of the original pcDNA3 sequence). This construct is then cut with Xba I and the resulting 4.7 kb minigen is inserted at the Xba I site of plasmid psub201 as described (Snyder et al, 1996, Current Protocols in Human Genetics, Chapters 12.1.1-12.1.17, John Wiley & Sons). The resulting recombinant plasmid is cotransfected with the helper AAV plasmid pAAV/Ad into human T293 cells. The cultures are then infected with adenovirus as a helper virus and the cells are collected after 48-60 hours of incubation. The cells are subjected to 3 freeze-thaw cycles, cell debris is removed by centrifugation, and the supernatant is brought to 33% saturation with ammonium sulfate. The mixture is then centrifuged and rAAV is precipitated from the supernatant by bringing the ammonium sulfate to 50% saturation. The virus is further purified by CsCl, dialyzed and finally heated for 15 min at 56° C. to destroy any adenovirus.

EXAMPLE 11

Construction of Recombinant Fusion Proteins of IL-18BP

The production of proteins comprising IL-18BP fused to the constant region of IgG2 heavy chain may be carried out as follows: the DNA of IL-18BP is subjected to site-directed mutagenesis with appropriate oligonucleotides so that a unique restriction site is introduced immediately before and after the coding sequences. A plasmid bearing the constant region of IgG2 heavy chain, e.g. pRKCO42Fc1 (6) is subjected to similar site-directed mutagenesis to introduce the same unique restriction site as close as possible to Asp 216 of IgG1 heavy chain in a way that allows translation in phase of the fused protein. A dsDNA fragment, consisting of 5' non-translated sequences and encoding for IL-18BP is prepared by digestion at the unique restriction sites or alternatively by PCR with appropriately designed primers. The mutated pRKCD42Fc1 is similarly digested to generate a large fragment containing the plasmid and the IgG1 sequences. The two fragments are then ligated to generate a new plasmid, encoding a polypeptide precursor consisting of IL-18BP and about 227 C-terminal amino acids of IgG1 heavy chain (hinge region and CH2 and CH3 domains). The DNA encoding the fused proteins may be isolated from the plasmid by digestion with appropriate restriction enzymes and then inserted into efficient prokaryotic or eukaryotic expression vectors.

EXAMPLE 12

Production of Chemically Modified IL-18BPs

In order to increase the half-life of the IL-18BPs in plasma, IL-18BPs which are chemically modified with polyethylene glycol (PEG) may be made. The modification may be done by cross linking PEG to a cysteine residue of the IL-18BP molecules. Mutant IL-18BPs may be constructed which contain an extra cysteine residue at the amino terminus, glycosylation sites, and the carboxyl terminus of each IL-18BP. The mutagenesis may be carried out by PCR using oligonucleotides containing the desired mutation. These mutant proteins are expressed in the usual manner as well known in the art. Pegylation of these proteins will be carried out and the activity will be assessed.

EXAMPLE 13

Preparation of Polyclonal Antibodies to IL-18BP

Rabbits were initially injected subcutaneously with 5 µg of a pure preparation of the urinary IL-18BP, emulsified in complete Freund's adjuvant. Three weeks later, they were injected again subcutaneously with 5 µg of the IL-18BP preparation in incomplete Freund's adjuvant. Two additional injections of IL-18BP as solution in PBS were given at 10 day intervals. The rabbits were bled 10 days after the last immunization. The development of antibody level was followed by a radio-immunoassay. $^{125}$I-labeled IL-18BP (166,000 cpm) was mixed with various dilutions (1:50, 1:500, 1:5,000 and 1:50,000) of the rabbit serum. A suspension of protein-G agarose beads (20 µl, Pharmacia) was added in a total volume of 200 µl. The mixture was left for 1 hour at room temperature, the beads were then washed 3 times and bound radioactivity was counted. Rabbit antiserum to human leptin was used as a negative control. The titer of the IL-18R antiserum was between 1:500 and 1:5000, while that of the negative control was less than 1:50.

EXAMPLE 14

Preparation of Monoclonal Antibodies to IL-18BP

Female Balb/C mice (3 months old) are first injected with 2 µg purified IL-18BP in an emulsion of complete Freund's adjuvant, and three weeks later, subcutaneously in incomplete Freund's adjuvant. Three additional injections are given at 10 day intervals, subcutaneously in PBS. Final boosts are given intraperitoneally 4 and 3 days before the fusion to the mouse showing the highest binding titer as determined by IRIA (see below). Fusion is performed using NSO/1 myeloma cell line and lymphocytes prepared from both the spleen and lymph nodes of the animal as fusion partners. The fused cells are distributed into microculture plates and the hybridomas are selected in DMEM supplemented with HAT and 15% horse serum. Hybridomas that are found to produce antibodies to IL-18BP are subcloned by the limiting dilution method and injected into Balb/C mice that had been primed with pristane for the production of ascites. The isotypes of the antibodies are defined with the use of a commercially available ELISA kit (Amersham, UK).

The screening of hybridomas producing anti-IL-18BP monoclonal antibodies is performed as follows: Hybridoma supernatants are tested for the presence of anti-IL-18BP antibodies by an inverted solid phase radioimmunoassay (IRIA). ELISA plates (Dynatech Laboratories, Alexandria, Va.) are coated with Talon-purified IL-18BPa-His$_6$ (10 μg/ml, 100 μl/well). Following overnight incubation at 4° C., the plates are washed twice with PBS containing BSA (0.5%) and Tween 20 (0.05%) and blocked in washing solution for at least 2 hrs at 37° C. Hybridoma culture supernatants (100 μl/well) are added and the plates are incubated for 4 hrs at 37° C. The plates are washed 3 times and a conjugate of goat-anti-mouse horseradish peroxidase (HRP, Jackson Labs, 1:10,000, 100 μl/well) is added for 2 hrs at room temperature. The plates are washed 4 times and the color is developed by ABTS (2,2'-azino-bis(3-ethylbenzthiazoline-6-sulfonic acid, Sigma) with $H_2O_2$ as a substrate. The plates are read by an automatic ELISA reader. Samples giving OD that are at least 5 times higher than the negative control value are considered positive.

EXAMPLE 15

Affinity Chromatography of IL-18BP with Monoclonal Antibodies

Antibodies against IL-18BP are utilized for the purification of IL-18BP by affinity chromatography. Ascitic fluid containing the monoclonal antibody secreted by the hybridoma is purified by ammonium sulfate precipitation at 50% saturation followed by extensive dialysis against PBS. About 10 mg of immunoglobulins are bound to 1 ml Affigel 10 (BioRad USA), as specified by the manufacturer.

250 ml of human urinary proteins (equivalent to 250 l of crude urine) are loaded on 0.5 ml of the anti IL-18BP antibody column at 4° C. at a flow rate of 0.25 ml/min. The column is washed with PBS until no protein is detected in the washings. IL-18BP is eluted by 25 mM citric acid buffer, pH 2.2 (8×1 column volume fractions) and immediately neutralized by 1 M $Na_2CO_3$. Further purification of this preparation is obtained by size exclusion chromatography.

EXAMPLE 16

ELISA Test

Microtiter plates (Dynatech or Maxisorb, by Nunc) are coated with anti-IL-18BP monoclonal antibody (serum free hybridoma supernatant or ascitic fluid immunoglobulins) overnight at 4° C. The plates are washed with PBS containing BSA (0.5%) and Tween 20 (0.05%) and blocked in the same solution for at least 2 hrs at 37° C. The tested samples are diluted in the blocking solution and added to the wells (100 μl/well) for 4 hrs at 37° C. The plates are then washed 3 times with PBS containing Tween 20 (0.05%) followed by the addition of rabbit anti-IL-18BP serum (1:1000, 100 μl/well) for further incubation overnight at 4° C. The plates are washed 3 times and a conjugate of goat-anti-rabbit horseradish peroxidase (HRP, Jackson Labs, 1:10,000, 100 μl/well) was added for 2 hrs at room temperature. The plates were washed 4 times and the color is developed by ABTS (2,2'-azino-bis(3-ethylbenzthiazoline-6-sulfonic acid, Sigma) with $H_2O_2$ as a substrate. The plates are read by an automatic ELISA reader.

EXAMPLE 17

Non-Glycosylated Human IL-18BP is Biologically Active

Purified recombinant IL-18BPa was tested for its ability to inhibit the biological activity of IL-18. IL-18BPa inhibited in a dose dependent manner the IFN-γ inducing activity of human and mouse IL-18 in murine splenocytes, PBMC and the human KG-1 cell line (FIG. 9).

Purified IL-18BPa having a His$_6$ tag at the C-terminus (1.5 μg, 50 μl) was adjusted to pH 7.5 and mixed with N-glycosidase F (3 μl, 500,000 U/ml, PNGase F, New England Biolabs). The mixture was incubated for 24 h at 37° C. under non-denaturing conditions. Aliquots from the sample and from undigested IL-18BP-His$_6$ were analyzed by SDS-PAGE under non-reducing conditions followed by immunoblotting with antibodies to IL-18PB. It was found that the ~40 kD band of IL-18BP-His$_6$ disappeared in the PNGase-treated fraction and a new ~20 kD band was obtained. The molecular mass of the product and the specificity of PNGase F indicated that IL-18BP-His$_6$ was fully deglycosylated.

The PNGase-treated fraction, undigested IL-18BP-His$_6$ and control sample containing PNGase in buffer were absorbed separately on Talon beads, washed with phosphate buffer and eluted with imidazole (100 mM). The eluted fractions were subjected to bioassay using human IL-18 (20 ng/ml), LPS (2 μg/ml) and murine splenocytes. The results are shown in the following table:

| Sample | IFN-γ (ng/ml) |
|---|---|
| Control | 7.5 |
| Non-digested IL-18BP-His$_6$ | 0 |
| PNGase-treated IL-18BP-His$_6$ | 0 |

Therefore, it is concluded that deglycosylated IL-18BP is biologically active as a modulator of IL-18 activity.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

REFERENCES

1. Anderson, D. M., et al., *A homologue of the TNF receptor and its ligand enhance T-cell growth and dendritic-cell function*. Nature, 1997. 390(6656): p. 175-179.

2. Bollon, D. P., et al. (1980) *J. Clin Hematol. Oncol.* 10:39-48.
3. Botstein, D., et al. (1982) Miami Wint. Symp. 19:265-274.
4. Broach, J. R., in "The Molecular Biology of the Yeast *Saccharomyces*: Life Cycle and Inheritance", Cold Spring Harbor Laboratory, Cold Spring Harbor, N.Y., pp. 445-470 (1981).
5. Broach, J. R., (1982) *Cell* 28:203-204.
6. Byrn R. A. et al., 1990, *Nature* (London) 344:667-670.
7. Car, B. D., V. M. Eng, B. Schnyder, L. Ozmen, S. Huang, P. Gallay, D. Heumann, M. Aguet, and B. Ryffel. 1994. Interferon gamma receptor deficient mice are resistant to endotoxic shock. *J. Exp. Med.* 179:1437-44 issn: 0022-1007.
8. Chater, K. F. et al., in "Sixth International Symposium on Actinomycetales Biology", Akademiai Kaido, Budapest, Hungary (1986), pp. 45-54).
9. Conti, B., J. W. Jahng, C. Tinti, J. H. Son, and T. H. Joh. 1997. Induction of interferon-gamma inducing factor in the adrenal cortex. *J. Biol. Chem.* 272:2035-2037.
10. Dao, T., K. Ohashi, T. Kayano, M. Kurimoto, and H. Okamura. 1996. Interferon-gamma-inducing factor, a novel cytokine, enhances Fas ligand-mediated cytotoxicity of murine T helper 1 cells. Cell-Immunol. 173:230-5 issn: 0008-8749.
11. Engelmann, H., D. Aderka, M. Rubinstein, D. Rotman, and D. Wallach. 1989. A tumor necrosis factor-binding protein purified to homogeneity from human urine protects cells from tumor necrosis factor toxicity. *J. Biol. Chem.* 264:11974-11980.
12. Engelmann, H., D. Novick, and D. Wallach. 1990. Two tumor necrosis factor-binding proteins purified from human urine. Evidence for immunological cross-reactivity with cell surface tumor necrosis factor receptors. *J. Biol. Chem.* 265:1531-1536.
13. Fantuzzi, G., et al., *IL-18 regulation of IFN-g production and cell proliferation as revealed in interleukin-1b converting enzyme-deficient mice.* Blood, 1998. 91: p. 2118-2125.
14. Gryczan, T., "The Molecular Biology of the Bacilli", Academic Press, NY (1982), pp. 307-329).
15. Gutkind, J. S., et al., *A novel c-fgr exon utilized in Epstein-Barr virus-infected B lymphcytes but not in mormal monocytes.* Molec. Cell. Biol., 1991. 11: p. 1500-1507.
16. Heremans, H., J. Van Damme, C. Dillen, R. Dijkmans, and A. Billiau. 1990. Interferon gamma, a mediator of lethal lipopolysaccharide-induced Shwartzman-like shock reactions in mice. *J. Exp. Med.* 171:1853-69 issn: 0022-1007.
17. Izaki, K. (1978) *Jpn. J. Bacteriol.* 33:729-742).
18. John, J. F., et al. (1986) Rev. Infect. Dis. 8:693-704).
19. Kendall, K. J. et al. (1987) *J. Bacteriol.* 169:4177-4183).
20. Kohno, K., J. Kataoka, T. Ohtsuki, Y. Suemoto, 1. Okamoto, M. Usui, M. Ikeda, and M. Kurimoto. 1997. IFN-gamma-inducing factor (IGIF) is a costimulatory factor on the activation of Th1 but not Th2 cells and exerts its effect independently of IL-12. *J. Immunol.* 158:1541-1550.
21. Maliszewski, C. R., T. A. Sato, T. Vanden Bos, S. Waugh, S. K. Dower, J. Slack, M. P. Beckmann, and K. H. Grabstein. 1990. Cytokine receptors and B cell functions. 1. Recombinant soluble receptors specifically inhibit IL-1- and IL-4-induced B cell activities in vitro. *J. Immunol.* 144:3028-3033.
22. Maniatis, T., in "Cell Biology: A Comprehensive Treatise, Vol. 3: Gene Expression", Academic Press, NY, pp. 563-608 (1980).
23. Maniatis et al., Molecular Cloning: A Laboratory Manual, Cold Spring Harbor Laboratory, New York, 1982.
24. Micallef, M. J., T. Ohtsuki, K. Kohno, F. Tanabe, S. Ushio, M. Namba, T. Tanimoto, K. Torigoe, M. Fujii, M. Ikeda, S. Fukuda, and M. Kurimoto. 1996. Interferon-gamma-inducing factor enhances T helper 1 cytokine production by stimulated human T cells: synergism with interleukin-12 for interferon-gamma production. *Eur-J-Immunol* 26:1647-51 issn: 0014-2980.
25. Mizushima, S. and Nagata, S. (1990) pEF-BOS, a powerful mammalian expression vector. Nucleic Acid Res. 18:5322-5328.
26. Nakamura, K., H. Okamura, K. Nagata, T. Komatsu, and T. Tamura. 1993. Purification of a factor which provides a costimulatory signal for gamma interferon production. Infect-Immun 61:64-70 issn: 0019-9567.
27. Nakamura, K., H. Okamura, M. Wada, K. Nagata, and T. Tamura. 1989. Endotoxin-induced serum factor that stimulates gamma interferon production. Infect-Immun 57:590-5 issn: 0019-9567.
28. Novick, D., B. Cohen, and M. Rubinstein. 1994. The Human Interferon alpha/beta Receptor—Characterization and Molecular Cloning. *Cell* 77:391-400.
29. Novick, D., B. Cohen, and M. Rubinstein. 1992. Soluble Interferon-alpha Receptor Molecules Are Present in Body Fluids. FEBS Lett 314:445-448.
30. Novick, D., H. Engelmann, D. Wallach, and M. Rubinstein. 1989. Soluble cytokine receptors are present in normal human urine. *J. Exp. Med.* 170:1409-1414.
31. Okamura, H., H. Tsutsui, T. Komatsu, M. Yutsudo, A. Hakura, T. Tanimoto, K. Torigoe, T. Okura, Y. Nukada, K. Hattori, K. Akita, M. Namba, F. Tanabe, K. Konishi, S. Fukuda, and M. Kurimoto. 1995. Cloning of a new cytokine that induces IFN-gamma production by T cells. *Nature* 378:88-91.
32. Rothe, H., N. A. Jenkins, N. G. Copeland, and H. Kolb. 1997. Active stage of autoimmune diabetes is associated with the expression of a novel cytokine, IGIF, which is located near Idd2. *J-Clin-Inves.t* 99:469-74 issn: 0021-9738.
33. Sambrook, J., E. F. Fritsch, and M. T., *Molecular Cloning: A laboratory manual.* 2nd ed. ed. 1989, Cold Spring Harbor, N.Y.: Cold Spring Harbor Laboratory.
34. Simonet, W. S., et al., *Osteoprotegerin: a novel secreted protein involved in the regulation of bone density.* Cell, 1997. 89(2): p. 309-319.
35. Sompayrac, L. H. and K. L. Danna, *Efficient infection of monkey cells with DIVA of simian virus* 40. Proc. Nat'l. Acad. Sci. USA, 1981. 78: p. 7575-7578.
36. Sparks, C. A., et al., *Assignment of the nuclear mitotic apparatus protein NuMA gene to human chromosome 11q13.* Genomics, 1993.17: p. 222-224.
37. Tsutsui, H., K. Nakanishi, K. Matsui, K. Higashino, H. Okamura, Y. Miyazawa, and K. Kaneda. 1996. IFN-gamma-inducing factor up-regulates Fas ligand-mediated cytotoxic activity of murine natural killer cell clones. *J. Immunol.* 157:3967-73 issn: 0022-1767.
38. Ushio, S., M. Namba, T. Okura, K. Hattori, Y. Nukada, K. Akita, F. Tanabe, K. Konishi, M. Micallef, M. Fujii, K. Torigoe, T. Tanimoto, S. Fukuda, M. Ikeda, H. Okamura, and M. Kurimoto. 1996. Cloning of the cDNA for human IFN-gamma-inducing factor, expression in *Escherichia coli*, and studies on the biologic activities of the protein. *J. Immunol.* 156:4274-4279.34. Okayama, H. and Berg, P. (1983) A cDNA cloning vector that permits expression of cDNA inserts in mammalian cells. Mol. Cell. Biol. 3:280-289.
39. Yasuda, H., et al., *Identity of osteoclastogenesis inhibitory factor (OCIF) and osteoprotegerin (OPG): a mechanism by which OPG/OCIF inhibits osteoclastogenesis in vitro.* Endocrinology, 1998.139: p. 1329-1337.

What is claimed is:

1. An isolated nucleic acid encoding the polypeptide of SEQ. ID. NO. 4, 6 or 8.

2. An isolated nucleic acid comprising a nucleotide sequence encoding a polypeptide which has at least 95% sequence identity to SEQ ID. NO. 2 or 6 and binds IL-18.

3. An isolated nucleic acid molecule which hybridizes under stringent condition to the entire nucleic acid sequence of SEQ 1, 3, 5, or 7.

4. An isolated nucleic acid encoding a polypeptide of SEQ. ID. NO. 2, 4, 6 or 8 except wherein said polypeptide does not have a leader sequence.

5. An isolated nucleic acid molecule comprising a nucleotide sequence encoding a IL-18 binding protein (IL-18BP) wherein said IL-18BP comprises the amino acid sequence of SEQ ID NO:10 and is selected from the group consisting of (a) a polypeptide comprising the amino acid sequence of SEQ ID NO:2 or 6;

(b) a polypeptide as defined in (a) without a leader sequence;

(c) a mutein of the polypeptide defined in (a) or (b), characterized in that the mutein has at least 95% sequence identity to SEQ ID NO: 2 or 6, and binds IL-18.

6. The isolated nucleic acid molecule of claim 1, 2, 3, 4 or 5, wherein said nucleic acid is genomic DNA.

7. The isolated nucleic acid molecule of claim 1, 2, 3, 4 or 5, wherein said nucleic acid is cDNA.

8. The isolated nucleic acid molecule of claim 1, 2, 3, 4 or 5, wherein said nucleic acid is operably linked to a promoter or an enhancer.

9. A replicable expression vehicle comprising the nucleic acid molecule of claim 1, 2, 3, 4, or 5.

10. An isolated host cell comprising the expression vehicle of claim 9.

11. The host cell of claim 10 wherein said cell is a eukaryotic cell.

12. The host cell of claim 10, wherein said cell is a prokaryotic cell.

13. A method of producing a polypeptide of SEQ ID NO: 4, 6 or 8 comprising culturing a host cell according to claim 10, 11 or 12 under conditions allowing expression of said polypeptide.

14. The method of claim 13, further comprising isolating the polypeptide.

15. A composition comprising the nucleic acid molecule of claim 1, 2, 3, 4, or 5 and a carrier.

16. A composition comprising the expression vector of claim 9 and a carrier.

17. A replicable expression vehicle comprising the nucleic acid molecule of claim 6.

18. A replicable expression vehicle comprising the nucleic acid molecule of claim 7.

19. A replicable expression vehicle comprising the nucleic acid molecule of claim 8.

20. An isolated host cell comprising the expression vehicle of claim 17.

21. An isolated host cell comprising the expression vehicle of claim 18.

22. An isolated host cell comprising the expression vehicle of claim 19.

23. The host cell of claim 20, wherein said cell is a eukaryotic cell.

24. The host cell of claim 21, wherein said cell is a eukaryotic cell.

25. The host cell of claim 22, wherein said cell is a eukaryotic cell.

26. The host cell of claim 20, wherein said cell is a prokaryotic cell.

27. The host cell of claim 21, wherein said cell is a prokaryotic cell.

28. The host cell of claim 22, wherein said cell is a prokaryotic cell.

29. A method of producing a polypeptide of SEQ ID NO: 4, 6 or 8 comprising culturing a host cell according to claim 20, 21, 22, 23, 24, 25, 26, 27, or 28 under conditions allowing expression of said polypeptide.

30. The method of claim 29, further comprising isolating the polypeptide.

31. A composition comprising the expression vector of claim 17 and a carrier.

32. A composition comprising the expression vector of claim 18 and a carrier.

33. A composition comprising the expression vector of claim 19 and a carrier.

34. A composition comprising the nucleic acid molecule of claim 6 and a carrier.

35. A composition comprising the nucleic acid molecule of claim 7 and a carrier.

36. A composition comprising the nucleic acid molecule of claim 8 and a carrier.

* * * * *